(12) United States Patent
Hasui et al.

(10) Patent No.: US 8,883,788 B2
(45) Date of Patent: Nov. 11, 2014

(54) FUSED HETEROCYCLIC RING COMPOUND

(75) Inventors: Tomoaki Hasui, Kanagawa (JP);
Makoto Fushimi, Kanagawa (JP);
Hironori Kokubo, Kanagawa (JP);
Takenori Hitaka, Kanagawa (JP);
Shotaro Miura, Kanagawa (JP);
Takahiko Taniguchi, Kanagawa (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 0 days.

(21) Appl. No.: 13/814,035

(22) PCT Filed: Aug. 3, 2011

(86) PCT No.: PCT/JP2011/067808
§ 371 (c)(1),
(2), (4) Date: Feb. 4, 2013

(87) PCT Pub. No.: WO2012/018058
PCT Pub. Date: Feb. 9, 2012

(65) Prior Publication Data
US 2013/0137700 A1 May 30, 2013

(30) Foreign Application Priority Data

Aug. 4, 2010 (JP) .................................. 2010-175395

(51) Int. Cl.
| A61K 31/50 | (2006.01) |
|---|---|
| A61K 31/501 | (2006.01) |
| C07D 403/14 | (2006.01) |
| C07D 401/12 | (2006.01) |
| C07D 471/04 | (2006.01) |
| A61K 9/20 | (2006.01) |
| C07D 487/04 | (2006.01) |
| C07D 401/14 | (2006.01) |
| A61K 31/00 | (2006.01) |

(52) U.S. Cl.
CPC ............ *C07D 403/14* (2013.01); *C07D 401/12* (2013.01); *C07D 471/04* (2013.01); *A61K 9/2018* (2013.01); *C07D 487/04* (2013.01); *C07D 401/14* (2013.01); *A61K 9/2059* (2013.01); *A61K 31/00* (2013.01)
USPC ................................ 514/252.04; 514/252.06

(58) Field of Classification Search
None
See application file for complete search history.

(56) References Cited

U.S. PATENT DOCUMENTS

| 4,707,181 A | 11/1987 | Patterson |
| 2003/0229096 A1 | 12/2003 | Buettelmann et al. |

FOREIGN PATENT DOCUMENTS

| EP | 1 426 365 | 6/2004 |
| FR | 1 547 379 | 11/1968 |
| WO | WO 2007113856 A2 * | 10/2007 |
| WO | 2009/152825 | 12/2009 |
| WO | 2009/158393 | 12/2009 |
| WO | 2010/063610 | 6/2010 |
| WO | 2010/090737 | 8/2010 |

OTHER PUBLICATIONS

Anderson (Chem and Biol 10:787-797, 2003).*
Supplementary European Seach Report dated Nov. 29, 2013 in EP Application No. 11814683.6.
F. A. Al-Omran et al., "Studies with S-Alkylpyrimidine: New Route for the Synthesis Derivatives of Isoxazol, Pyrazolo[1,5-α]Pyrimidine, Pyridazine, Pyridine, Thieno[2,3-b]Pyridine and Thiophene of Potential Anti-HIV", Journal of Heterocyclic Chemistry, vol. 45, No. 4, pp. 1057-1063, Jul. 2008.
Database PubChem Compound, Database Accession No. CID 1847101 (2005).
Database PubChem Compound, Database Accession No. CID 10146248 (2006).
Database PubChem Compound, Database Accession No. CID 11324285 (2006).
Database PubChem Compound, Database Accession No. CID 19989332 (2007).
Database PubChem Compound, Database Accession No. CID 19989347 (2007).
Database PubChem Compound, Database Accession No. CID 19989349 (2007).
Database PubChem Compound, Database Accession No. CID 19989351 (2007).
Database PubChem Compound, Database Accession No. CID 44535917 (2010).
Database Registry, Database Accession No. CID 883018-02-8 (2006).
V. Konecny et al., "Pyridazinones. I. Preparation of 2,4-Disubstituted 5-Hydroxy-3(2H)-Pyridazinones and 2,5-Disubstituted 4-hydroxy-3(2H)-Pyridazinones", Chemick Zvesti-Chemical Papers, Veda, Bratislava, SK, vol. 30, pp. 663-673, Jan. 1976.
N. Suree et al., "Discovery and Structure-Activity Relationship Analysis of *Straphylococcus aureus* Sortase A Inhibitors", Bioorganic & Medicinal Chemistry, vol. 17, No. 20, pp. 7174-7185, Sep. 6, 2009.
International Search Report issued Sep. 27, 2011 in International (PCT) Application No. PCT/JP2011/067808.

* cited by examiner

*Primary Examiner* — Craig Ricci
*Assistant Examiner* — Jared D Barsky
(74) *Attorney, Agent, or Firm* — Wenderoth, Lind & Ponack, LLP

(57) ABSTRACT

Provided is a compound having a PDE10A inhibitory action, and useful as a medicament for the prophylaxis or treatment of mental diseases such as schizophrenia and the like, and the like. A compound represented by the formula (I):

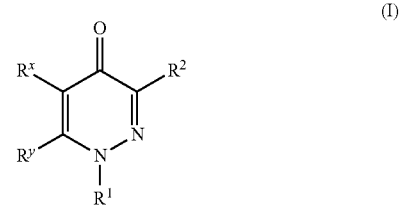

wherein each symbol is as defined in the DESCRIPTION, or a salt thereof.

8 Claims, No Drawings

FUSED HETEROCYCLIC RING COMPOUND

TECHNICAL FIELD

The present invention relates to a fused heterocyclic compound.

BACKGROUND OF THE INVENTION

Phosphodiesterase (PDE) is an enzyme that hydrolyzes cAMP and cGMP that function as intracellular second messengers into 5'-AMP and 5'-GMP, respectively. PDE gene is constituted with 21 genes, and currently classified into 11 kinds of families based on the molecular structure of the enzymes. Furthermore, each PDE is classified into the following 3 kinds: 1) cAMP-PDEs (PDE4, PDE7, PDE8), 2) cGMP-PDE (PDE5, PDE6, PDE9), and 3) dual-substrate PDEs (PDE1, PDE2, PDE3, PDE10, PDE11), based on the substrate specificity.

cAMP and cGMP are involved in the control of various physiological functions such as control of ion channel, muscle relaxation, learning and memory function, differentiation, apoptosis, lipogenesis, glycogenolysis and gluconeogenesis. Particularly, they are known to play an important role in the differentiation and survival, as well as control of neurotransmission of the nerve cell (non-patent document 1). Phosphorylation of various molecules that control physiological functions such as transcription factors, ion channel and receptor, which is caused by protein kinase A (PKA) and protein kinase G (PKG), contributes to such control by cAMP and cGMP, and the amounts of cAMP and cGMP in the cell are under spatiotemporal regulation via generation by adenylate cyclase and guanylate cyclase in response to extracellular stimulations and degradation thereof by PDE (non-patent document 2). Since PDE is a sole enzyme that decomposes cAMP and cGMP in vivo, PDE is considered to play an important role in the regulation of cyclic nucleotide signaling.

PDE10A is a molecule cloned by 3 independent groups and reported in 1999 (non-patent documents 3, 4, 5). Expression analysis thereof has clarified that PDE10A shows high expression only in the brain and testis, and has a localized expression pattern in the PDE family (non-patent documents 6, 7). In the brain, both PDE10A mRNA and PDE10A protein show high expression in medium spiny nerve cells of the striatum (medium spiny neurons, MSNs) (non-patent documents 8, 9). MSNs are classified as two major kinds of pathways. One of them is called a direct pathway or nigrostriatal pathway, and mainly expresses dopamine $D_1$ receptors. The other pathway, indirect pathway, is called a striatum-globus pallidus pathway, and mainly expresses dopamine $D_2$ receptors. The direct pathway is involved in the functions of motion execution and reward learning and, on the other hand, the indirect pathway is involved in the suppression of motility. The activity of the output nucleus of the basal nucleus is regulated by the balance of antagonistic inputs from these two kinds of pathways. Since PDE10A is expressed in MSNs of both pathways, the both pathways are considered to be activated by inhibition of PDE10A. Since the action of existing antipsychotic agents having a $D_2$ receptor shutting off action is mainly mediated by the activation of indirect pathway, a PDE10A inhibitor is expected to show an anti-mental disease action like existing drugs.

The excess $D_2$ receptor shutting off action in the brain by existing drugs causes side effects such as hyperprolactinemia and extrapyramidal syndrome. However, since PDE10A shows striatum pathway specific expression and shows a lower expression level in the pituitary gland mainly involved in the prolactin release, PDE10A inhibitor is considered to have no prolactin concentration increasing action in plasma. Moreover, since PDE10A is also expressed in the direct pathway MSNs and activated by a PDE10A inhibitor, it is considered to have superior characteristics than existing antipsychotic agents that activate only indirect pathways. That is, since the direct pathway is involved in the motion execution, it is considered to antagonistically act against extrapyramidal syndrome caused by excessive activation of indirect pathway. Furthermore, this pathway is expected to show actions to enhance the output from the striatum-thalamus circuit and promote cognitive functions of reward learning and problem solving. Since existing antipsychotic agents show a shutting off action on many receptors, they pose problems of side effects such as body weight increase and abnormal metabolism. PDE10A inhibitor is also considered to be superior to the existing drugs in the side effects, since it directly activates second messenger signaling without blocking dopamine and/or other neurotransmitter receptors. In view of the specific expression and its function in the brain nerve system, PDE10A is considered to be useful as a drug discovery target in neurological diseases, in particular, psychotic disorders such as schizophrenia.

Patent document 1 discloses, as a PDE10A inhibitor, a compound of the following formula:

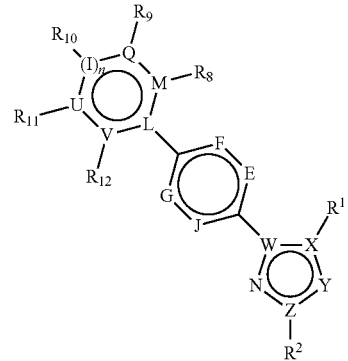

and the following compounds:

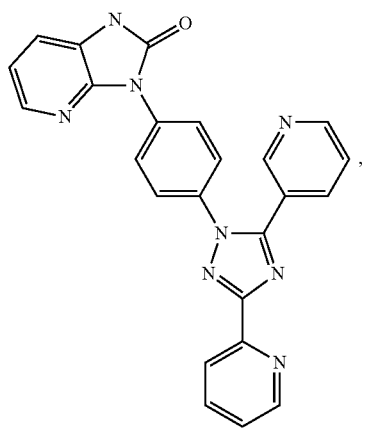

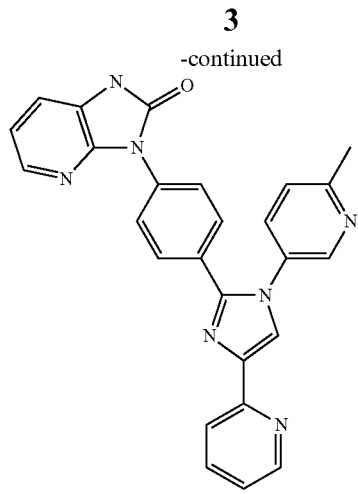
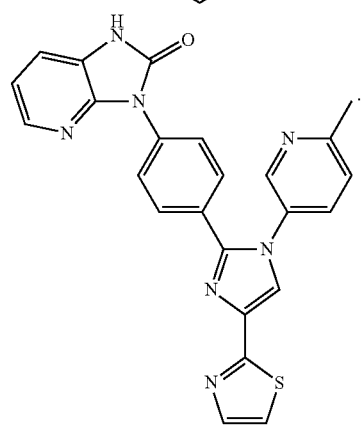
Patent document 2 discloses, as a PDE10A inhibitor, a compound of the following formula:
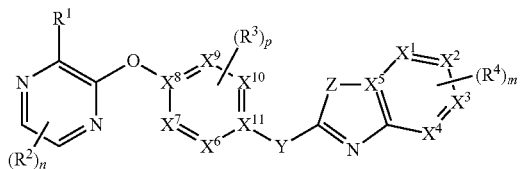
and the following compounds:
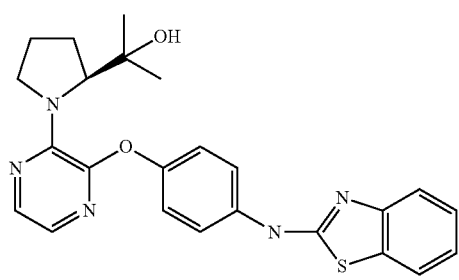
and
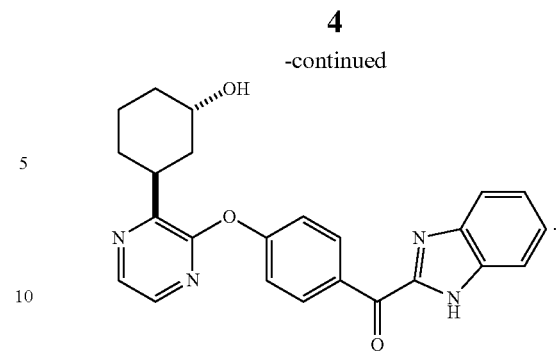
Patent document 3 discloses, as a PDE10A inhibitor, a compound of the following formula:
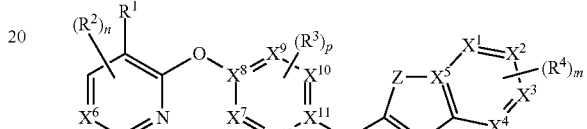
and the following compounds:
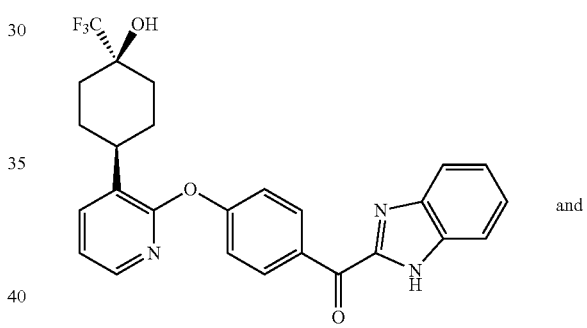
and
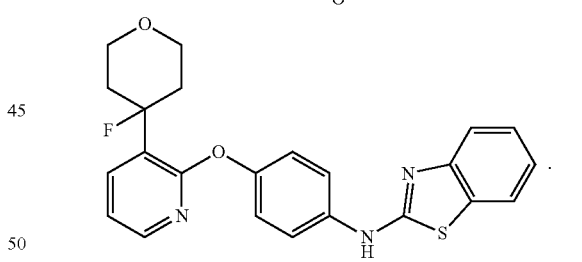
Patent document 4 discloses, as a PDE10A inhibitor, a compound of the following formula:
I
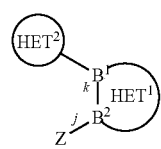

wherein Z is

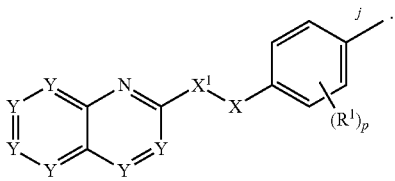

Patent document 5 discloses the following compound as a PDE10A inhibitor.

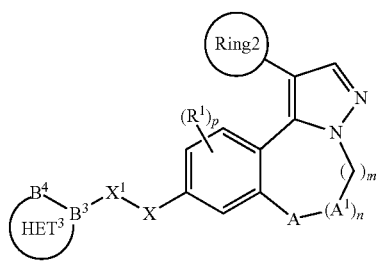

(I)

Patent document 6 discloses, as a PDE10A inhibitor, a compound of the following formula:

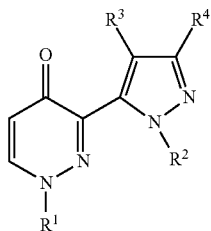

and the following compounds:

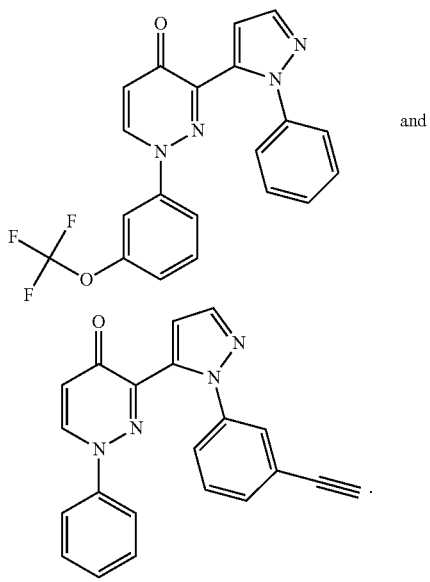

Patent document 7 discloses 5-(cyclopropylmethoxy)-3-(1-phenyl-1H-pyrazol-5-yl)-1-[3-(trifluoromethyl)phenyl]pyridazin-4(1H)-one.

In addition, patent documents 8 and 9 disclose the following compounds which are different from PDE10A inhibitors in the use thereof.

patent document 8: inhibitors of Lp-PLA2 enzyme
(1) N-(1-ethylpiperidin-4-yl)-2-{6-[(4-fluorobenzyl)sulfanyl]-3-methyl-4-oxopyridazin-1(4H)-yl}-N-{[4'-(trifluoromethyl)biphenyl-4-yl]methyl}acetamide,
(2) ethyl {6-[(4-fluorobenzyl)sulfanyl]-3-methyl-4-oxopyridazin-1(4H)-yl}acetate, and
(3) {6-[(4-fluorobenzyl)sulfanyl]-3-methyl-4-oxopyridazin-1(4H)-yl}acetic acid.

patent document 9: antibacterial agents of cepham compound
(1) benzyl 7-{[(2Z)-2-(2-amino-1,3-thiazol-4-yl)-3-methoxyprop-2-enoyl]amino}-3-{[(6-chloro-2-methyl-5-oxo-2,5-dihydropyridazin-3-yl)sulfanyl]methyl}-8-oxo-5-thia-1-azabicyclo[4.2.0]oct-2-ene-2-carboxylate 5-oxide,
(2) benzyl 3-{[(6-chloro-2-methyl-5-oxo-2,5-dihydropyridazin-3-yl)sulfanyl]methyl}-7-({(2Z)-2-[2-(formylamino)-1,3-thiazol-4-yl]-3-methoxyprop-2-enoyl}amino)-8-oxo-5-thia-1-azabicyclo[4.2.0]oct-2-ene-2-carboxylate,
(3) 7-{[(2Z)-2-(2-amino-1,3-thiazol-4-yl)-3-methoxyprop-2-enoyl]amino}-3-{[(6-chloro-4-hydroxy-2-methyl-5-oxo-2,5-dihydropyridazin-3-yl)sulfanyl]methyl}-8-oxo-5-thia-1-azabicyclo[4.2.0]oct-2-ene-2-carboxylic acid, and
(4) 7-[2-(5-amino-1,2,4-thiadiazol-3-yl)-2-ethoxyiminoacetamido]-3-(1-methyl-3-chloro-4-oxo-1,4-dihydropyridazin-6-yl)thiomethyl-3-cepham-4-carboxylic acid.

DOCUMENT LIST

Patent Documents patent document 1: WO2008/004117
patent document 2: WO2010/057121
patent document 3: WO2010/057126
patent document 4: WO2006/072828
patent document 5: WO2008/001182
patent document 6: WO2010/063610
patent document 7: WO2010/090737
patent document 8: WO2003/0041712
patent document 9: JP-A-01-216997

Non-Patent Documents non-patent document 1: Nat. Rev. Drug Disc. 2006, vol. 5: 660-670
non-patent document 2: Circ. Res. 2007, vol. 100(7): 950-966
non-patent document 3: Proc. Natl. Acad. Sci. USA 1999, vol. 96: 8991-8996
non-patent document 4: J. Biol. Chem. 1999, vol. 274: 18438-18445
non-patent document 5: Gene 1999, vol. 234: 109-117
non-patent document 6: Eur. J. Biochem. 1999, vol. 266: 1118-1127
non-patent document 7: J. Biol. Chem. 1999, vol. 274: 18438-18445
non-patent document 8: Eur. J. Biochem. 1999, vol. 266: 1118-1127
non-patent document 9: Brain Res. 2003, vol. 985:113-126

SUMMARY OF THE INVENTION

Problems to be Solved by the Invention

However, there is a further demand for a new phosphodiesterase (PDE) inhibitor.

The present invention aims to provide a compound having a PDE10A inhibitory action and useful as a prophylactic or therapeutic drug for mental diseases such as schizophrenia and the like.

Means of Solving the Problems

The present inventors discovered that a compound represented by the following formula (I) or a salt thereof (hereinafter sometimes to be referred to as compound (I) in this specification) has a PDE10A inhibitory action and after extensive investigation, completed the present invention.

In this specification, the compound (I), and a prodrug thereof is also referred to the compound of the present invention.

Accordingly, the present invention provides embodiments of the following respective items and the like.

[1] A compound represented by the formula (I):

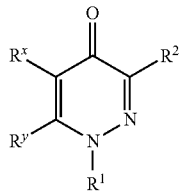

(I)

wherein
a partial structural formula:

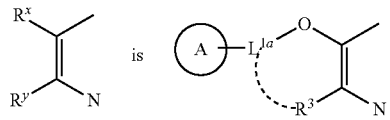

(1)

wherein ---- means that $L^{1a}$ and $R^3$ are optionally bonded to form a ring optionally further substituted, or

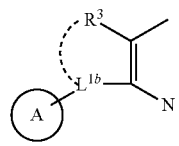

(2)

wherein ---- means that $L^{1b}$ and $R^3$ are optionally bonded to form a ring optionally further substituted,
ring A is an optionally substituted cyclic group,
$L^{1a}$ is
(a) a bond,
(b) —$Y^{1a}$—$X^1$—$Y^{1b}$— ($Y^{1a}$ is a bond, —O— or a methylene group; $Y^{1b}$ is a bond or a methylene group; $X^1$ is a divalent 3- to 8-membered cyclic group), or
(c) —$X^2$—$Y^2$— ($X^2$ is a bond, —O—, —$NR^a$—, —S—, —SO—, —$SO_2$— or —CO—; $Y^2$ is an optionally substituted $C_{1-6}$ alkylene group), $L^{1b}$ is
(a) —$Y^{3a}$—O—$Y^{3b}$— ($Y^{3a}$ is $C_{1-3}$ alkylene, $Y^{3b}$ is a bond or $C_{1-3}$ alkylene),
(b) —$Y^{4a}$—$X^4$—$Y^{4b}$— ($Y^{4a}$ is a bond, —O— or a methylene group; $Y^{4b}$ is —O— or a methylene group; $X^4$ is a divalent 3- to 8-membered cyclic group), or
(c) —$X^5$—$Y^5$— ($X^5$ is a bond, —O—, —$NR^a$—, —S—, —SO—, —$SO_2$— or —CO—; $Y^5$ is an optionally substituted $C_{1-6}$ alkylene group or optionally substituted $C_{1-6}$ alkylene-O—), $R^1$ is an optionally substituted $C_{1-6}$ alkyl group or an optionally substituted cyclic group,
$R^2$ is a hydrogen atom or a substituent,
$R^3$ is a hydrogen atom or a substituent, and
$R^a$ is a hydrogen atom or a $C_{1-6}$ alkyl group,
provided that
(1) when $L^{1a}$ and $R^3$ are bonded to form a ring optionally further substituted,
the partial structural formula of the formula (I):

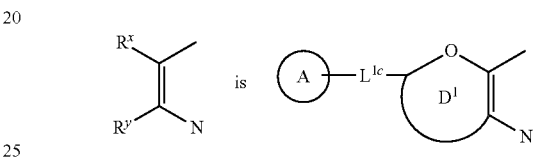

wherein
ring $D^1$ is a 5- or 6-membered heterocycle optionally further substituted,
ring A is as defined above, and
$L^{1c}$ is
(a) a bond,
(b) —$Y^{6a}$—O—$Y^{6b}$— ($Y^{6a}$ is $C_{1-3}$ alkylene, $Y^{6b}$ is a bond or $C_{1-3}$ alkylene),
(c) —$Y^{7a}$—$X^7$—$Y^{7b}$— ($Y^{7a}$ is a bond, —O— or a methylene group; $Y^{7b}$ is a bond, —O— or a methylene group; $X^7$ is a divalent 3- to 8-membered cyclic group), or
(d) —$X^8$—$Y^8$— ($X^8$ is a bond, —O—, —$NR^a$—, —S—, —SO—, —$SO_2$— or —CO—; $Y^8$ is an optionally substituted $C_{1-6}$ alkylene group or optionally substituted $C_{1-6}$-alkylene-O—)), (2) when Lb and $R^3$ are bonded to form a ring optionally further substituted,
the partial structural formula of the formula (I):

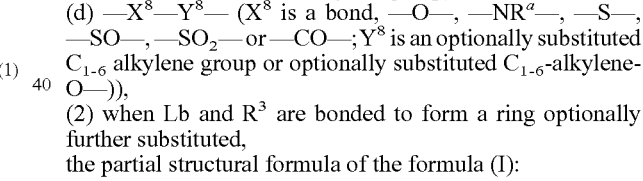

wherein ring $D^2$ is a 5- or 6-membered heterocycle optionally further substituted; and other symbols are as defined above, excluding 5-(cyclopropylmethoxy)-3-(1-phenyl-1H-pyrazol-5-yl)-1-[3-(trifluoromethyl)phenyl]pyridazin-4(1H)-one, N-(1-ethylpiperidin-4-yl)-2-{6-[(4-fluorobenzyl)sulfanyl]-3-methyl-4-oxopyridazin-1(4H)-yl}-N-{[4'-(trifluoromethyl)biphenyl-4-yl]methyl}acetamide, ethyl {6-[(4-fluorobenzyl)sulfanyl]-3-methyl-4-oxopyridazin-1(4H)-yl}acetate, {6-[(4-fluorobenzyl)sulfanyl]-3-methyl-4-oxopyridazin-1(4H)-yl}acetic acid, benzyl 7-{[(2Z)-2-(2-amino-1,3-thiazol-4-yl)-3-methoxyprop-2-enoyl]amino}-3-{[(6-chloro-2-methyl-5-oxo-2,5-dihydropyridazin-3-yl)sulfanyl]methyl}-8-oxo-5-thia-1-azabicyclo[4.2.0]oct-2-ene-2-carboxylate 5-oxide, benzyl 3-{[(6-chloro-2-methyl-5-oxo-2,5-dihydropyridazin-3-yl)sulfanyl]methyl}-7-({(2Z)-2-[2-(formylamino)-1,3-thiazol-4-yl]-3-methoxyprop-2-enoyl}amino)-8-oxo-5-thia-1-azabicyclo[4.2.0]oct-2-ene- 2-carboxylate, 7-{[(2Z)-2-(2-amino-1,3-thiazol-4-yl)-3-methoxyprop-2-enoyl]amino}-3-{[(6-chloro-4-hydroxy-2-methyl-5-oxo-2,5-dihydropyridazin-3-yl)sulfanyl]methyl}-8-oxo-5-thia-1-azabicyclo[4.2.0]oct-2-ene-2-carboxylic acid, and 7-[2-(5-amino-1,2,4-thiadiazol-3-yl)-2-ethoxyiminoacetamido]-3-(1-methyl-3-chloro-4-oxo-1,4-dihydropyridazin-6-yl)thiomethyl-3-cepham-4-carboxylic acid, or a salt thereof.

[2] The compound according to claim 1, wherein the partial structural formula:

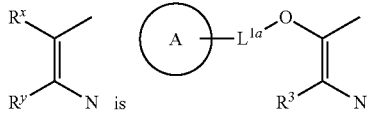

wherein ring A, $L^{1a}$ and $R^3$ are as defined in [1], or a salt thereof.

[3] 5-[2-(2,3-Dihydro-1H-imidazo[1,2-a]benzimidazol-1-yl)ethoxy]-1-methyl-3-(1-phenyl-1H-pyrazol-5-yl)pyridazin-4(1H)-one or a salt thereof.

[4] 1-(Cyclopropylmethyl)-5-[3-(1-methyl-1H-benzimidazol-2-yl)propoxy]-3-(1-phenyl-1H-pyrazol-5-yl)pyridazin-4(H)-one or a salt thereof.

[5] 1-(Cyclopropylmethyl)-5-[2-(2,3-dihydro-1H-imidazo[1,2-a]benzimidazol-1-yl)ethoxy]-3-(1-phenyl-1H-pyrazol-5-yl)pyridazin-4(1H)-one or a salt thereof.

[6] 5-(3-Imidazo[1,2-a]pyridin-2-ylpropoxy)-1-methyl-3-(1-phenyl-1H-pyrazol-5-yl)pyridazin-4(1H)-one or a salt thereof.

[7] 1-Cyclobutyl-5-[2-(2,3-dihydro-1H-imidazo[1,2-a]benzimidazol-1-yl)ethoxy]-3-(1-phenyl-1H-pyrazol-5-yl)pyridazin-4(1H)-one or a salt thereof.

[8] A medicament comprising the compound according to claim 1 or a salt thereof.

[9] The medicament of [8], which is a phosphodiesterase 10A inhibitor.

[10] The medicament of [8], which is a prophylactic or therapeutic drug for schizophrenia.

[11] A method of preventing or treating schizophrenia, which comprises administering an effective amount of the compound according to claim 1 or a salt thereof to a mammal.

[12] The compound according to claim 1 or a salt thereof for use in the prevention or treatment of schizophrenia.

[13] Use of the compound according to claim 1 or a salt thereof for the manufacture of a prophylactic or therapeutic drug for schizophrenia.

The present invention also provides embodiments of the following respective items and the like.

[Item 1] A compound represented by the formula (I):

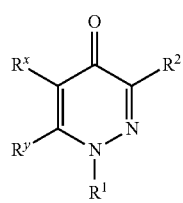

(I)

wherein
a partial structural formula:

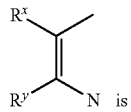

(1)

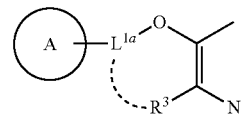

(- - - - means that $L^{1a}$ and $R^3$ are optionally bonded to form a ring optionally further substituted), or

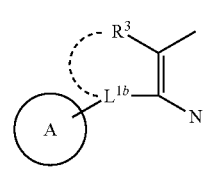

(2)

(- - - - means that $L^{1b}$ and $R^3$ are optionally bonded to form a ring optionally further substituted,
ring A is an optionally substituted cyclic group,
$L^{1a}$ is
(a) a bond,
(b) —$Y^{1a}$—$X^1$—$Y^{1b}$— ($Y^{1a}$ is a bond, —O— or a methylene group; $Y^{1b}$ is a bond or a methylene group; $X^1$ is a divalent 3- to 8-membered cyclic group), or
(c) —$X^2$—$Y^2$— ($X^2$ is a bond, —O—, —$NR^a$—, —S—, —SO—, —$SO_2$— or —CO—; $Y^2$ is an optionally substituted $C_{1-6}$ alkylene group),
$L^{1b}$ is
(a) —$Y^{3a}$—O—$Y^{3b}$— ($Y^{3a}$ is $C_{1-3}$ alkylene, $Y^{3b}$ is a bond or $C_{1-3}$ alkylene),
(b) —$Y^{4a}$—$X^4$—$Y^{4b}$— ($Y^{4a}$ is a bond, —O— or a methylene group; $Y^{4b}$ is —O— or a methylene group; $X^4$ is a divalent 3- to 8-membered cyclic group), or
(c) —$X^5$—$Y^5$— ($X^5$ is a bond, —O—, —$NR^a$—, —S—, —SO—, —$SO_2$— or —CO—; $Y^5$ is an optionally substituted $C_{1-6}$ alkylene group or optionally substituted $C_{1-6}$ alkylene-O—),
$R^1$ is an optionally substituted $C_{1-6}$ alkyl group or an optionally substituted cyclic group,
$R^2$ is a hydrogen atom or a substituent,
$R^3$ is a hydrogen atom or a substituent,
$R^a$ is a hydrogen atom or a $C_{1-6}$ alkyl group,
provided that
(1) when $L^{1a}$ and $R^3$ are bonded to form a ring optionally further substituted,
the partial structural formula of the formula (I):

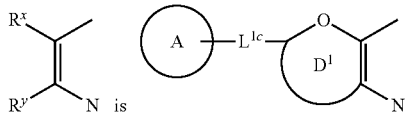

wherein
ring $D^1$ is a 5- or 6-membered heterocycle optionally further substituted;
ring A is as defined above;

$L^{1c}$ is (a) a bond, (b) —$Y^{6a}$—O—$Y^{6b}$— ($Y^{6a}$ is $C_{1-3}$ alkylene, $Y^{6b}$ is a bond or $C_{1-3}$ alkylene), (c) —$Y^{7a}$—$X^7$—$Y^{7b}$— ($Y^{7a}$ is a bond, —O— or a methylene group; $Y^{7b}$ is a bond, —O— or a methylene group; $X^7$ is a divalent 3- to 8-membered cyclic group), or (d) —$X^8$—$Y^8$— ($X^8$ is a bond, —O—, —$NR^a$—, —S—, —SO—, —$SO_2$— or —CO—; $Y^8$ is an optionally substituted $C_{1-6}$ alkylene group or optionally substituted $C_1$—, alkylene-O—)), (2) when $L^{1b}$ and $R^3$ are bonded to form a ring optionally further substituted, the partial structural formula of the formula (I):

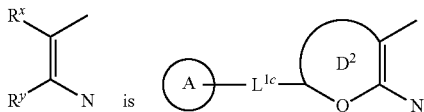

wherein ring $D^2$ is a 5- or 6-membered heterocycle optionally further substituted; and other symbols are as defined above, excluding 1-[2-fluoro-4-(1H-pyrazol-1-yl)phenyl]-5-methoxy-3-(1-phenyl-1H-pyrazol-5-yl)pyridazin-4(1H)-one, or a salt thereof.

[Item 2] A prodrug of the compound of the aforementioned item 1 or a salt thereof.

[Item 3] A medicament comprising the compound of the aforementioned item 1 or a salt thereof, or a prodrug thereof.

[Item 4] The medicament of the aforementioned item 3, which is a phosphodiesterase 10A inhibitor.

[Item 5] The medicament of the aforementioned item 3, which is a prophylactic or therapeutic drug for schizophrenia.

[Item 6] A method of preventing or treating schizophrenia, which comprises administering an effective amount of the compound of the aforementioned item 1 or a salt thereof, or a prodrug thereof to a mammal.

[Item 7] The compound of the aforementioned item 1 or a salt thereof, or a prodrug thereof for use in the prevention or treatment of schizophrenia.

[Item 8] Use of the compound of the aforementioned item 1 or a salt thereof, or a prodrug thereof for the manufacture of a prophylactic or therapeutic drug for schizophrenia.

Effect of the Invention

The compound of the present invention has a PDE inhibitory activity and is useful as a drug for preventing or treating schizophrenia.

DETAILED DESCRIPTION OF THE INVENTION

The present invention is explained in detail in the following.

In the present specification, indication of hydrogen atom in the chemical structural formulas is sometimes omitted according to the practice in the chemical field.

Unless otherwise specified, in this specification, examples of the "halogen atom" include fluorine, chlorine, bromine and iodine.

Unless otherwise specified, in this specification, the phrase "optionally halogenated" or the term "halogeno" means that one or more (e.g., 1 to 3) halogen atoms can be present as substituents.

Unless otherwise specified, in this specification, examples of the "nonaromatic hydrocarbon ring" include a nonaromatic hydrocarbon ring having a carbon number of 3-8 such as $C_{3-8}$ cycloalkane, $C_{5-8}$ cycloalkene, $C_{5-8}$ cycloalkadiene, bridged ring hydrocarbon having a carbon number of 5-8 and the like.

Unless otherwise specified, in this specification, examples of the "$C_{3-8}$ cycloalkane" include cyclopropane, cyclobutane, cyclopentane, cyclohexane, cycloheptane, and cyclooctane.

Unless otherwise specified, in this specification, examples of the "$C_{5-8}$ cycloalkene" include cyclopentene, cyclohexene, cycloheptene, and cyclooctene.

Unless otherwise specified, in this specification, examples of the "$C_{5-8}$ cycloalkadiene" include cyclopentadiene, cyclohexadiene, cycloheptadiene, and cyclooctadiene.

Unless otherwise specified, in this specification, examples of the "bridged ring hydrocarbon having a carbon number of 5-8" include bicyclo[2.1.0]pentane, bicyclo[2.2.1]heptane, bicyclo[3.2.1]octane, bicyclo[2.2.1]hept-2-ene, and tricyclo[2.2.1.0]heptane.

Unless otherwise specified, in this specification, examples of the "aromatic hydrocarbon ring" include aromatic hydrocarbon ring having a carbon number of 6-14. Concrete examples thereof include benzene ring, naphthalene ring, anthracene ring, and phenanthrene ring.

Unless otherwise specified, in this specification, the "aromatic hydrocarbon ring" may be monocyclic, bicyclic or tricyclic.

Unless otherwise specified, in this specification, examples of the "heterocycle" include a 3- to 8-membered heterocycle having 1 to 4 hetero atoms selected from a nitrogen atom, a sulfur atom and an oxygen atom.

Unless otherwise specified, in this specification, examples of the "heterocycle" include non-aromatic heterocycle, and aromatic heterocycle.

Unless otherwise specified, in this specification, examples of the "non-aromatic heterocycle" include 3- to 8-membered non-aromatic heterocycle and the like. Concrete examples thereof include oxirane ring, azetidine ring, oxetane ring, thietane ring, pyrrolidine ring, dihydrofuran ring, tetrahydrofuran ring, tetrahydrothiophene ring, imidazolidine ring, oxazolidine ring, isooxazoline ring, piperidine ring, dihydropyran ring, tetrahydropyran ring, tetrahydrothiopyran ring, morpholine ring, thiomorpholine ring, piperazine ring, dihydrooxazine ring, tetrahydrooxazine ring, dihydropyrimidine ring, tetrahydropyrimidine ring, azepane ring, oxepane ring, thiepane ring, oxazepane ring, thiazepane ring, azocane ring, oxocane ring, thiocane ring, oxazocane ring, and thiazocane ring.

Unless otherwise specified, in this specification, examples of the "aromatic heterocycle" include 5- or 6-membered aromatic heterocycle. Concrete examples thereof include furan ring, thiophene ring, pyrrole ring, oxazole ring, isoxazole ring, thiazole ring, isothiazole ring, imidazole ring, pyrazole ring, 1,2,3-oxadiazole ring, 1,2,4-oxadiazole ring, 1,3,4-oxadiazole ring, furazan ring, 1,2,3-thiadiazole ring, 1,2,4-thiadiazole ring, 1,3,4-thiadiazole ring, 1,2,3-triazole ring, 1,2,4-triazole ring, tetrazole ring, pyridine ring, pyridazine ring, pyrimidine ring, pyrazine ring, and triazine ring.

Unless otherwise specified, in this specification, examples of the "alkyl (group)" include $C_{1-6}$ alkyl (group).

Unless otherwise specified, in this specification, examples of the "$C_{1-6}$ alkyl (group)" include methyl, ethyl, propyl, isopropyl, butyl, isobutyl, sec-butyl, tert-butyl, pentyl, isopentyl, neopentyl, and hexyl.

Unless otherwise specified, in this specification, the "optionally halogenated $C_{1-6}$ alkyl (group)" means $C_{1-6}$ alkyl (group) optionally substituted by a halogen atom. Concrete examples thereof include trifluoromethyl.

Unless otherwise specified, in this specification, examples of the "alkenyl (group)" include $C_{2-6}$ alkenyl (group).

Unless otherwise specified, in this specification, examples of the "$C_{2-6}$ alkenyl (group)" include vinyl, 1-propen-1-yl, 2-propen-1-yl, isopropenyl, 2-buten-1-yl, 4-penten-1-yl, and 5-hexen-1-yl.

Unless otherwise specified, in this specification, examples of the "alkynyl (group)" include a $C_{2-6}$ alkynyl group. Examples of the "$C_{2-6}$ alkynyl (group)" include ethynyl, 1-propyn-1-yl, 2-propyn-1-yl, 4-pentyn-1-yl, and 5-hexyn-1-yl.

Unless otherwise specified, in this specification, examples of the "$C_{3-7}$ cycloalkyl-$C_{2-6}$ alkynyl (group)" include cyclopropylethynyl.

Unless otherwise specified, in this specification, examples of the "nonaromatic cyclic hydrocarbon group" include $C_{3-7}$ cycloalkyl (group), $C_{3-7}$ cycloalkenyl (group), and $C_{4-10}$ cycloalkadienyl (group), each of which may be condensed with one or more (preferably 1 or 2) hydrocarbon ring.

Examples of the "hydrocarbon ring" include the aforementioned "nonaromatic hydrocarbon ring", and the aforementioned "aromatic hydrocarbon ring".

Unless otherwise specified, in this specification, examples of the "$C_{3-7}$ cycloalkyl (group)" include cyclopropyl, cyclobutyl, cyclopentyl, cyclohexyl, and cycloheptyl.

Unless otherwise specified, in this specification, examples of the "$C_{3-7}$ cycloalkenyl (group)" include cyclopropenyl, cyclobutenyl, cyclopentenyl, cyclohexenyl, and cycloheptenyl.

Unless otherwise specified, in this specification, examples of the "$C_{4-10}$ cycloalkadienyl (group)" include cyclobutadienyl, cyclopentadienyl, cyclohexadienyl, cycloheptadienyl, cyclooctadienyl, cyclononadienyl, and cyclodecadienyl.

Unless otherwise specified, in this specification, the "aromatic cyclic hydrocarbon group" may be monocyclic, bicyclic or tricyclic.

Unless otherwise specified, in this specification, examples of the "aromatic cyclic hydrocarbon group" include $C_{6-14}$ aryl (group) and the like. Concrete examples thereof include phenyl, 1-naphthyl, 2-naphthyl, 2-biphenylyl, 3-biphenylyl, 4-biphenylyl, and 2-anthryl.

Unless otherwise specified, in this specification, examples of the "$C_{7-16}$ aralkyl (group)" include benzyl, phenethyl, diphenylmethyl, 1-naphthylmethyl, 2-naphthylmethyl, 2,2-diphenylethyl, 3-phenylpropyl, 4-phenylbutyl, 5-phenylpentyl, 2-biphenylylmethyl, 3-biphenylylmethyl, and 4-biphenylylmethyl.

Unless otherwise specified, in this specification, examples of the "$C_{6-14}$ aryl-$C_{2-6}$ alkenyl (group)" include styryl.

Unless otherwise specified, in this specification, examples of the "$C_{1-6}$ alkylene group" (that is, $C_{1-6}$ alkanediyl group) include methylene, ethylene, trimethylene, tetramethylene, 2-butenylene, 2-methyltetramethylene, pentamethylene, and hexamethylene.

Unless otherwise specified, in this specification, examples of the "$C_{1-3}$ alkylene group" include an alkylene group having a carbon number of 1-3 from the aforementioned "$C_{1-6}$ alkylene group".

Unless otherwise specified, in this specification, the "heterocyclic group" (and a heterocyclic moiety in a substituent) is a non-aromatic heterocyclic group, or an aromatic heterocyclic group (i.e., heteroaryl group).

Unless otherwise specified, in this specification, the "heterocyclic group" may be monocyclic, bicyclic or tricyclic.

Unless otherwise specified, in this specification, the "heterocyclic group" is, for example, a 3- to 14-membered heterocyclic group having 1 to 4 hetero atoms selected from an oxygen atom, a sulfur atom and a nitrogen atom, and the like.

Unless otherwise specified, in this specification, the "nonaromatic heterocyclic group" may be saturated or unsaturated.

Unless otherwise specified, in this specification, examples of the "nonaromatic heterocyclic group" include a 3- to 14-membered nonaromatic heterocyclic group.

Unless otherwise specified, in this specification, examples of the "3- to 14-membered nonaromatic heterocyclic group" include a 3- to 6-membered nonaromatic heterocyclic group having 1-4 hetero atoms selected from an oxygen atom, a sulfur atom and a nitrogen atom, which is optionally fused with a 5- or 6-membered ring.

Unless otherwise specified, in this specification, examples of the "3- to 6-membered nonaromatic heterocyclic group having 1 to 4 hetero atoms selected from an oxygen atom, a sulfur atom and a nitrogen atom" include tetrahydrofuryl, oxazolidinyl, imidazolinyl (e.g., 1-imidazolinyl, 2-imidazolinyl, 4-imidazolinyl), aziridinyl (e.g., 1-aziridinyl, 2-aziridinyl), azetidinyl (e.g., 1-azetidinyl, 2-azetidinyl), pyrrolidinyl (e.g., 1-pyrrolidinyl, 2-pyrrolidinyl, 3-pyrrolidinyl), piperidinyl (e.g., 1-piperidinyl, 2-piperidinyl, 3-piperidinyl), azepanyl (e.g., 1-azepanyl, 2-azepanyl, 3-azepanyl, 4-azepanyl), azocanyl (e.g., 1-azocanyl, 2-azocanyl, 3-azocanyl, 4-azocanyl), piperazinyl (e.g., 1,4-piperazin-1-yl, 1,4-piperazin-2-yl), diazepinyl (e.g., 1,4-diazepin-1-yl, 1,4-diazepin-2-yl, 1,4-diazepin-5-yl, 1,4-diazepin-6-yl), diazocanyl (e.g., 1,4-diazocan-1-yl, 1,4-diazocan-2-yl, 1,4-diazocan-5-yl, 1,4-diazocan-6-yl, 1,5-diazocan-1-yl, 1,5-diazocan-2-yl, 1,5-diazocan-3-yl), tetrahydropyranyl (e.g., tetrahydropyran-4-yl), morpholinyl (e.g., 4-morpholinyl), thiomorpholinyl (e.g., 4-thiomorpholinyl), 2-oxazolidinyl, dihydrofuryl, dihydropyranyl, and dihydroquinolyl, and 2,3-dihydro-1H-imidazo[1,2-a]imidazol-1-yl.

Unless otherwise specified, in this specification, examples of the "5- or 6-membered ring" include hydrocarbon ring having a carbon number of 5 or 6 (e.g., cyclopentane, cyclohexane, cyclopentene, cyclohexene, cyclopentadiene, cyclohexadiene, benzene) and 5- or 6-membered heterocycle.

Unless otherwise specified, in this specification, examples of the "5- or 6-membered heterocycle" include 5- or 6-membered ones from the aforementioned "heterocycle".

Unless otherwise specified, in this specification, examples of the "3- to 6-membered nonaromatic heterocyclic group having 1 to 4 hetero atoms selected from an oxygen atom, a sulfur atom and a nitrogen atom, which is fused with a 5- or 6-membered ring" include 2,3-dihydro-1H-imidazo[1,2-a]benzimidazol-1-yl.

Unless otherwise specified, in this specification, examples of the "aromatic heterocyclic group" include a 5- or 6-membered monocyclic aromatic heterocyclic group, and a 5- to 10-membered aromatic fused heterocyclic group.

Unless otherwise specified, in this specification, examples of the "5- or 6-membered monocyclic aromatic heterocyclic group" include a 5- or 6-membered monocyclic aromatic heterocyclic group having 1 to 4 hetero atoms selected from an oxygen atom, a sulfur atom and a nitrogen atom such as pyrrolyl (e.g., 1-pyrrolyl, 2-pyrrolyl, 3-pyrrolyl), furyl (e.g., 2-furyl, 3-furyl), thienyl (e.g., 2-thienyl, 3-thienyl), pyrazolyl (e.g., 1-pyrazolyl, 3-pyrazolyl, 4-pyrazolyl), imidazolyl (e.g., 1-imidazolyl, 2-imidazolyl, 4-imidazolyl), isoxazolyl (e.g., 3-isoxazolyl, 4-isoxazolyl, 5-isoxazolyl), oxazolyl (e.g., 2-oxazolyl, 4-oxazolyl, 5-oxazolyl), isothiazolyl (e.g., 3-isothiazolyl, 4-isothiazolyl, 5-isothiazolyl), thiazolyl (e.g., 2-thiazolyl, 4-thiazolyl, 5-thiazolyl), triazolyl (e.g., 1,2,3-triazol-4-yl, 1,2,4-triazol-3-yl), oxadiazolyl (e.g., 1,2,4-oxadiazol-3-yl, 1,2,4-oxadiazol-5-yl), thiadiazolyl (e.g., 1,2,4-thiadiazol-3-yl, 1,2,4-thiadiazol-5-yl), tetrazolyl, pyridyl (e.g., 2-pyridyl, 3-pyridyl, 4-pyridyl), pyridazinyl (e.g., 3-pyridazinyl, 4-pyridazinyl), pyrimidinyl (e.g., 2-pyrimidinyl, 4-pyrimidinyl, 5-pyrimidinyl), pyrazinyl and the like.

Unless otherwise specified, in this specification, examples of the "5- to 10-membered aromatic fused heterocyclic group" include a 5- to 10-membered aromatic fused heterocyclic group having 1 to 4 hetero atoms selected from an oxygen atom, a sulfur atom and a nitrogen atom, such as isoindolyl (e.g., 1-isoindolyl, 2-isoindolyl, 3-isoindolyl, 4-isoindolyl, 5-isoindolyl, 6-isoindolyl, 7-isoindolyl), indolyl (e.g., 1-indolyl, 2-indolyl, 3-indolyl, 4-indolyl, 5-indolyl, 6-indolyl, 7-indolyl), benzo[b]furanyl (e.g., 2-benzo[b]furanyl, 3-benzo[b]furanyl, 4-benzo[b]furanyl, 5-benzo[b]furanyl, 6-benzo[b]furanyl, 7-benzo[b]furanyl), benzo[c]furanyl (e.g., 1-benzo[c]furanyl, 4-benzo[c]furanyl, 5-benzo[c]furanyl), benzo[b]thienyl (e.g., 2-benzo[b]thienyl, 3-benzo[b]thienyl, 4-benzo[b]thienyl, 5-benzo[b]thienyl, 6-benzo[b]thienyl, 7-benzo[b]thienyl), benzo[c]thienyl (e.g., 1-benzo[c]thienyl, 4-benzo[c]thienyl, 5-benzo[c]thienyl), indazolyl (e.g., 1-indazolyl, 2-indazolyl, 3-indazolyl, 4-indazolyl, 5-indazolyl, 6-indazolyl, 7-indazolyl), benzimidazolyl (e.g., 1-benzimidazolyl, 2-benzimidazolyl, 4-benzimidazolyl, 5-benzimidazolyl), 1,2-benzoisoxazolyl (e.g., 1,2-benzisoxazol-3-yl, 1,2-benzisoxazol-4-yl, 1,2-benzisoxazol-5-yl, 1,2-benzisoxazol-6-yl, 1,2-benzisoxazol-7-yl), benzoxazolyl (e.g., 2-benzoxazolyl, 4-benzoxazolyl, 5-benzoxazolyl, 6-benzoxazolyl, 7-benzoxazolyl), 1,2-benzoisothiazolyl (e.g., 1,2-benzisothiazol-3-yl, 1,2-benzisothiazol-4-yl, 1,2-benzisothiazol-5-yl, 1,2-benzisothiazol-6-yl, 1,2-benzisothiazol-7-yl), benzothiazolyl (e.g., 2-benzothiazolyl, 4-benzothiazolyl, 5-benzothiazolyl, 6-benzothiazolyl, 7-benzothiazolyl), isoquinolyl (e.g., 1-isoquinolyl, 3-isoquinolyl, 4-isoquinolyl, 5-isoquinolyl), quinolyl (e.g., 2-quinolyl, 3-quinolyl, 4-quinolyl, 5-quinolyl, 8-quinolyl), cinnolinyl (e.g., 3-cinnolinyl, 4-cinnolinyl, 5-cinnolinyl, 6-cinnolinyl, 7-cinnolinyl, 8-cinnolinyl), phthalazinyl (e.g., 1-phthalazinyl, 4-phthalazinyl, 5-phthalazinyl, 6-phthalazinyl, 7-phthalazinyl, 8-phthalazinyl), quinazolinyl (e.g., 2-quinazolinyl, 4-quinazolinyl, 5-quinazolinyl, 6-quinazolinyl, 7-quinazolinyl, 8-quinazolinyl), quinoxalinyl (e.g., 2-quinoxalinyl, 3-quinoxalinyl, 5-quinoxalinyl, 6-quinoxalinyl, 7-quinoxalinyl, 8-quinoxalinyl), pyrazolo[1,5-a]pyridyl (e.g., pyrazolo[1,5-a]pyridin-2-yl, pyrazolo[1,5-a]pyridin-3-yl, pyrazolo[1,5-a]pyridin-4-yl, pyrazolo[1,5-a]pyridin-5-yl, pyrazolo[1,5-a]pyridin-6-yl, pyrazolo[1,5-a]pyridin-7-yl), imidazo[1,2-a]imidazolyl (e.g., imidazo[1,2-a]imidazol-1-yl, imidazo[1,2-a]imidazol-2-yl, imidazo[1,2-a]imidazol-3-yl, imidazo[1,2-a]imidazol-5-yl, imidazo[1,2-a]imidazol-6-yl), imidazo[1,2-a]pyridyl (e.g., imidazo[1,2-a]pyridin-2-yl, imidazo[1,2-a]pyridin-3-yl, imidazo[1,2-a]pyridin-5-yl, imidazo[1,2-a]pyridin-6-yl, imidazo[1,2-a]pyridin-7-yl, and imidazo[1,2-a]pyridin-8-yl), imidazo[4,5-b]pyridyl (e.g., imidazo[4,5-b]pyridin-2-yl, imidazo[4,5-b]pyridin-3-yl, imidazo[4,5-b]pyridin-6-yl, imidazo[4,5-b]pyridin-7-yl, and imidazo[4,5-b]pyridin-8-yl) and the like.

Unless otherwise specified, in this specification, examples of the "alkoxy (group)" include a $C_{1-6}$ alkoxy (group).

Unless otherwise specified, in this specification, examples of the "$C_{1-6}$ alkoxy (group)" include methoxy, ethoxy, propoxy, isopropoxy, butoxy, isobutoxy, sec-butoxy, pentyloxy and hexyloxy.

Unless otherwise specified, in this specification, examples of the "$C_{3-7}$ cycloalkyloxy (group)" include cyclopropyloxy, cyclobutyloxy, cyclopentyloxy, cyclohexyloxy.

Unless otherwise specified, in this specification, examples of the "$C_{6-14}$ aryloxy (group)" include phenyloxy, 1-naphthyloxy and 2-naphthyloxy.

Unless otherwise specified, in this specification, examples of the "$C_{7-16}$ aralkyloxy (group)" include benzyloxy and phenethyloxy.

Unless otherwise specified, in this specification, examples of the "alkyl-carbonyloxy (group)" include $C_{1-6}$ alkyl-carbonyloxy (group).

Unless otherwise specified, in this specification, examples of the "$C_{1-6}$ alkyl-carbonyloxy (group)" include acetoxy and propionyloxy.

Unless otherwise specified, in this specification, examples of the "alkoxy-carbonyloxy (group)" include $C_{1-6}$ alkoxy-carbonyloxy (group).

Unless otherwise specified, in this specification, examples of the "$C_{1-6}$ alkoxy-carbonyloxy (group)" include methoxycarbonyloxy, ethoxycarbonyloxy, propoxycarbonyloxy and butoxycarbonyloxy.

Unless otherwise specified, in this specification, examples of the "mono-alkyl-carbamoyloxy (group)" include mono-$C_{1-6}$ alkyl-carbamoyloxy (group).

Unless otherwise specified, in this specification, examples of the "mono-$C_{1-6}$ alkyl-carbamoyloxy (group)" include methylcarbamoyloxy and ethylcarbamoyloxy.

Unless otherwise specified, in this specification, examples of the "di-alkyl-carbamoyloxy (group)" include di-$C_{1-6}$ alkyl-carbamoyloxy (group).

Unless otherwise specified, in this specification, examples of the "di-$C_{1-6}$ alkyl-carbamoyloxy (group)" include dimethylcarbamoyloxy and diethylcarbamoyloxy.

Unless otherwise specified, in this specification, examples of the "$C_{1-14}$ aryl-carbonyloxy (group)" include benzoyloxy and naphthylcarbonyloxy.

Unless otherwise specified, in this specification, examples of the "mono- or di-$C_{6-14}$ aryl-carbamoyloxy (group)" include phenylcarbamoyloxy and naphthylcarbamoyloxy.

Unless otherwise specified, in this specification, examples of the heterocyclic moiety of the "heterocyclyl-oxy (group)" include those similar to the above-mentioned "heterocyclic group" are included. Specific examples of the "heterocyclyl-oxy (group)" include 3- to 14-membered heterocyclyl having 1 to 5 hetero atoms selected from a nitrogen atom, a sulfur atom and an oxygen atom-oxy (group).

Unless otherwise specified, in this specification, examples of the aromatic heterocyclic moiety of the "aromatic heterocyclyl-oxy (group)" include those similar to the "aromatic heterocyclic group" as examples of the above-mentioned "heterocyclic group". Specific examples of the "aromatic heterocyclyl-oxy (group)" include 5- to 14-membered aromatic heterocyclyl having 1 to 5 hetero atoms selected from a nitrogen atom, a sulfur atom and an oxygen atom-oxy.

Unless otherwise specified, in this specification, examples of the "$C_{1-6}$ alkylsulfonyloxy group" include methylsulfonyloxy and ethylsulfonyloxy.

Unless otherwise specified, in this specification, examples of the "halogeno $C_{1-6}$ alkylsulfonyloxy group" include halogeno methylsulfonyloxy and halogeno ethylsulfonyloxy.

Unless otherwise specified, in this specification, examples of the "alkylsulfanyl (group)" include $C_{1-6}$ alkylsulfanyl (group).

Unless otherwise specified, in this specification, examples of the "$C_{1-6}$ alkylsulfanyl (group)" include methylsulfanyl, ethylsulfanyl, propylsulfanyl, isopropylsulfanyl, butylsulfanyl, sec-butylsulfanyl, and tert-butylsulfanyl.

Unless otherwise specified, in this specification, examples of the "$C_{3-7}$ cycloalkylsulfanyl (group)" include cyclopropylsulfanyl, cyclobutylsulfanyl, cyclopentylsulfanyl and cyclohexylsulfanyl.

Unless otherwise specified, in this specification, examples of the "$C_{6-14}$ arylsulfanyl (group)" include phenylsulfanyl, 1-naphthylsulfanyl and 2-naphthylsulfanyl.

Unless otherwise specified, in this specification, examples of the "$C_{7-16}$ aralkylsulfanyl (group)" include benzylsufanyl and phenethylsulfanyl.

Unless otherwise specified, in this specification, examples of the heterocyclic moiety of the "heterocyclyl-sulfanyl (group)" include those similar to the above-mentioned "heterocyclic group". Specific examples of the "heterocyclylsulfanyl (group)" include 3- to 14-membered heterocyclyl having 1 to 5 hetero atoms selected from a nitrogen atom, a sulfur atom and an oxygen atom-sulfanyl (group).

Unless otherwise specified, in this specification, examples of the "alkyl-carbonyl (group)" include $C_{1-6}$ alkyl-carbonyl.

Unless otherwise specified, in this specification, examples of the "$C_{1-6}$ alkyl-carbonyl (group)" include acetyl, propionyl and pivaloyl.

Unless otherwise specified, in this specification, examples of the "$C_{3-7}$ cycloalkyl-carbonyl (group)" include cyclopropylcarbonyl, cyclopentylcarbonyl and cyclohexylcarbonyl.

Unless otherwise specified, in this specification, examples of the "$C_{6-14}$ aryl-carbonyl (group)" include benzoyl, 1-naphthoyl and 2-naphthoyl.

Unless otherwise specified, in this specification, examples of the "$C_{7-16}$ aralkyl-carbonyl (group)" include phenylacetyl and 3-phenylpropionyl.

Unless otherwise specified, in this specification, examples of the heterocyclic moiety of the "heterocyclyl-carbonyl (group)" include those similar to the above-mentioned "heterocyclic group". Specifically, examples thereof include 3- to 14-membered heterocyclyl having 1 to 5 hetero atoms selected from a nitrogen atom, a sulfur atom and an oxygen atom-carbonyl (group). Further, specific examples thereof include picolinoyl, nicotinoyl, isonicotinoyl, 2-thenoyl, 3-thenoyl, 2-furoyl, 3-furoyl, 1-morpholinylcarbonyl, 4-thiomorpholinylcarbonyl, aziridin-1-ylcarbonyl, aziridin-2-ylcarbonyl, azetidin-1-ylcarbonyl, azetidin-2-ylcarbonyl, pyrrolidin-1-ylcarbonyl, pyrrolidin-2-ylcarbonyl, pyrrolidin-3-ylcarbonyl, piperidin-1-ylcarbonyl, piperidin-2-ylcarbonyl, piperidin-3-ylcarbonyl, azepan-1-ylcarbonyl, azepan-2-ylcarbonyl, azepan-3-ylcarbonyl, azepan-4-ylcarbonyl, azocan-1-ylcarbonyl, azocan-2-ylcarbonyl, azocan-3-ylcarbonyl, azocan-4-ylcarbonyl, 1,4-piperazin-1-ylcarbonyl, 1,4-piperazin-2-ylcarbonyl, 1,4-diazepan-1-ylcarbonyl, 1,4-diazepan-2-ylcarbonyl, 1,4-diazepan-5-ylcarbonyl, 1,4-diazepan-6-ylcarbonyl, 1,4-diazocan-1-ylcarbonyl, 1,4-diazocan-2-ylcarbonyl, 1,4-diazocan-5-ylcarbonyl, 1,4-diazocan-6-ylcarbonyl, 1,5-diazocan-1-ylcarbonyl, 1,5-diazocan-2-ylcarbonyl and 1,5-diazocan-3-ylcarbonyl.

Unless otherwise specified, in this specification, examples of the "optionally esterified carboxy (group)" include carboxy, optionally substituted alkoxy-carbonyl, optionally substituted $C_{6-14}$ aryloxy-carbony, optionally substituted $C_{7-16}$ aralkyloxy-carbonyl, optionally substituted silyloxy-carbonyl (e.g., TMS-O—CO—, TES-O—CO—, TBS—O—CO—, TIPS—O—CO—, TBDPS—O—CO—, etc.)

Unless otherwise specified, in this specification, examples of the "alkoxy-carbonyl (group)" include "$C_{1-6}$ alkoxy-carbonyl (group)".

Unless otherwise specified, in this specification, examples of the "$C_{1-6}$ alkoxy-carbonyl (group)" include methoxycarbonyl, ethoxycarbonyl, propoxycarbonyl, and tert-butoxycarbonyl.

Unless otherwise specified, in this specification, examples of the "$C_{6-14}$ aryloxy-carbonyl (group)" include phenoxycarbonyl.

Unless otherwise specified, in this specification, examples of the "$C_{7-16}$ aralkyloxy-carbonyl (group)" include benzyloxycarbonyl and phenethyloxycarbonyl.

Unless otherwise specified, in this specification, examples of the "alkylsulfonyl (group)" include $C_{1-6}$ alkylsulfonyl (group).

Unless otherwise specified, in this specification, examples of the "$C_{1-6}$ alkylsulfonyl (group)" include methylsulfonyl and ethylsulfonyl.

Unless otherwise specified, in this specification, examples of the "$C_{3-7}$ cycloalkylsulfonyl (group)" include cyclopropylsulfonyl, cyclobutylsulfonyl, cyclopentylsulfonyl and cyclohexylsulfonyl.

Unless otherwise specified, in this specification, examples of the "$C_{6-14}$ arylsulfonyl (group)" include phenylsulfonyl, 1-naphthylsulfonyl and 2-naphthylsulfonyl.

Unless otherwise specified, in this specification, examples of the heterocyclic moiety of the "heterocyclyl-sulfonyl (group)" include those similar to the above-mentioned "heterocyclic group". Specific examples of the "heterocyclylsulfonyl (group)" include 3- to 14-membered heterocyclyl having 1 to 5 hetero atoms selected from a nitrogen atom, a sulfur atom and an oxygen atom-sulfonyl (group).

Unless otherwise specified, in this specification, examples of the "alkylsulfinyl (group)" include $C_{1-6}$ alkylsulfinyl (group).

Unless otherwise specified, in this specification, examples of the "$C_{1-6}$ alkylsulfinyl (group)" include methylsulfinyl and ethylsulfinyl.

Unless otherwise specified, in this specification, examples of the "$C_{3-7}$ cycloalkylsulfinyl (group)" include cyclopropylsulfinyl, cyclobutylsulfinyl, cyclopentylsufinyl, and cyclohexysulfinyl.

Unless otherwise specified, in this specification, examples of the "$C_{6-14}$ arylsulfinyl (group)" include phenylsulfinyl, 1-naphthylsulfinyl and 2-naphthylsulfinyl.

Unless otherwise specified, in this specification, examples of the heterocyclic moiety of the "heterocyclyl-sulfinyl (group)" include those similar to the above-mentioned "heterocyclic group". Specific examples of the "heterocyclylsulfinyl (group)" include 3- to 14-membered heterocyclyl having 1 to 5 hetero atoms selected from a nitrogen atom, a sulfur atom and an oxygen atom-sulfinyl (group).

Unless otherwise specified, in this specification, examples of the "alkyl-carbamoyl (group)" include $C_{1-6}$ alkyl-carbamoyl.

Unless otherwise specified, in this specification, examples of the "$C_{1-6}$ alkyl-carbamoyl (group)" include methylcarbamoyl, ethylcarbamoyl and propylcarbamoyl.

Unless otherwise specified, in this specification, examples of the "mono- or di-alkylamino (group)" include mono- or di-$C_{1-6}$ alkylamino (group).

Unless otherwise specified, in this specification, examples of the "mono- or di-$C_{1-6}$ alkylamino (group)" include methylamino, ethylamino, propylamino, dimethylamino and diethylamino.

Unless otherwise specified, in this specification, examples of the "alkyl-carbonylamino (group)" include $C_{1-6}$ alkyl-carbonylamino.

Unless otherwise specified, in this specification, examples of the "C$_{1-6}$ alkyl-carbonylamino (group)" include acetylamino, propionylamino and pivaloylamino.

Unless otherwise specified, in this specification, as the "heterocyclic (group)" of the "heterocyclyl-amino (group)", for example, those similar to the aforementioned "heterocyclic group" can be used. Examples of the "heterocyclylamino (group)" include 2-pyridyl-amino.

Unless otherwise specified, in this specification, as the "heterocyclyl-carbonyl" of the "heterocyclyl-carbonylamino (group)", those similar to the aforementioned "heterocyclyl-carbonyl" can be used. Examples of the "heterocyclyl-carbonylamino (group)" include pyridyl-carbonylamino.

Unless otherwise specified, in this specification, as the "heterocyclyl (group)" of the "heterocyclyl-oxycarbonylamino (group)", those similar to the aforementioned "heterocyclyl group" can be used. Examples of the "heterocyclyl-oxycarbonylamino (group)" include 2-pyridyl-oxycarbonylamino.

Unless otherwise specified, in this specification, as the "heterocyclic (group)" of the "heterocyclyl-sulfonylamino (group)", for example, those similar to the aforementioned "heterocyclic group" can be used. Examples of the "heterocyclyl-sulfonylamino (group)" include 2-pyridyl-sulfonylamino.

Unless otherwise specified, in this specification, examples of the "alkoxy-carbonylamino (group)" include C$_{1-6}$ alkoxy-carbonylamino (group).

Unless otherwise specified, in this specification, the C$_{1-6}$ alkoxy-carbonylamino (group)" include methoxycarbonylamino, ethoxycarbonylamino, propoxycarbonylamino and butoxycarbonylamino.

Unless otherwise specified, in this specification, examples of the "alkylsulfonylamino (group)" include C$_{1-6}$ alkylsulfonylamino (group).

Unless otherwise specified, in this specification, examples of the "C$_{1-6}$ alkylsulfonylamino (group)" include methylsulfonylamino and ethylsulfonylamino.

Unless otherwise specified, in this specification, examples of the "mono- or di-C$_{3-7}$ cycloalkylamino (group)" include cyclopropylamino, cyclopentylamino and cyclohexylamino.

Unless otherwise specified, in this specification, examples of the "C$_{3-7}$ cycloalkyl-carbonylamino (group)" include cyclopropylcarbonylamino, cyclopentylcarbonylamino and cyclohexylcarbonylamino.

Unless otherwise specified, in this specification, examples of the "C$_{3-7}$ cycloalkyloxy-carbonylamino (group)" include cyclopropoxycarbonylamino, cyclopentyloxycarbonylamino and cyclohexyloxycarbonylamino.

Unless otherwise specified, in this specification, examples of the "C$_{3-7}$ cycloalkylsulfonylamino (group)" include cyclopropylsulfonylamino, cyclopentylsulfonylamino and cyclohexylsulfonylamino.

Unless otherwise specified, in this specification, examples of the "mono- or di-C$_{6-14}$ arylamino (group)" include phenylamino and diphenylamino.

Unless otherwise specified, in this specification, examples of the "mono- or di-C$_{7-16}$ aralkylamino (group)" include benzylamino.

Unless otherwise specified, in this specification, examples of the "C$_{6-14}$ aryl-carbonylamino (group)" include benzoylamino and naphthoylamino.

Unless otherwise specified, in this specification, examples of the "C$_{6-14}$ arylsulfonylamino (group)" include phenylsulfonylamino, 2-naphthylsulfonylamino and 1-naphthylsulfonylamino.

[Substituent Group A]

In the present specification, substituent group A consists of the following substituents (1)-(52).
(1) halogen atom;
(2) nitro;
(3) cyano;
(4) optionally esterified carboxy group;
(5) optionally substituted alkyl group;
(6) optionally substituted alkenyl group;
(7) optionally substituted alkynyl group (e.g., optionally substituted C$_{3-7}$ cycloalkyl-C$_{2-6}$ alkynyl group);
(8) optionally substituted C$_{3-7}$ cycloalkyl group;
(9) optionally substituted C$_{6-14}$ aryl group;
(10) optionally substituted C$_{7-16}$ aralkyl group;
(11) optionally substituted C$_{6-14}$ aryl-C$_{2-6}$ alkenyl group;
(12) optionally substituted heterocyclic group;
(13) hydroxy group;
(14) optionally substituted alkoxy group;
(15) optionally substituted C$_{3-7}$ cycloalkyloxy group;
(16) optionally substituted C$_{6-14}$ aryloxy group;
(17) optionally substituted C$_{7-16}$ aralkyloxy group;
(18) optionally substituted alkyl-carbonyloxy group;
(19) optionally substituted alkoxy-carbonyloxy group;
(20) optionally substituted mono-alkyl-carbamoyloxy group;
(21) optionally substituted di-alkyl-carbamoyloxy group;
(22) optionally substituted C$_{6-14}$ aryl-carbonyloxy group;
(23) optionally substituted mono-, or di-C$_{6-14}$ aryl-carbamoyloxy group;
(24) optionally substituted heterocyclyl-oxy group (e.g., optionally substituted aromatic heterocyclyl-oxy group);
(25) optionally substituted C$_{1-6}$ alkylsulfonyloxy group (e.g., optionally substituted halogeno C$_{1-6}$ alkylsulfonyloxy group);
(26) mercapto group;
(27) optionally substituted alkylsulfanyl group;
(28) optionally substituted C$_{3-7}$ cycloalkylsulfanyl group;
(29) optionally substituted C$_{6-14}$ arylsulfanyl group;
(30) optionally substituted C$_{7-16}$ aralkylsulfanyl group;
(31) optionally substituted heterocyclyl-sulfanyl group;
(32) formyl group;
(33) optionally substituted alkyl-carbonyl group;
(34) optionally substituted C$_{3-7}$ cycloalkyl-carbonyl group;
(35) optionally substituted C$_{6-14}$ aryl-carbonyl group;
(36) optionally substituted C$_{7-16}$ aralkyl-carbonyl group;
(37) optionally substituted heterocyclyl-carbonyl group;
(38) optionally substituted alkylsulfonyl group;
(39) optionally substituted C$_{3-7}$ cycloalkylsulfonyl group;
(40) optionally substituted C$_{6-14}$ arylsulfonyl group;
(41) optionally substituted heterocyclyl-sulfonyl group;
(42) optionally substituted alkylsulfinyl group;
(43) optionally substituted C$_{3-7}$ cycloalkylsulfinyl group;
(44) optionally substituted C$_{6-14}$ arylsulfinyl group;
(45) optionally substituted heterocyclyl-sulfinyl group;
(46) sulfo group;
(47) sulfamoyl group;
(48) sulfinamoyl group;
(49) sulfenamoyl group;
(50) thiocarbamoyl group;
(51) optionally substituted carbamoyl group [e.g., optionally substituted alkyl-carbamoyl and the like]; and
(52) optionally substituted amino group
[e.g.,
amino,
optionally substituted mono-, or di-alkylamino group, optionally substituted mono-, or di-C$_{3-7}$ cycloalkylamino group, optionally substituted mono-, or di-C$_{6-14}$ arylamino group, optionally substituted mono-, or di-C$_{7-16}$ aralkylamino group, optionally substituted heterocyclyl-amino group, optionally substituted $C_{6-14}$ aryl-carbonylamino group, formylamino group, optionally substituted alkyl-carbonylamino group (e.g., mono-($C_{1-6}$ alkyl-carbonyl)-amino group), optionally substituted $C_{3-7}$ cycloalkyl-carbonylamino group, optionally substituted heterocyclyl-carbonylamino group, optionally substituted alkoxy-carbonylamino group, optionally substituted $C_{3-7}$ cycloalkyloxy-carbonylamino group, optionally substituted heterocyclyl-oxycarbonylamino group, optionally substituted carbamoylamino group, optionally substituted alkylsulfonylamino group, optionally substituted $C_{3-7}$ cycloalkylsulfonylamino group, optionally substituted heterocyclyl-sulfonylamino group, optionally substituted $C_{6-14}$ arylsulfonylamino group]

In the substituent group A, examples of each substituent of "optionally substituted alkoxy-carbonyl group", "optionally substituted alkyl group", "optionally substituted alkenyl group", "optionally substituted alkynyl group", "optionally substituted alkoxy group", "optionally substituted alkyl-carbonyloxy group", "optionally substituted alkoxy-carbonyloxy group", "optionally substituted mono-alkyl-carbamoyloxy group", "optionally substituted di-alkyl-carbamoyloxy group", "optionally substituted alkylsulfanyl group", "optionally substituted alkyl-carbonyl group", "optionally substituted alkylsulfonyl group", "optionally substituted alkylsulfinyl group", "optionally substituted alkyl-carbamoyl group", "optionally substituted mono-, or di-alkylamino group", "optionally substituted alkyl-carbonylamino group", "optionally substituted mono-($C_{1-6}$ alkyl-carbonyl)-amino group", "optionally substituted alkoxy-carbonylamino group", and "optionally substituted alkylsulfonylamino group" include those selected from the following substituent group B. The number of the substituents is 1—substitutable maximum number, more preferably 1-3, more preferably 1.

In the substituent group A, examples of each substituent of "optionally substituted $C_{6-14}$ aryloxy-carbonyl group", "optionally substituted $C_{7-16}$ aralkyloxy-carbonyl group", "optionally substituted $C_{3-7}$ cycloalkyl-$C_{2-6}$ alkynyl group", "optionally substituted $C_{3-7}$ cycloalkyl group", "optionally substituted $C_{6-14}$ aryl group", "optionally substituted $C_{7-16}$ aralkyl group", "optionally substituted $C_{6-14}$ aryl-$C_{2-6}$ alkenyl group", "optionally substituted heterocyclic group", "optionally substituted $C_{3-7}$ cycloalkyloxy group", "optionally substituted $C_{6-14}$ aryloxy group", "optionally substituted $C_{7-16}$ aralkyloxy group", "optionally substituted $C_{6-14}$ aryl-carbonyloxy group", "optionally substituted mono-, or di-$C_{6-14}$ aryl-carbamoyloxy group", "optionally substituted heterocyclyl-oxy group", "optionally substituted aromatic heterocyclyl-oxy group", "optionally substituted $C_{3-7}$ cycloalkylsulfanyl group", "optionally substituted $C_{6-14}$ arylsulfanyl group", "optionally substituted $C_{7-16}$ aralkylsulfanyl group", "optionally substituted heterocyclyl-sulfanyl group", "optionally substituted $C_{3-7}$ cycloalkyl-carbonyl group", "optionally substituted $C_{6-14}$ aryl-carbonyl group", "optionally substituted $C_{7-16}$ aralkyl-carbonyl group", "optionally substituted heterocyclyl-carbonyl group", "optionally substituted $C_{3-7}$ cycloalkylsulfonyl group", "optionally substituted $C_{6-14}$ arylsulfonyl group", "optionally substituted heterocyclyl-sulfonyl group", "optionally substituted $C_{3-7}$ cycloalkylsulfinyl group", "optionally substituted $C_{6-14}$ arylsulfinyl group", "optionally substituted heterocyclyl-sulfinyl group", "optionally substituted carbamoyl group", "optionally substituted amino group", "optionally substituted mono- or di-$C_{3-8}$ cycloalkylamino group", "optionally substituted mono- or di-$C_{6-14}$ arylamino group", "optionally substituted mono- or di-$C_{7-16}$ aralkylamino group", "optionally substituted heterocyclyl-amino group", "optionally substituted $C_{6-14}$ aryl-carbonylamino group", "optionally substituted $C_{3-8}$ cycloalkyl-carbonylamino group", "optionally substituted heterocyclyl-carbonylamino group", "optionally substituted $C_{3-8}$ cycloalkoxy-carbonylamino group", "optionally substituted heterocyclyl-oxycarbonylamino group", "optionally substituted carbamoylamino group", "optionally substituted alkylsulfonylamino group", "optionally substituted $C_{3-8}$ cycloalkylsulfonylamino group", "optionally substituted heterocyclyl-sulfonylamino group", and "optionally substituted $C_{6-14}$ arylsulfonylamino group" include those selected from the following substituent group B, and the following substituent group B'. The number of the substituents is 1—substitutable maximum number, more preferably 1-3, more preferably 1.

[Substituent Group B]

In the present specification, substituent group B consists of the following substituents (a)-(bb).

(a) halogen atom;
(b) hydroxy group;
(c) nitro group;
(d) cyano group;
(e) optionally substituted $C_{6-14}$ aryl group [e.g., $C_{6-14}$ aryl group optionally substituted by one or more (e.g., 1 to 5) substituents selected from the group consisting of halogen atom, hydroxy, cyano, amino, optionally halogenated $C_{1-6}$ alkyl, mono- or di-$C_{1-6}$ alkylamino, mono- or di-$C_{6-14}$ arylamino, mono- or di-$C_{7-16}$ aralkylamino, $C_{3-7}$ cycloalkyl, $C_{1-6}$ alkoxy, formyl, $C_{1-6}$ alkyl-carbonyl, $C_{3-7}$ cycloalkyl-carbonyl, $C_{6-14}$ aryl-carbonyl, $C_{7-16}$ aralkyl-carbonyl, $C_{1-6}$ alkoxy-carbonyl, $C_{6-14}$ aryloxy-carbonyl, $C_{7-16}$ aralkyloxy-carbonyl, $C_{1-6}$ alkylsulfanyl, $C_{1-6}$ alkylsulfinyl, $C_{1-6}$ alkylsulfonyl, carbamoyl, thiocarbamoyl, mono- or di-$C_{1-6}$ alkyl-carbamoyl, mono- or di-$C_{6-14}$ aryl-carbamoyl, etc.];

(f) optionally substituted $C_{6-14}$ aryloxy group [e.g., $C_{6-14}$ aryloxy group optionally substituted by one or more (e.g., 1 to 5) substituents selected from the group consisting of halogen atom, hydroxy, cyano, amino, optionally halogenated $C_{1-6}$ alkyl, mono- or di-$C_{1-6}$ alkylamino, mono- or di-$C_{6-14}$ arylamino, mono- or di-$C_{7-16}$ aralkylamino, $C_{3-7}$ cycloalkyl, $C_{1-6}$ alkoxy, formyl, $C_{1-6}$ alkyl-carbonyl, $C_{3-7}$ cycloalkyl-carbonyl, $C_{6-14}$ aryl-carbonyl, $C_{7-16}$ aralkyl-carbonyl, $C_{1-6}$ alkoxy-carbonyl, $C_{6-14}$ aryloxy-carbonyl, $C_{7-16}$ aralkyloxy-carbonyl, $C_{1-6}$ alkylsulfanyl, $C_{1-6}$ alkylsulfinyl, $C_{1-6}$ alkylsulfonyl, carbamoyl, thiocarbamoyl, mono- or di-$C_{1-6}$ alkyl-carbamoyl, mono- or di-$C_{6-14}$ aryl-carbamoyl, etc.];

(g) optionally substituted $C_{7-16}$ aralkyloxy group [e.g., $C_{7-16}$ aralkyloxy group optionally substituted by one or more (e.g., 1 to 5) substituents selected from the group consisting of halogen atom, hydroxy, cyano, amino, optionally halogenated $C_{1-6}$ alkyl, mono- or di-$C_{1-6}$ alkylamino, mono- or di-$C_{6-14}$ arylamino, mono- or di-$C_{7-16}$ aralkylamino, $C_{3-7}$ cycloalkyl, $C_{1-6}$ alkoxy, formyl, $C_{1-6}$ alkyl-carbonyl, $C_{3-7}$ cycloalkyl-carbonyl, $C_{6-14}$ aryl-carbonyl, $C_{7-16}$ aralkyl-carbonyl, $C_{1-6}$ alkoxy-carbonyl, $C_{6-14}$ aryloxy-carbonyl, $C_{7-16}$ aralkyloxy-carbonyl, $C_{1-6}$ alkylsulfanyl, $C_{1-6}$ alkylsulfinyl, $C_{1-6}$ alkylsulfonyl, carbamoyl, thiocarbamoyl, mono- or di-$C_{1-6}$ alkyl-carbamoyl, mono- or di-$C_{6-14}$ aryl-carbamoyl, etc.];

(h) optionally substituted mono- or di-5- to 10-membered heterocyclic group having 1-4 hetero atoms selected from a nitrogen atom, a sulfur atom, and an oxygen atom [e.g., mono- or di-5- to 10-membered heterocyclic group (e.g., furyl, pyridyl, thienyl, pyrrolidino, 1-piperidinyl, 4-piperidyl, piperazinyl, 1-morpholinyl, 4-thiomorpholinyl, azepan-1-yl, azocan-1-yl, azonan-1-yl, 3,4-dihydroisoquinolin-2-yl) having 1-4 hetero atoms selected from a nitrogen atom, a sulfur atom, and an oxygen atom, which is optionally substituted by one or more (e.g., 1 to 5) substituents selected from the group consisting of halogen atom, hydroxy, cyano, amino, optionally halogenated $C_{1-6}$ alkyl, mono- or di-$C_{1-6}$ alkylamino, mono- or di-$C_{6-14}$ arylamino, mono- or di-$C_{7-16}$ aralkylamino, $C_{3-7}$ cycloalkyl, $C_{1-6}$ alkoxy, formyl, $C_{1-6}$ alkyl-carbonyl, $C_{3-7}$ cycloalkyl-carbonyl, $C_{6-14}$ aryl-carbonyl, $C_{7-16}$ aralkyl-carbonyl, $C_{1-6}$ alkoxy-carbonyl, $C_{6-14}$ aryloxy-carbonyl, $C_{7-16}$ aralkyloxy-carbonyl, $C_{1-6}$ alkylsulfanyl, $C_{1-6}$ alkylsulfinyl, $C_{1-6}$ alkylsulfonyl, carbamoyl, thiocarbamoyl, mono- or di-$C_{1-6}$ alkyl-carbamoyl, and mono- or di-$C_{6-14}$ aryl-carbamoyl and the like];

(i) optionally substituted amino group [e.g., amino group optionally substituted by 1 or 2 substituent selected from the group consisting of $C_{1-6}$ alkyl, $C_{2-6}$ alkenyl, $C_{6-14}$ aryl, $C_{7-16}$ aralkyl, heterocyclic group, and heterocyclyl-alkyl, each of which is optionally substituted (examples of the substituent of said "$C_{1-6}$ alkyl, $C_{2-6}$ alkenyl, $C_{6-14}$ aryl, $C_{7-16}$ aralkyl, heterocyclic group and heterocyclyl-alkyl, each of which is optionally substituted" include halogen atom, hydroxy, cyano, amino, optionally halogenated $C_{1-6}$ alkyl (excluding substituent of alkyl and alkenyl), mono- or di-$C_{1-6}$ alkylamino, mono- or di-$C_{6-14}$ arylamino, mono- or di-$C_{7-16}$ aralkylamino, $C_{3-7}$ cycloalkyl, $C_{1-6}$ alkoxy, formyl, $C_{1-6}$ alkyl-carbonyl, $C_{3-7}$ cycloalkyl-carbonyl, $C_{6-14}$ aryl-carbonyl, $C_{7-16}$ aralkyl-carbonyl, $C_{1-6}$ alkoxy-carbonyl, $C_{3-7}$ cycloalkyloxy-carbonyl, $C_{6-14}$ aryloxy-carbonyl, $C_{7-16}$ aralkyloxy-carbonyl, $C_{1-6}$ alkylsulfanyl, $C_{3-7}$ cycloalkylsulfanyl, $C_{1-6}$ alkylsulfinyl, $C_{3-7}$ cycloalkylsulfinyl, $C_{1-6}$ alkylsulfonyl, $C_{3-7}$ cycloalkylsulfonyl, carbamoyl, thiocarbamoyl, mono- or di-$C_{1-6}$ alkyl-carbamoyl, mono- or di-$C_{6-14}$ aryl-carbamoyl and the like. The number of the substituents is one or more (e.g., 1-5). Examples of the "heterocyclic group" and "heterocyclyl-" of the "heterocyclyl-alkyl" include those similar to the aforementioned "heterocyclic group".];

(j) $C_{3-7}$ cycloalkyl;
(k) optionally substituted $C_{1-6}$ alkoxy group [e.g., $C_{1-6}$ alkoxy group optionally substituted by one or more (e.g., 1 to 5) substituents selected from the group consisting of halogen atom, hydroxy, amino, mono- or di-$C_{1-6}$ alkylamino, mono- or di-$C_{6-14}$ arylamino, $C_{3-7}$ cycloalkyl, $C_{1-6}$ alkoxy, formyl, $C_{1-6}$ alkyl-carbonyl, $C_{3-7}$ cycloalkyl-carbonyl, $C_{6-14}$ aryl-carbonyl, $C_{7-16}$ aralkyl-carbonyl, $C_{1-6}$ alkoxy-carbonyl, $C_{6-14}$ aryloxy-carbonyl, $C_{7-16}$ aralkyloxy-carbonyl, $C_{1-6}$ alkylsulfanyl, $C_{1-6}$ alkylsulfinyl, $C_{1-6}$ alkylsulfonyl, carbamoyl, thiocarbamoyl, mono- or di-$C_{1-6}$ alkyl-carbamoyl, and mono- or di-$C_{6-14}$ aryl-carbamoyl, trimethylsilyl (TMS) and the like];
(l) formyl group;
(m) $C_{1-6}$ alkyl-carbonyl group (e.g., acetyl and the like);
(n) $C_{3-7}$ cycloalkyl-carbonyl group;
(o) $C_{6-14}$ aryl-carbonyl group;
(p) $C_{7-16}$ aralkyl-carbonyl group;
(q) $C_{1-6}$ alkoxy-carbonyl group;
(r) $C_{6-14}$ aryloxy-carbonyl group;
(s) $C_{7-16}$ aralkyloxy-carbonyl group;
(t) $C_{1-6}$ alkylsulfanyl group;
(u) $C_{1-6}$ alkylsulfinyl group;
(v) $C_{1-6}$ alkylsulfonyl group;
(w) carbamoyl group;
(x) thiocarbamoyl group;
(y) mono-$C_{1-6}$ alkyl-carbamoyl group (e.g., methylcarbamoyl, ethylcarbamoyl and the like);
(z) di-$C_{1-6}$ alkyl-carbamoyl group (e.g., dimethylcarbamoyl, diethylcarbamoyl, ethylmethylcarbamoyl and the like);
(aa) mono-, or di-$C_{6-14}$ aryl-carbamoyl group (e.g., phenylcarbamoyl, 1-naphthylcarbamoyl, 2-naphthylcarbamoyl and the like); and (bb) mono-, or di-5- to 7-membered heterocyclyl having 1-4 hetero atoms selected from a nitrogen atom, a sulfur atom, and an oxygen atom-carbamoyl group (e.g., 2-pyridylcarbamoyl, 3-pyridylcarbamoyl, 4-pyridylcarbamoyl, 2-thienylcarbamoyl, 3-thienylcarbamoyl and the like).

[Substituent Group B']

In the present specification, substituent group B' consists of the following substituents (a)-(c).

(a) optionally substituted $C_{1-6}$ alkyl group [e.g., $C_{1-6}$ alkyl group optionally substituted by one or more (e.g., 1 to 5) substituents selected from the group consisting of halogen atom, hydroxy, cyano, amino, mono- or di-$C_{1-6}$ alkylamino, mono- or di-$C_{6-14}$ arylamino, mono- or di-$C_{7-16}$ aralkylamino, $C_{3-7}$ cycloalkyl, $C_{1-6}$ alkoxy, formyl, $C_{1-6}$ alkyl-carbonyl, $C_{3-7}$ cycloalkyl-carbonyl, $C_{6-14}$ aryl-carbonyl, $C_{7-16}$ aralkyl-carbonyl, $C_{1-6}$ alkoxy-carbonyl, $C_{6-14}$ aryloxy-carbonyl, $C_{7-16}$ aralkyloxy-carbonyl, $C_{1-6}$ alkylsulfanyl, $C_{1-6}$ alkylsulfinyl, $C_{7-6}$ alkylsulfonyl, carbamoyl, thiocarbamoyl, mono- or di-$C_{1-6}$ alkyl-carbamoyl, mono- or di-$C_{6-14}$ aryl-carbamoyl and the like];

(b) optionally substituted $C_{2-6}$ alkenyl group [e.g., $C_{2-6}$ alkenyl group optionally substituted by one or more (e.g., 1 to 5) substituents selected from the group consisting of halogen atom, hydroxy, cyano, amino, mono- or di-$C_{1-6}$ alkylamino, mono- or di-$C_{6-14}$ arylamino, mono- or di-$C_{7-16}$ aralkylamino, $C_{3-7}$ cycloalkyl, $C_{1-6}$ alkoxy, formyl, $C_{1-6}$ alkyl-carbonyl, $C_{3-7}$ cycloalkyl-carbonyl, $C_{6-14}$ aryl-carbonyl, $C_{7-16}$ aralkyl-carbonyl, $C_{1-6}$ alkoxy-carbonyl, $C_{6-14}$ aryloxy-carbonyl, $C_{7-16}$ aralkyloxy-carbonyl, $C_{1-6}$ alkylsulfanyl, $C_{1-6}$ alkylsulfinyl, $C_{1-6}$ alkylsulfonyl, carbamoyl, thiocarbamoyl, mono- or di-$C_{1-6}$ alkyl-carbamoyl, mono- or di-$C_{6-14}$ aryl-carbamoyl and the like]; and (c) optionally substituted $C_{2-6}$ alkynyl group [e.g., $C_{2-6}$ alkynyl group optionally substituted by one or more (e.g., 1 to 5) substituents selected from the group consisting of halogen atom, hydroxy, cyano, amino, mono- or di-$C_{1-6}$ alkylamino, mono- or di-$C_{6-14}$ arylamino, mono- or di-$C_{7-16}$ aralkylamino, $C_{3-7}$ cycloalkyl, $C_{1-6}$ alkoxy, formyl, $C_{1-6}$ alkyl-carbonyl, $C_{3-7}$ cycloalkyl-carbonyl, $C_{6-14}$ aryl-carbonyl, $C_{7-16}$ aralkyl-carbonyl, $C_{1-6}$ alkoxy-carbonyl, $C_{6-14}$ aryloxy-carbonyl, $C_{7-16}$ aralkyloxy-carbonyl, $C_{1-6}$ alkylsulfanyl, $C_{1-6}$ alkylsulfinyl, $C_{1-6}$ alkylsulfonyl, carbamoyl, thiocarbamoyl, mono- or di-$C_{1-6}$ alkyl-carbamoyl, mono- or di-$C_{6-14}$ aryl-carbamoyl and the like].

The symbols in the formula (I) are explained in the following.

The partial structural formula in the formula (I):

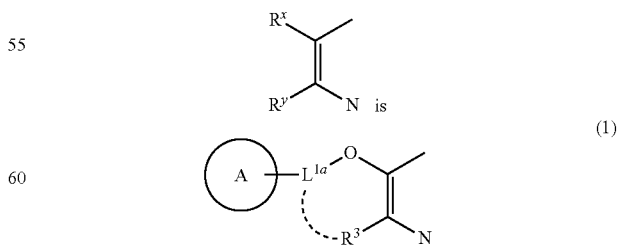

(- - - - (that is, the dotted line binding $L^{1a}$ and $R^3$) means that $L^{1a}$ and $R^3$ are optionally bonded to form a ring optionally further substituted), or

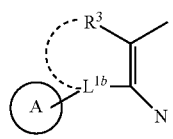

(2)

(- - - - (that is, the dotted line binding $L^{1b}$ and $R^3$) means that $L^{1b}$ and $R^3$ are optionally bonded to form a ring optionally further substituted).

That is, a compound represented by the formula (I) is

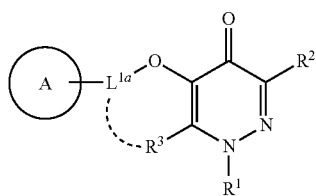

(Ia)

wherein symbols are as defined above, or

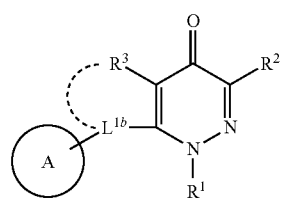

(Ib)

wherein symbols are as defined above.

The partial structural formula:

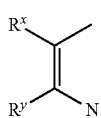

is preferably

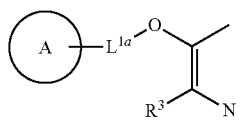

wherein symbols are as defined above.

Ring A is an optionally substituted cyclic group.

Examples of the "cyclic group" of the "optionally substituted cyclic group" for ring A include a hydrocarbon group (nonaromatic cyclic hydrocarbon group, aromatic cyclic hydrocarbon group), and a heterocyclic group (nonaromatic heterocyclic group, aromatic heterocyclic group). Of these, preferred is, for example, a heterocyclic group.

The "cyclic group" of the "optionally substituted cyclic group" for ring A is preferably bicyclic or tricyclic.

Examples of the substituent of the "optionally substituted cyclic group" for ring A include substituents selected from the aforementioned substituent group A. Preferred as the substituent is an optionally substituted alkyl group, more preferably a $C_{1-6}$ alkyl group, most preferably methyl.

The number of the substituents is preferably 0 (that is, unsubstituted), or 1-5, more preferably 0 (that is, unsubstituted).

Ring A is preferably, for example, a 3- to 14-membered (preferably, 9- to 12-membered) heterocyclic group having 1 to 4 hetero atoms selected from an oxygen atom, a sulfur atom and a nitrogen atom. Of these, a bicyclic or tricyclic heterocyclic group is preferable, and a nitrogen-containing fused heterocyclic group is most preferable.

Specific examples of ring A include 1H-benzimidazolyl, 2,3-dihydro-1H-imidazo[1,2-a]benzimidazolyl, quinolyl, imidazo[1,2-a]pyridyl, 3H-imidazo[4,5-b]pyridyl, and 1H-imidazo[1,2-a]imidazolyl.

$L^{1a}$ is
(a) a bond,
(b) —$Y^{1a}$—$X^1$—$Y^{1b}$— wherein $Y^{1a}$ is a bond, —O— or a methylene group; $Y^{1b}$ is a bond or a methylene group; $X^1$ is a divalent 3- to 8-membered cyclic group, or
(c) —$X^2$—$Y^2$— wherein $X^2$ is a bond, —O—, —$NR^a$—, —S—, —SO—, —$SO_2$— or —CO—; and $Y^2$ is an optionally substituted $C_{1-6}$ alkylene group.

While the direction of —$Y^{1a}$—$X^1$—$Y^{1b}$— and —$X^2$—$Y^2$— may be any, preferred are directions of (ring A)-$Y^{1a}$—$X^1$—$Y^{1b}$-(pyridazine ring) and (ring A)-$X^2$—$Y^2$-(pyridazine ring).

Examples of the "divalent 3- to 8-membered cyclic group" for $X^1$ include a group derived by removing two hydrogen atoms from one ring selected from the group consisting of the aforementioned "nonaromatic hydrocarbon ring having a carbon number of 3-8", a benzene ring, the aforementioned "3- to 8-membered non-aromatic heterocycle", and the aforementioned "5- or 6-membered aromatic heterocycle".

Examples of the substituent of the "optionally substituted $C_{1-6}$ alkylene group" for $Y^2$ include substituents selected from the aforementioned substituent group A.

The number of the substituents is preferably 0 (that is, unsubstituted), or 1-5.

$L^{1a}$ is preferably, for example, a $C_{1-6}$ alkylene group (e.g., methylene, ethylene, trimethylene), —O—$C_{1-6}$ alkylene- (e.g., —O-ethylene-), more preferably, for example, a $C_{1-3}$ alkylene group (e.g., methylene, ethylene, trimethylene), —O—$C_{1-3}$ alkylene- (e.g., —O-ethylene-).

$L^{1b}$ is
(a) —$Y^{3a}$—O—$Y^{3b}$— wherein $Y^{3a}$ is $C_{1-3}$ alkylene, $Y^{3b}$ is a bond or $C_{1-3}$ alkylene,
(b) —$Y^{4a}$—$X^4$—$Y^{4b}$— wherein $Y^{4a}$ is a bond, —O— or a methylene group; $Y^{4b}$ is —O— or a methylene group; $X^4$ is a divalent 3- to 8-membered cyclic group, or
(c) —$X^5$—$Y^5$— wherein $X^5$ is a bond, —O—, —$NR^a$—, —S—, —SO—, —$SO_2$— or —CO—; $Y^5$ is an optionally substituted $C_{1-6}$ alkylene group, or optionally substituted $C_{1-6}$ alkylene-O—.

$L^{1b}$ is preferably, for example, a $C_{1-6}$ alkylene group, more preferably, for example, a $C_{1-3}$ alkylene group.

While the direction of —$Y^{3a}$—O—$Y^{3b}$—, —$Y^{4a}$—$X^4$—$Y^{4b}$—, and —$X^5$—$Y^5$— may be any, preferred are directions of (ring A)-$Y^{3a}$—O—$Y^{3b}$-(pyridazine ring), (ring A)-$Y^{4a}$—$X^4$—$Y^{4b}$-(pyridazine ring), and (ring A)-$X^5$—$Y^5$-(pyridazine ring).

Examples of the "divalent 3- to 8-membered cyclic group" for $X^4$ include a group derived by removing two hydrogen atoms from one ring selected from the group consisting of the aforementioned "nonaromatic hydrocarbon ring having a carbon number of 5-7", a benzene ring, the aforementioned "3- to 8-membered non-aromatic heterocycle", and the aforementioned "5- or 6-membered aromatic heterocycle".

As the substituent of the "optionally substituted $C_{1-6}$ alkylene group" for $Y^5$, substituents selected from the aforementioned substituent group A can be mentioned.

The number of the substituents is preferably 0 (that is, unsubstituted), or 1-5.

As the substituent of the "optionally substituted $C_{1-6}$ alkylene-O—" for $Y^5$, substituents selected from the aforementioned substituent group A can be mentioned.

The number of the substituents is preferably 0 (that is, unsubstituted), or 1-5.

$R^1$ is an optionally substituted $C_{1-6}$ alkyl group or an optionally substituted cyclic group.

As the substituent of the "optionally substituted $C_{1-6}$ alkyl group" for $R^1$, substituents selected from the aforementioned substituent group A can be mentioned. The substituent is preferably a halogen atom (e.g., fluorine atom) or a $C_{3-7}$ cycloalkyl group (e.g., cyclopropyl).

The number of the substituents is preferably 0 (that is, unsubstituted), or 1-5.

Examples of the "cyclic group" of the "optionally substituted cyclic group" for $R^1$ include (1) nonaromatic cyclic hydrocarbon group (e.g., $C_{3-7}$ cycloalkyl group), (2) aromatic cyclic hydrocarbon group (e.g., $C_{6-14}$ aryl group), (3) nonaromatic heterocyclic group, and (4) aromatic heterocyclic group.

As the substituent of the "optionally substituted cyclic group" for $R^1$, substituents selected from the aforementioned substituent group A can be mentioned. The substituent is preferably an optionally substituted alkyl group, more preferably, an optionally substituted $C_{1-6}$ alkyl group, most preferably, a $C_{1-6}$ alkyl group (e.g., methyl) optionally substituted by 1 to 3 halogen atoms (e.g., fluorine atom).

The number of the substituents is preferably 0 (that is, unsubstituted), or 1-5.

$R^1$ is preferably, for example, (1) a $C_{1-6}$ alkyl group (e.g., methyl, ethyl) optionally substituted by 1 to 3 halogen atoms (e.g., fluorine atom) or one $C_{3-7}$ cycloalkyl group (e.g., cyclopropyl), (2) a $C_{3-7}$ cycloalkyl group (e.g., cyclobutyl) or (3) a $C_{6-14}$ aryl group (preferably, phenyl group) optionally substituted by $C_{1-6}$ alkyl group (e.g., methyl) substituted by 1 to 3 halogen atoms (e.g., fluorine atom).

$R^2$ is a hydrogen atom or a substituent.

Examples of the substituent for $R^2$ include substituents selected from the aforementioned substituent group A.

$R^2$ is preferably, for example, a hydrogen atom or an optionally substituted heterocyclic group, more preferably, for example, a hydrogen atom or a 5- or 6-membered monocyclic aromatic heterocyclic group (preferably, pyrazolyl) containing 1-4 hetero atoms selected from an oxygen atom, a sulfur atom and a nitrogen atom, which is optionally substituted by one or more (preferably one) substituents selected from a $C_{1-6}$ alkyl group (preferably, methyl) and a $C_{6-14}$ aryl group (preferably, phenyl group).

$R^3$ is a hydrogen atom or a substituent.

Examples of the substituent for $R^3$ include substituents selected from the aforementioned substituent group A.

$R^3$ is preferably, for example, a hydrogen atom.

In the formula (I), when $L^{1a}$ and $R^3$ are bonded to form a ring optionally further substituted, the partial structural formula of the formula (I):

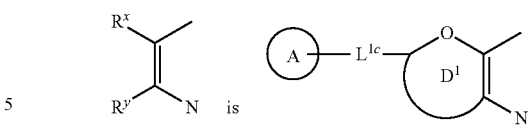

wherein
ring $D^1$ is a 5- or 6-membered heterocycle optionally further substituted,
ring A is as defined above,
$L^{1c}$ is
(a) a bond,
(b) —$Y^{6a}$—O—$Y^{6b}$— ($Y^{6a}$ is $C_{1-3}$ alkylene, and $Y^{6b}$ is a bond or $C_{1-3}$ alkylene),
(c) —$Y^{7a}$—$X^7$—$Y^{7b}$— ($Y^{7a}$ is a bond, —O— or a methylene group; $Y^{7b}$ is a bond, —O— or a methylene group; and $X^7$ is a divalent 3- to 8-membered cyclic group), or
(d) —$X^8$—$Y^8$— ($X^8$ is a bond, —O—, —$NR^a$—, —S—, —SO—, —$SO_2$— or —CO—; and $Y^8$ is an optionally substituted $C_{1-6}$ alkylene group or optionally substituted $C_{1-6}$ alkylene-O—)).

While the direction of —$Y^{6a}$—$Y^{6b}$—, —$Y^{7a}$—$X^7$—$Y^{7b}$—, and —$X^8$—$Y^8$— may be any, preferred are directions of (ring A)-$Y^{6a}$—O—$Y^{6b}$-(pyridazine ring), (ring A)-$Y^{7a}$—$X^7$—$Y^{7b}$-(pyridazine ring), and (ring A)-$X^8$—$Y^8$-(pyridazine ring).

Examples of the "5- or 6-membered heterocycle" of the "5- or 6-membered heterocycle optionally further substituted" for ring $D^1$ include those mentioned above.

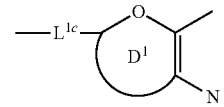

is preferably

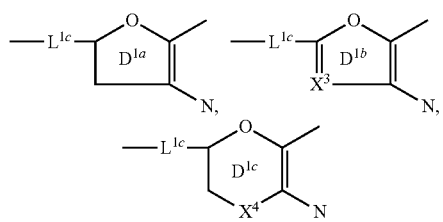

wherein
ring $D^{1a}$-ring DC may be further substituted,
$X^3$ is —CH= or —N=, and
$X^4$ is an optionally substituted methylene group, —$NR^b$— ($R^b$ is a hydrogen atom or a substituent) or —O—.

Examples of the substituent for $R^b$ include substituents selected from the aforementioned substituent group A.

Examples of the further substituent (i.e., substituent other than ring A-$L^{1c}$-) of the "5- or 6-membered heterocycle optionally further substituted" for ring $D^1$ include substituents selected from the aforementioned substituent group A.

The number of the substituents is preferably 0 (that is, unsubstituted), or 1-5.

Examples of the "divalent 3- to 8-membered cyclic group" for $X^7$ include a group derived by removing two hydrogen atoms from one ring selected from the group consisting of the aforementioned "nonaromatic hydrocarbon ring having a carbon number of 5-7", a benzene ring, the aforementioned "nonaromatic hydrocarbon ring having a carbon number of 3-8", and the aforementioned "5- or 6-membered aromatic heterocycle".

$L^{1c}$ is
(a) a bond,
(b) —$Y^{6a}$—O—$Y^{6b}$— ($Y^{6a}$ is $C_{1-3}$ alkylene, and $Y^{6b}$ is a bond or $C_{1-3}$ alkylene),
(c) —$Y^{7a}$—$X^7$—$Y^{7b}$— ($Y^{7a}$ is a bond, —O— or a methylene group; $Y^{7b}$ is a bond, —O— or a methylene group; and $X^7$ is a divalent 3- to 8-membered cyclic group), or
(d) —$X^8$—$Y^8$— ($X^8$ is a bond, —O—, —$NR^a$—, —S—, —SO—, —$SO_2$— or —CO—; and $Y^8$ is an optionally substituted $C_{1-6}$ alkylene group or an optionally substituted $C_{1-6}$ alkylene-O—).

In the formula (I), when $L^{1b}$ and $R^3$ are bonded to form a ring optionally further substituted, the partial structural formula of the formula (I):

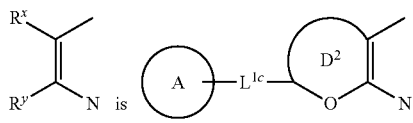

wherein ring $D^2$ is a 5- or 6-membered heterocycle further optionally substituted; and other symbols are as defined above.

Examples of the "5- or 6-membered heterocycle" of the "5- or 6-membered heterocycle further optionally substituted" for ring $D^2$ include those mentioned above.

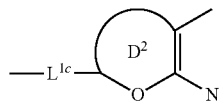

is preferably

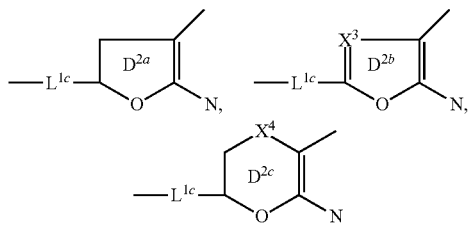

wherein
ring $D^{2a}$-ring $D^{2c}$ may be further substituted,
$X^3$ is —CH= or —N=,
$X^4$ is an optionally substituted methylene group, —$NR^b$— ($R^b$ is a hydrogen atom or a substituent) or —O—.

Examples of the substituent for $R^b$ include substituents selected from the aforementioned substituent group A.

Examples of the further substituent (i.e., substituent other than ring A-$L^{1c}$-) of the "5- or 6-membered heterocycle optionally further substituted" for ring $D^2$ include substituents selected from the aforementioned substituent group A.

The number of the substituents is preferably 0 (that is, unsubstituted), or 1-5.

Preferable examples of the substituent, moiety, ring and the like explained in the present specification are more preferably used in combination.

As compound (I), preferred is, for example, the following compound (I-A).
[Compound (I-A)]
A compound represented by the formula (I-A):

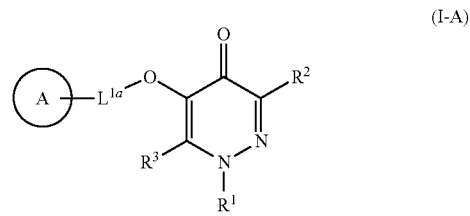

wherein
ring A is a 3- to 14-membered heterocyclic group containing 1-4 hetero atoms selected from an oxygen atom, a sulfur atom and a nitrogen atom,
$L^{1a}$ is a $C_{1-6}$ alkylene group,
$R^1$ is a $C_{1-6}$ alkyl group optionally substituted by one $C_{3-7}$ cycloalkyl group or $C_{6-14}$ aryl group,
$R^2$ is a 5- or 6-membered monocyclic aromatic heterocyclic group containing 1-4 hetero atoms selected from an oxygen atom, a sulfur atom and a nitrogen atom, which is optionally substituted by one or more substituents selected from $C_{1-6}$ alkyl group and $C_{6-14}$ aryl group, and
$R^3$ is a hydrogen atom,
or a salt thereof.

In another embodiment of the present invention, as compound (I), a compound wherein
the partial structural formula:

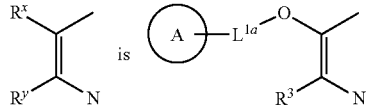

ring A is 1H-benzimidazolyl, 2,3-dihydro-1H-imidazo[1,2-a]benzimidazolyl, quinolyl, imidazo[1,2-a]pyridyl, 3H-imidazo[4,5-b]pyridyl or 1H-imidazo[1,2-a]imidazolyl;
$L^{1a}$ is a $C_{1-6}$ alkylene group (e.g., methylene, ethylene, trimethylene) or —O—$C_{1-6}$ alkylene- (e.g., —O-ethylene-);
$R^1$ is preferably, for example, (1) a $C_{1-6}$ alkyl group (e.g., methyl, ethyl) optionally substituted by 1 to 3 halogen atoms (e.g., fluorine atom) or one $C_{3-7}$ cycloalkyl group (e.g., cyclopropyl), (2) a $C_{3-7}$ cycloalkyl group (e.g., cyclobutyl) or (3) a $C_{6-14}$ aryl group (e.g., phenyl) optionally substituted by $C_{1-6}$ alkyl group (e.g., methyl) substituted by 1 to 3 halogen atoms (e.g., fluorine atom);
$R^2$ is a hydrogen atom or a 5- or 6-membered monocyclic aromatic heterocyclic group (e.g., pyrazolyl) containing 1-4 hetero atoms selected from an oxygen atom, a sulfur atom and a nitrogen atom, which is optionally substituted by one or more (e.g., one) substituents selected from $C_{1-6}$ alkyl group (e.g., methyl) and $C_{6-14}$ aryl group (e.g., phenyl); and
$R^3$ is a hydrogen atom
is preferable.

As compound (I), the compounds of Example 1-27 can be specifically mentioned, of which
5-[2-(2,3-dihydro-1H-imidazo[1,2-a]benzimidazol-1-yl)ethoxy]-1-methyl-3-(1-phenyl-1H-pyrazol-5-yl)pyridazin-4(1H)-one or a salt thereof (Example 2);

1-(cyclopropylmethyl)-5-[3-(1-methyl-1H-benzimidazol-2-yl)propoxy]-3-(1-phenyl-1H-pyrazol-5-yl)pyridazin-4(1H)-one or a salt thereof (Example 3);

1-(cyclopropylmethyl)-5-[2-(2,3-dihydro-1H-imidazo[1,2-a]benzimidazol-1-yl)ethoxy]-3-(1-phenyl-1H-pyrazol-5-yl)pyridazin-4(1H)-one or a salt thereof (Example 4);

5-(3-imidazo[1,2-a]pyridin-2-ylpropoxy)-1-methyl-3-(1-phenyl-1H-pyrazol-5-yl)pyridazin-4(1H)-one or a salt thereof (Example 11); and 1-cyclobutyl-5-[2-(2,3-dihydro-1H-imidazo[1,2-a]benzimidazol-1-yl)ethoxy]-3-(1-phenyl-1H-pyrazol-5-yl)pyridazin-4(1H)-one or a salt thereof (Example 22) are preferable.

When the compound (I) is a salt, for example, metal salts, ammonium salts, salts with organic bases, salts with inorganic acids, salts with organic acids, salts with basic or acidic amino acids can be included. Preferable examples of metal salts, for example, include alkali metal salts such as sodium salts, potassium salts and the like; alkali earth metal salts such as calcium salts, magnesium salts, barium salts and the like; and aluminum salts. Preferable examples of salts with organic bases include salts with trimethylamine, triethylamine, pyridine, picoline, 2,6-lutidine, ethanolamine, diethanolamine, triethanolamine, cyclohexylamine, dicyclohexylamine, N,N'-dibenzylethylenediamine and the like. Preferable examples of salts with inorganic acids include salts with hydrochloric acid, hydrobromic acid, nitric acid, sulfuric acid, phosphoric acid and the like. Preferable examples of salts with organic acids include salts with formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid, p-toluenesulfonic acid and the like. Preferable examples of salts with basic amino acids include salts with arginine, lysine, ornithine and the like. Preferable examples of salts with acidic amino acids include salts with aspartic acid, glutamic acid and the like. Among them, salts that are pharmaceutically acceptable are preferable. For example, in the case when acidic functional group are present in the compound, for example, inorganic salts including alkali metal salts (e.g., sodium salts, potassium salt, etc.) and alkali earth metal salts (e.g., calcium salts, magnesium salts, barium salts, etc.) and ammonium salts are preferable. In the case when basic functional group are present in the compound, for example, salts with inorganic acids such as hydrochloric acid, hydrobromic acid, nitric acid, sulfuric acid, phosphoric acid, etc. or salts with organic acid such as acetic acid, phthalic acid, fumaric acid, oxalic acid, tartaric acid, maleic acid, citric acid, succinic acid, methanesulfonic acid, p-toluenesulfonic acid, etc. are preferable.

If the compound (I) includes isomers such as tautomers, optical isomers, stereoisomers, position isomers and rotational isomers, one of the other isomers or mixture are also included in the compound of the present invention. Further, if the compound (I) has an optical isomer, the optical isomer separated from the racemate is included in the compound (I).

The compound (I) can be obtained in the crystal form. Either single crystalline form or crystalline mixture can be included in the compound (I).

The compound (I) can be a pharmaceutically acceptable co-crystal or a co-crystal salt. The co-crystal or co-crystal salt as used herein means a crystalline material composed of two or more unique solids at room temperature, each of which has distinctive physical characteristics such as structure, melting point, and heats of fusion, hygroscopicity, solubility, and stability. A co-crystal or a co-crystal salt can be produced according to a per se known co-crystallization method.

The compound (I) may be a solvate (e.g., hydrate) or a non-solvate and both are included in the compound (I).

Compounds labeled with or substituted by isotopes (e.g., $^2$H, $^3$H, $^{11}$C, $^{14}$C, $^{18}$F, $^{35}$S, $^{125}$I, etc.) are also included in compound (I). Compound (I) labeled with or substituted by isotopes can be used as, for example, a tracer used for Positron Emission Tomography (PET) (PET tracer), and are useful in the field of medical diagnosis and the like.

[Production Method]

The production methods of compound (I), and compound (1a), compound (1b) and compound (1c) encompassed in compound (I) are described below.

Compound (I) can be produced by a method known per se, for example, the production method shown by reaction scheme 1 to be described in detail in the following or a method analogous thereto.

In each of the following production methods, each starting compound used for the production of compound (I) may form a salt. Examples of such salt include those similar to the salts of compound (I) can be mentioned.

In addition, each starting compound used for the production of compound (I) can be used directly in the form of a reaction mixture or as a crude product in the following reactions. However, it can be isolated from the reaction mixture according to the ordinary method. The product itself can be easily purified by the known means of isolation such as extraction, concentration, neutralization, filtration, distillation, recrystallization and chromatography. Examples of the solvent used for the above-mentioned recrystallization include water, alcohols, ethers, hydrocarbons, amides, halogenated hydrocarbons, nitriles, ketones, esters, sulfoxides, organic acids and the like can be mentioned. These solvents can be used singly, or two or more kinds of the solvents may be used at a suitable mixing ratio, for example, 1:1-1:10. Alternatively, when the compound in the schemes is commercially available, a commercial product can be used directly and in addition, those which are manufactured by the known methods or by a comparable method can be used.

When the substituents that compound (I) have include a convertible functional group (e.g., carboxyl group, amino group, hydroxyl group, carbonyl group, mercapto group, $C_{1-6}$ alkoxy-carbonyl group, $C_{6-14}$ aryloxy-carbonyl group, $C_{7-16}$ aralkyloxy-carbonyl group, sulfo group, halogen atom etc.), various compounds can be produced by converting such functional group by a method known per se or a method analogous thereto.

When it is a carboxyl group, for example, it can be converted by reactions such as esterification, reduction, amidation, conversion reaction to optionally protected amino group and the like.

When it is a amino group, for example, it can be converted by reactions such as amidation, sulfonylation, nitrosation, alkylation, arylation, imidation and the like.

When it is a hydroxyl group, for example, it can be converted by reactions such as esterification, carbamoylation, sulfonylation, alkylation, arylation, oxidation, halogenation and the like.

When it is a carbonyl group, for example, it can be converted by reactions such as reduction, oxidation, imination (including oximation, hydrazonation), (thio)ketalation, alkylidenation, thiocarbonylation and the like.

When it is a mercapto group, for example, it can be converted by reactions such as alkylation, oxidation and the like.

When it is a $C_{1-6}$ alkoxy-carbonyl group, $C_{6-14}$ aryloxy-carbonyl group, or $C_{7-16}$ aralkyloxy-carbonyl group, for example, it can be converted by reactions such as reduction, hydrolysis and the like.

When it is a sulfo group, for example, it can be converted by reactions such as sulfonamidation, reduction and the like.

When it is a halogen atom, for example, it can be converted by various nucleophilic substitution reactions, various coupling reactions and the like.

In each of the aforementioned reactions, when the compound is obtained in a free form, it may be converted to a salt by a conventional method, and when it is obtained as a salt, it can also be converted to a free form or other salt by a conventional method.

These functional groups can be converted according to a method known per se, for example, the method described in "Comprehensive Organic Transformations" (by Richard C. Larock, published in 1999 by Wiley-VCH).

In each reaction in the production method of compound (I) and each reaction in the synthesis of the starting compound, when the starting compound has an amino group, a carboxy group, or a hydroxy group as a substituent, a protecting group generally used in the peptide chemistry and the like may be introduced into these groups, and the object compound can be obtained by eliminating the protecting group as necessary after the reaction.

As the amino-protecting group, formyl group, or $C_{1-6}$ alkyl-carbonyl group (e.g., acetyl, ethylcarbonyl etc.), phenylcarbonyl group, $C_{1-6}$ alkyl-oxycarbonyl group (e.g., methoxycarbonyl, ethoxycarbonyl, tert-butoxycarbonyl (Boc) etc.), allyloxycarbonyl (Alloc) group, phenyloxycarbonyl group, fluorenylmethoxycarbonyl (Fmoc) group, $C_{7-10}$ aralkyl-carbonyl group (e.g., benzylcarbonyl etc.), $C_{7-10}$ aralkyl-oxycarbonyl group (e.g., benzyloxycarbonyl (Z) etc.), $C_{7-10}$ aralkyl group (e.g., benzyl etc.), 2-(trimethylsilyl) ethoxymethyl (SEM) group, trityl group, phthaloyl group or N,N-dimethylaminomethylene group, each of which optionally has substituent(s), and the like are used. As these substituents, phenyl group, halogen atom (e.g., fluorine, chlorine, bromine, iodine etc.), $C_{1-6}$ alkyl-carbonyl group (e.g., methylcarbonyl, ethylcarbonyl, butylcarbonyl etc.), nitro group and the like are used, wherein the number of substituents is about 1-3.

As the carboxyl-protecting group, $C_{1-6}$ alkyl group (e.g., methyl, ethyl, n-propyl, isopropyl, n-butyl, tert-butyl etc.), allyl group, benzyl group, phenyl group, trityl group or trialkylsilyl group, each of which optionally has substituent(s), and the like are used. As these substituents, halogen atom (e.g., fluorine, chlorine, bromine, iodine etc.), formyl group, $C_{1-6}$ alkyl-carbonyl group (e.g., acetyl, ethylcarbonyl, butylcarbonyl etc.), nitro group and the like are used, wherein the number of substituents is about 1-3.

As the hydroxyl-protecting group, $C_{1-6}$ alkyl group (e.g., methyl, ethyl, n-propyl, isopropyl, n-butyl, tert-butyl etc.), $C_{7-10}$ aralkyl group (e.g., benzyl etc.), formyl group, $C_{1-6}$ alkyl-carbonyl group (e.g., acetyl, ethylcarbonyl etc.), benzoyl group, $C_{7-10}$ aralkyl-carbonyl group (e.g., benzylcarbonyl etc.), tetrahydropyranyl group, furanyl group or silyl group, each of which optionally has substituent(s), and the like are used. As these substituents, halogen atom (e.g., fluorine, chlorine, bromine, iodine etc.), $C_{1-6}$ alkyl group (e.g., methyl, ethyl, n-propyl etc.), phenyl group, $C_{7-10}$ aralkyl group (e.g., benzyl etc.), $C_{1-6}$ alkoxy group (e.g., methoxy, ethoxy, n-propoxy etc.), nitro group and the like are used, wherein the number of substituents is about 1-4.

These protecting groups can be introduced or removed by a method known per se, for example, the method described in Protective Groups in Organic Synthesis, $3^{rd}$ Ed. (Theodora W. Greene, Peterg. M. Wuts), Wiley-Interscience (1999) and the like.

When compound (I) is present as a configurational isomer, a diastereomer, a conformer and the like, each can be isolated by a known means. When compound (I) is an optical isomer, racemates can be resolved by a general optical resolution means, whereby an optically active forms ((+) form, (−) form) can be obtained.

When compound (I) has an optical isomer, a stereoisomer, a positional isomer, a rotamer or a tautomer, these are also encompassed in compound (I), and can be obtained as a single product according to synthesis and separation methods known per se.

For example, the method of optical resolution may be a method known per se, such as a fractional recrystallization method, a chiral column method, a diastereomer method etc.
1) Fractional Recrystallization Method A method wherein a salt of a racemate with an optically active compound (e.g., (+)-mandelic acid, (−)-mandelic acid, (+)-tartaric acid, (−)-tartaric acid, (+)-1-phenethylamine, (−)-1-phenethylamine, cinchonine, (−)-cinchonidine, brucine etc.) is formed, which is separated by a fractional recrystallization method, and if desired, a neutralization step to give a free optical isomer.
2) Chiral Column Method A method wherein a racemate or a salt thereof is applied to a column for separation of an optical isomer (a chiral column) to allow separation. In the case of a liquid chromatography, for example, a mixture of the optical isomers is applied to a chiral column such as ENALTIO-OVM (manufactured by Tosoh Corporation), CHIRAL series (manufactured by Daicel Chemical Industries, Ltd.) and the like, and developed with water, various buffers (e.g., phosphate buffer, etc.) and organic solvents (e.g., ethanol, methanol, isopropanol, acetonitrile, trifluoroacetic acid, diethylamine etc.), solely or as a mixed solution thereof to separate the optical isomer. In the case of a gas chromatography, for example, a chiral column such as CP-Chirasil-DeX CB (manufactured by GL Sciences Inc.) and the like is used to allow separation.
3) Diastereomer Method A method wherein a racemic mixture is prepared into a diastereomeric mixture by chemical reaction with an optically active reagent, which is made into a single substance by a typical separation means (e.g., a fractional recrystallization method, a chromatography method etc.) and the like, and is subjected to a chemical treatment such as hydrolysis and the like to separate an optically active reagent moiety, whereby an optical isomer is obtained. For example, when compound (I) contains hydroxy group, or primary or secondary amino group within a molecule, the compound and an optically active organic acid (e.g., MTPA [α-methoxy-α-(trifluoromethyl)phenylacetic acid], (−)-menthoxyacetic acid etc.) and the like are subjected to condensation reaction to give diastereomers of the ester compound or the amide compound, respectively. When compound (I) has a carboxyl group, this compound and an optically active amine or an optically active alcohol reagent are subjected to condensation reaction to give diastereomers of the amide compound or the ester compound, respectively. The separated diastereomer is converted to an optical isomer of the original compound by acid hydrolysis or base hydrolysis.

The salt of compound (I) can be produced by a method known per se. For example, when compound (I) is a basic compound, the salt can be produced by adding an inorganic acid or an organic acid, and when compound (I) is an acidic compound, the salt can be produced by adding an organic base or an inorganic base.

The solvents, acids and bases used in the production method of the compound of the present invention are explained below.

Examples of the "solvent" include "alcohols", "ethers", "hydrocarbons", "amides", "halogenated hydrocarbons", "nitriles", "ketones", "esters", "sulfoxides" and the like.

Examples of the "alcohols" include methanol, ethanol, 1-propanol, 2-propanol, tert-butyl alcohol and the like.

Examples of the "ethers" include diethyl ether, diisopropyl ether, diphenyl ether, tetrahydrofuran, 1,4-dioxane, 1,2-dimethoxyethane and the like.

Examples of the "hydrocarbons" include benzene, toluene, cyclohexane, hexane and the like.

Examples of the "amides" include N,N-dimethylformamide, N,N-dimethylacetamide, N-methylpyrrolidine, hexamethylphosphoric triamide and the like.

Examples of the "halogenated hydrocarbons" include dichloromethane, chloroform, carbon tetrachloride, 1,2-dichloroethane, chlorobenzene and the like.

Examples of the "nitriles" include acetonitrile, propionitrile and the like.

Examples of the "ketones" include acetone, ethyl methyl ketone and the like.

Examples of the "esters" include ethyl acetate and the like.

Examples of the "sulfoxides" include dimethyl sulfoxide and the like.

Examples of the "acid" include "organic acids", "mineral acids", "Lewis acids" and the like.

Examples of the "organic acids" include formic acid, acetic acid, propionic acid, trifluoroacetic acid, citric acid, methanesulfonic acid, p-toluenesulfonic acid and the like.

Examples of the "mineral acids" include hydrochloric acid, sulfuric acid and the like.

Examples of the "Lewis acids" include boron trichloride, boron tribromide and the like.

Examples of the "base" include "basic salts", "aromatic amines", "tertiary amines", "alkali metal hydrides", "alkali metals", "metal amides", "alkyl metals", "aryl metals", "metal alkoxides" and the like.

Examples of the "inorganic bases" include sodium hydroxide, potassium hydroxide, lithium hydroxide, barium hydroxide and the like.

Examples of the "basic salts" include sodium carbonate, potassium carbonate, cesium carbonate, sodium hydrogen carbonate, sodium acetate, ammonium acetate and the like.

Examples of the "aromatic amines" include pyridine, lutidine and the like.

Examples of the "tertiary amines" include triethylamine, tripropylamine, tributylamine, diisopropylethylamine, cyclohexyldimethylamine, 4-dimethylaminopyridine, N,N-dimethylaniline, N-methylpiperidine, N-methylpyrrolidine, N-methylmorpholine, 1,8-diazabicyclo[5,4,0]undec-7-ene and the like.

Examples of the "alkali metal hydrides" include sodium hydride, potassium hydride and the like.

Examples of the "alkali metals" include sodium, lithium, potassium and the like.

Examples of the "metal amides" include sodium amide, lithium diisopropylamide, lithium hexamethyldisilazide and the like.

Examples of the "alkyl metals" include butyllithium, sec-butyllithium, tert-butyllithium and the like.

Examples of the "aryl metals" include phenyllithium and the like.

Examples of the "metal alkoxides" include sodium methoxide, sodium ethoxide, sodium tert-butoxide, potassium tert-butoxide and the like.

In compound (I), compound (1a) wherein the partial structural formula

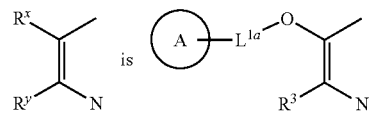

is wherein each symbol is as defined above, and compound (1b) wherein

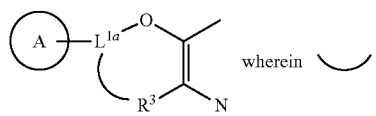

wherein (i.e., the circular arc binding $L^{1a}$ and $R^3$) means that $L^{1a}$ and $R^3$ are bonded to form an optionally substituted ring, and other symbols are each as defined above, can be produced by, for example, the method shown by the following reaction scheme 1 or a method analogous thereto.

Reaction scheme 1

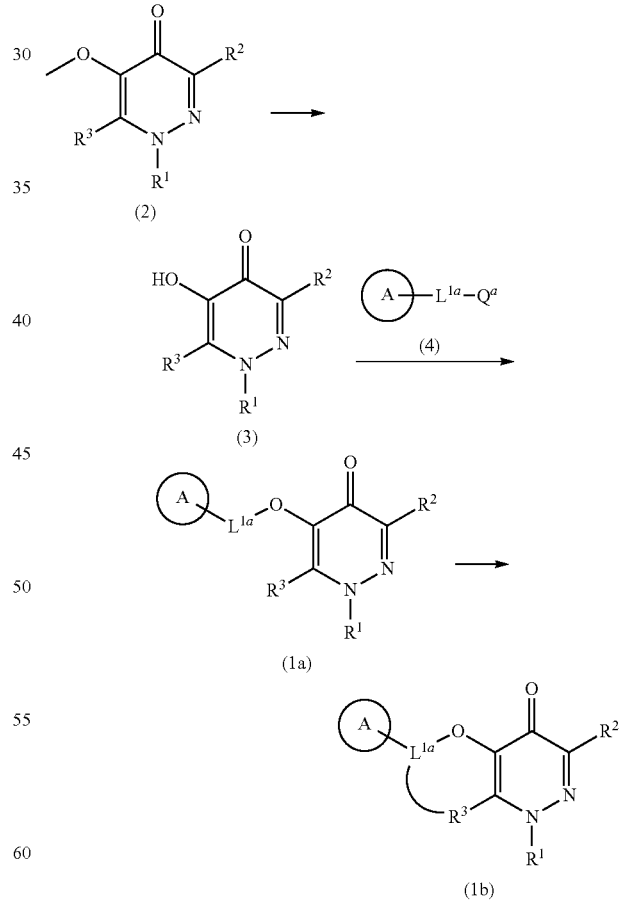

wherein $Q^a$ is a leaving group or a hydroxyl group, and other symbols are as defined above.

Examples of the leaving group for $Q^a$ include a halogen atom (e.g., chlorine, bromine, iodine), an optionally halogenated $C_{1-6}$ alkylsulfonyloxy group (e.g., methylsulfonyloxy, ethylsulfonyloxy, trifluoromethylsulfonyloxy), a $C_{6-10}$ arylsulfonyloxy group optionally substituted by a $C_{1-6}$ alkyl group (e.g., benzenesulfonyloxy, p-toluenesulfonyloxy), a methanesulfonyl group and the like, with preference given to a halogen atom and an optionally halogenated $C_{1-6}$ alkylsulfonyloxy group.

Compound (2) can be produced by a method known per se or a method analogous thereto, the method shown in the following reaction scheme 2 or 3, or a method analogous thereto.

Compound (3) can be produced by reacting trimethylsilyl chloride with compound (2) in the presence of sodium iodide. Sodium iodide is used in about 1-10 mol, preferably 1-5 mol, per 1 mol of compound (2). Trimethylsilyl chloride is used in about 1-10 mol, preferably 1-5 mol, per 1 mol of compound (2).

While the solvent is not particularly limited as long as the reaction proceeds, for example, nitriles are preferable. The reaction is desirably performed generally at room temperature or under heating under reflux conditions, with preference given to with heating under reflux. The reaction time is generally 1-20 hr, preferably 3-10 hr.

Compound (4) may be a commercially available product, or can be produced by a method known per se or a method analogous thereto.

Compound (1a) can be produced by reacting compound (3) with compound (4).

In the reaction, compound (4) is used in an amount of generally about 1-10 mol, preferably 1-3 mol, per 1 mol of compound (3).

When $Q^a$ is a leaving group, this reaction is generally performed in the presence of a base. Examples of the base include inorganic bases, basic salts, aromatic amines, tertiary amines, alkali metal hydrides, metal amides, alkyl metals, aryl metals, metal alkoxides and the like. Such base is used in an amount of generally about 1-10 mol, preferably 1-3 mol, per 1 mol of compound (3).

This reaction can be performed in the presence of an iodide salt when desired. Examples of the iodide salt include sodium iodide and potassium iodide and the like. Such iodide salt is used in an amount of generally about 0.1-5 mol, preferably 1-3 mol, per 1 mol of compound (3).

This reaction is advantageously performed by using a solvent inert to the reaction. While such solvent is not particularly limited as long as the reaction proceeds, for example, solvents such as ethers, hydrocarbons, amides, halogenated hydrocarbons, sulfoxides and the like, a mixed solvent thereof and the like are preferable.

The reaction temperature is generally room temperature $-200°$ C., preferably room temperature $-100°$ C.

While the reaction time varies depending on the reagent and solvent to be used, it is generally 0.5-48 hr, preferably 1-20 hr.

When $Q^a$ is a hydroxyl group, this reaction is generally performed in the presence of a phosphorus reagent and a Mitsunobu reagent. Examples of the phosphorus reagent include triphenylphosphine and the like. Examples of the Mitsunobu reagent include diethyl azodicarboxylate, diisopropyl azodicarboxylate, di-tert-butyl diazene-1,2-dicarboxylate and the like. Such compound is used in an amount of generally about 1-10 mol, preferably 1-3 mol, per 1 mol of compound (3).

This reaction is advantageously performed by using a solvent inert to the reaction. While such solvent is not particularly limited as long as the reaction proceeds, for example, solvents such as ethers, hydrocarbons, amides and the like, a mixed solvent thereof and the like are preferable.

The reaction temperature is generally $-78$ to $100°$ C., preferably $-10$ to $50°$ C.

While the reaction time varies depending on the reagent and solvent to be used, it is generally 5 min-2 hr, preferably 10 min-1 hr.

When both $R^3$ and $L^{1a}$ have a convertible functional group, compound (1b) can be produced by reacting them by a method known per se or a method analogous thereto to construct a ring. Examples of the convertible functional group include carboxyl group, amino group, hydroxyl group, carbonyl group, mercapto group, a halogen atom and the like.

In compound (2), compound (2a) wherein $R^1$ and $R^2$ are

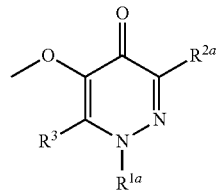

wherein $R^{1a}$ is an alkyl group or a heteroaromatic ring such as a 2-pyridine ring or a thiazole ring and the like, $R^{2a}$ is a substituent other than hydrogen atom, and other symbols are as defined above,
can be produced by, for example, the method shown by the following reaction scheme 2 or a method analogous thereto.

Reaction scheme 2

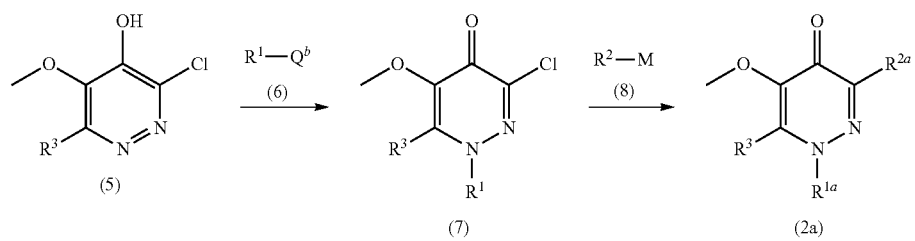

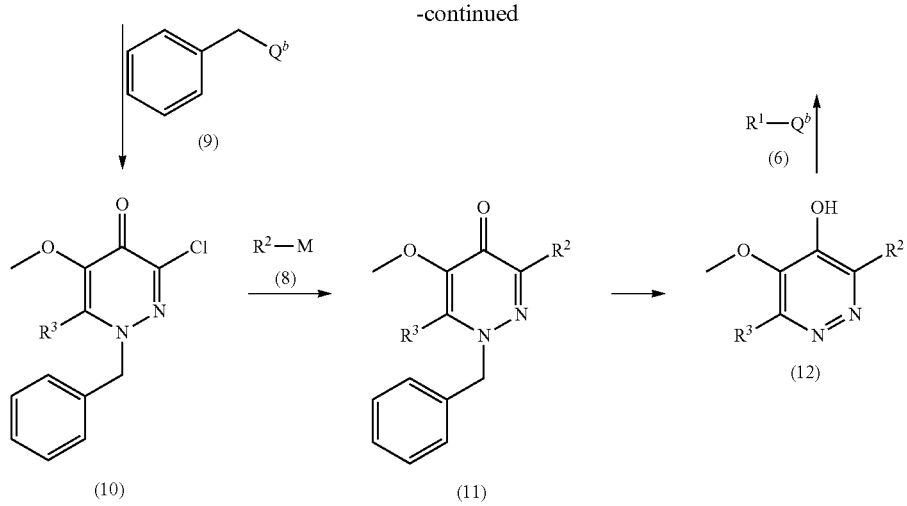

wherein $Q^b$ is a leaving group, M is, for example, boronic acid, boronate ester, zinc halide, magnesium halide and the like, and other symbols are as defined above.

Examples of the leaving group for $Q^b$ include a halogen atom (e.g., chlorine, bromine, iodine), an optionally halogenated $C_{1-6}$ alkylsulfonyloxy group (e.g., methylsulfonyloxy, ethylsulfonyloxy, trifluoromethylsulfonyloxy), a $C_{6-10}$ arylsulfonyloxy group optionally substituted by a $C_{1-6}$ alkyl group (e.g., benzenesulfonyloxy, p-toluenesulfonyloxy), a methanesulfonyl group and the like, with preference given to a halogen atom and an optionally halogenated $C_{1-6}$ alkylsulfonyloxy group.

Compound (5) can be produced by a method known per se or a method analogous thereto.

Compound (6) may be a commercially available product, or can be produced by a method known per se or a method analogous thereto.

Compound (7) can be produced by reacting compound (5) with compound (6). In the reaction, compound (6) is used in an amount of generally about 1-10 mol, preferably 1-3 mol, per 1 mol of compound (5).

This reaction is generally performed in the presence of a base. Examples of the base include inorganic bases, basic salts, aromatic amines, tertiary amines, alkali metal hydrides, metal amides, alkyl metals, aryl metals, metal alkoxides and the like. Such base is used in an amount of generally about 1-10 mol, preferably 1-3 mol, per 1 mol of compound (5).

This reaction is advantageously performed by using a solvent inert to the reaction. While such solvent is not particularly limited as long as the reaction proceeds, for example, solvents such as ethers, hydrocarbons, amides, halogenated hydrocarbons, sulfoxides and the like, a mixed solvent thereof and the like are preferable.

The reaction temperature is generally room temperature −200° C., preferably room temperature −150° C.

While the reaction time varies depending on the reagent and solvent to be used, it is generally 0.5-48 hr, preferably 1-20 hr.

Compound (8) may be a commercially available product, or can be produced by a method known per se or a method analogous thereto.

Compound (9) may be a commercially available product, or can be produced by a method known per se or a method analogous thereto.

Compound (10) can be produced by reacting compound (5) with compound (9). In the reaction, compound (9) is used in an amount of generally about 1-10 mol, preferably 1-3 mol, per 1 mol of compound (5).

This reaction is generally performed in the presence of a base. Examples of the base include inorganic bases, basic salts, aromatic amines, tertiary amines, alkali metal hydrides, metal amides, alkyl metals, aryl metals, metal alkoxides and the like. Such base is used in an amount of generally about 1-10 mol, preferably 1-3 mol, per 1 mol of compound (5).

This reaction is advantageously performed by using a solvent inert to the reaction. While such solvent is not particularly limited as long as the reaction proceeds, for example, solvents such as ethers, hydrocarbons, amides, halogenated hydrocarbons, sulfoxides and the like, a mixed solvent thereof and the like are preferable.

The reaction temperature is generally room temperature −200° C., preferably room temperature −150° C.

While the reaction time varies depending on the reagent and solvent to be used, it is generally 0.5-48 hr, preferably 1-20 hr.

Compound (11) can be produced by reacting compound (10) with compound (8). In the reaction, compound (8) is used in an amount of generally about 1-10 mol, preferably 1-3 mol, per 1 mol of compound (10).

This reaction is performed in the presence of a metal catalyst or a base. Examples of the metal catalyst include palladium catalysts such as tetrakistriphenylphosphine palladium, palladium acetate, tris(dibenzylideneacetone)dipalladium, dichloro[1,1'-bis(diphenylphosphino)ferrocene]palladium and the like, nickel catalysts such as bis(1,5-cyclooctadiene)nickel and the like, and the like. Examples of the base include inorganic bases, tertiary amines, alkali metal hydrides, metal amides, metal alkoxides and the like. The metal catalyst is used in an amount of generally about 0.01-1 mol, preferably 0.05-0.3 mol, per 1 mol of compound (10). The base is used in an amount of generally about 1-10 mol, preferably 1-3 mol, per 1 mol of compound (10).

When desired, this reaction can be performed using a phosphine ligand. Examples of the phosphine ligand include triphenylphosphine, tributylphosphine, diphenylphosphinoferrocene, BINAP and the like. Such phosphine ligand is used in an amount of generally about 0.01-2 mol, preferably 0.1-0.6 mol, per 1 mol of compound (10).

This reaction is advantageously performed by using a solvent inert to the reaction. While such solvent is not particularly limited as long as the reaction proceeds, for example, solvents such as ethers, hydrocarbons, amides, halogenated hydrocarbons and the like, a mixed solvent thereof and the like are preferable.

The reaction temperature is generally room temperature −200° C., preferably room temperature −150° C.

While the reaction time varies depending on the reagent and solvent to be used, it is generally 0.5-24 hr, preferably 1-12 hr.

Compound (12) can be produced from compound (11) by a method known per se, for example, the deprotection method of benzyl group described in Wiley-Interscience (1999), "Protective groups in Organic Synthesis, 3$^{rd}$ Ed." (Theodora W. Greene, Peterg. M. Wuts) and the like.

Compound (2a) can be produced by a reaction of compound (7) with compound (8), or a reaction of compound (12) with compound (6). In the reaction, compound (8) is used in an amount of generally about 1-10 mol, preferably 1-3 mol, per 1 mol of compound (7), and compound (6) is used in an amount of generally about 1-10 mol, preferably 1-3 mol, per 1 mol of compound (12).

The reaction of compound (7) with compound (8) is performed in the presence of a metal catalyst or a base. Examples of the metal catalyst include palladium catalysts such as tetrakistriphenylphosphine palladium, palladium acetate, tris(dibenzylideneacetone)dipalladium, dichloro[1,1'-bis(diphenylphosphino)ferrocene]palladium and the like, nickel catalysts such as bis(1,5-cyclooctadiene)nickel and the like, and the like. Examples of the base include inorganic bases, tertiary amines, alkali metal hydrides, metal amides, metal alkoxides and the like. The metal catalyst is used in an amount of generally about 0.01-1 mol, preferably 0.05-0.3 mol, per 1 mol of compound (7). The base is used in an amount of generally about 1-10 mol, preferably 1-3 mol, per 1 mol of compound (7).

When desired, this reaction can be performed by adding a phosphine ligand. Examples of the phosphine ligand include triphenylphosphine, tributylphosphine, diphenylphosphinoferrocene, BINAP and the like. Such phosphine ligand is used in an amount of generally about 0.01-2 mol, preferably 0.1-0.6 mol, per 1 mol of compound (7).

This reaction is advantageously performed by using a solvent inert to the reaction. While such solvent is not particularly limited as long as the reaction proceeds, for example, solvents such as ethers, hydrocarbons, amides, halogenated hydrocarbons and the like, a mixed solvent thereof and the like are preferable.

The reaction temperature is generally room temperature −200° C., preferably room temperature −150° C.

While the reaction time varies depending on the reagent and solvent to be used, it is generally 0.5-24 hr, preferably 1-12 hr.

The reaction of compound (12) with compound (6) is generally performed in the presence of a base. Examples of the base include inorganic bases, basic salts, aromatic amines, tertiary amines, alkali metal hydrides, metal amides, alkyl metals, aryl metals, metal alkoxides and the like. Such base is used in an amount of generally 1-10 mol, preferably 1-3 mol, per 1 mol of compound (12).

This reaction is advantageously performed by using a solvent inert to the reaction. While such solvent is not particularly limited as long as the reaction proceeds, for example, solvents such as ethers, hydrocarbons, amides, halogenated hydrocarbons, sulfoxides and the like, a mixed solvent thereof and the like are preferable.

The reaction temperature is generally room temperature −200° C., preferably room temperature −150° C.

While the reaction time varies depending on the reagent and solvent to be used, it is generally 0.5-48 hr, preferably 1-20 hr.

In compound (2), compound (2a) wherein $R^1$ and $R^2$ are

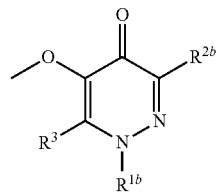

wherein $R^{1b}$ is an aromatic ring, $R^{2b}$ is a hydrogen atom, and other symbols are as defined above,
can be produced by, for example, the method shown in the following reaction scheme 3 or a method analogous thereto.

Reaction scheme 3

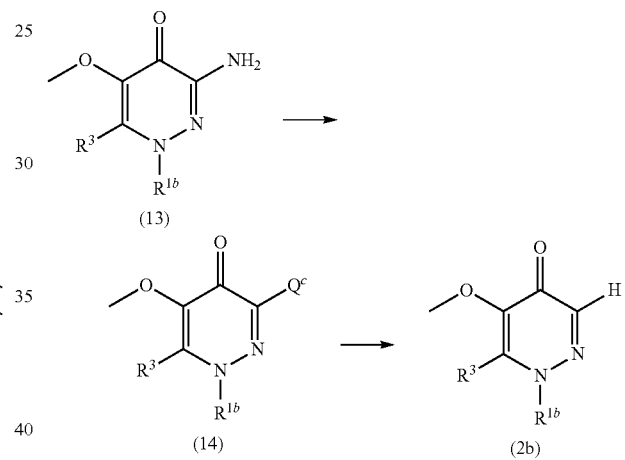

wherein $Q^c$ is a leaving group, and other symbols are as defined above.

Examples of the leaving group for $Q^c$ include a halogen atom (e.g., chlorine, bromine, iodine), and the like.

Compound (13) can be produced by a method known per se or a method analogous thereto.

Compound (14) can be produced by reacting compound (13) with copper halide in the presence of isoamyl nitrite. Examples of the copper halide include copper iodide, copper bromide, copper chloride and the like. Isoamyl nitrite is used in an amount of generally about 1-10 mol, preferably 1-3 mol, per 1 mol of compound (13). Copper halide is used in an amount of generally about 1-10 mol, preferably 1-3 mol, per 1 mol of compound (13).

This reaction is advantageously performed by using a solvent inert to the reaction. While such solvent is not particularly limited as long as the reaction proceeds, for example, solvents such as ethers, hydrocarbons, amides, halogenated hydrocarbons, sulfoxides and the like, a mixed solvent thereof and the like are preferable.

The reaction temperature is generally room temperature −150° C., preferably room temperature −70° C.

While the reaction time varies depending on the reagent and solvent to be used, it is generally 1-12 hr, preferably 1-6 hr.

Compound (2b) can be produced by reacting a metal catalyst with compound (14) under a hydrogen atmosphere. Examples of the metal catalyst include metal catalysts generally used for a catalytic reduction, such as palladium on carbon, palladium hydroxide, platinum on carbon and the like. The metal catalyst is used in an amount of generally about 1-mol, preferably 1-10 mol, per 1 mol of compound (14).

This reaction is advantageously performed by using a solvent inert to the reaction. While such solvent is not particularly limited as long as the reaction proceeds, for example, solvents such as ethers, hydrocarbons, amides, halogenated hydrocarbons, sulfoxides and the like, a mixed solvent thereof and the like are preferable.

The reaction temperature is generally room temperature $-100°$ C., preferably room temperature $-50°$ C.

While the reaction time varies depending on the reagent and solvent to be used, it is generally 12-96 hr, preferably 48-72 hr.

In compound (I), compound (1c) wherein the partial structural formula

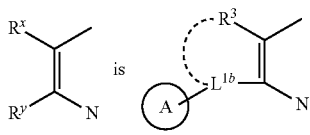

wherein each symbol is as defined above, can be produced from compound (2c) or (2d) shown below by, for example, a method similar to the production of compound (1a) and compound (1b) shown in reaction scheme 1, or a method analogous thereto.

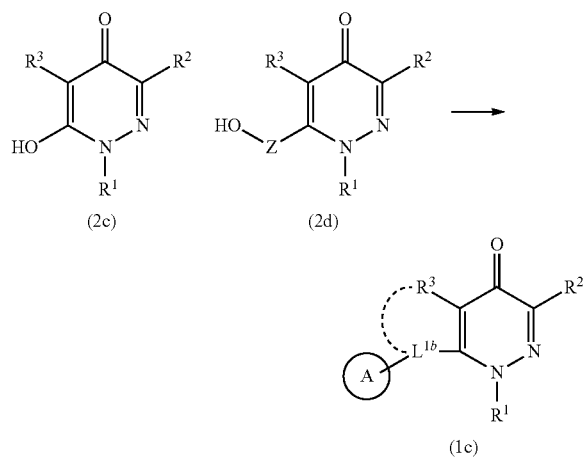

wherein Z is optionally substituted $C_{1-6}$ alkylene, and other symbols are as defined above.

Compound (2c) and compound (2d) can be produced by a method known per se or a method analogous thereto.

Compound (I) obtained by the aforementioned methods can be isolated or purified by the ordinary separation means such as recrystallization, distillation, chromatography and the like. If thus-obtained compound (I) of the present invention is obtained in a free form, they can be converted to their salts by the known methods or by a comparable method (e.g., neutralization, etc.), or in reverse, if they are obtained in the salt form, they can be converted to a free form or other salts by the known methods or by a comparable method.

In any of the above mentioned manufacturing methods or processes, if desired, compound (I) can be synthesized by further applying one or combination of known reactions such as protection/deprotection reactions, acylation reactions, alkylation reactions, hydrogenation reactions, oxidation reactions, reduction reactions, carbon chain extension reactions, substituent exchanging reactions, and so on.

Compound (I) may be used as a prodrug. A prodrug of compound (I) means a compound which is converted to compound (I) with a reaction due to an enzyme, an gastric acid, etc. under the physiological condition in the living body, that is, a compound which is converted to compound (I) with oxidation, reduction, hydrolysis, etc. according to an enzyme; a compound which is converted to compound (I) by hydrolysis etc. due to gastric acid, etc.

A prodrug of compound (I) may be a compound obtained by subjecting an amino group in compound (I) to an acylation, alkylation or phosphorylation (e.g., a compound obtained by subjecting an amino group in compound (I) to an eicosanoylation, alanylation, pentylaminocarbonylation, (5-methyl-2-oxo-1,3-dioxolen-4-yl)methoxycarbonylation, tetrahydrofuranylation, pyrrolidylmethylation, pivaloyloxymethylation and tert-butylation, etc.); a compound obtained by subjecting a hydroxy group in compound (I) to an acylation, alkylation, phosphorylation or boration (e.g., a compound obtained by subjecting an hydroxy group in compound (I) to an acetylation, palmitoylation, propanoylation, pivaloylation, succinylation, fumarylation, alanylation, dimethylaminomethylcarbonylation, etc.); a compound obtained by subjecting a carboxyl group in compound (I) to an esterification or amidation (e.g., a compound obtained by subjecting a carboxyl group in compound (I) to an ethyl esterification, phenyl esterification, carboxymethyl esterification, dimethylaminomethyl esterification, pivaloyloxymethyl esterification, ethoxycarbonyloxyethyl esterification, phthalidyl esterification, (5-methyl-2-oxo-1,3-dioxolen-4-yl)methyl esterification, cyclohexyloxycarbonylethyl esterification and methylamidation, etc.) and the like. Any of these compounds can be produced from compound (I) by a known method. A prodrug for compound (I) may also be one which is converted into compound (I) under a physiological condition, such as those described in IYAKUHIN no KAIHATSU (Development of Pharmaceuticals), Vol. 7, Design of Molecules, p. 163-198, Published by HIROKAWA SHOTEN (1990).

The compound of the present invention has an excellent PDE10A inhibitory activity, and for example, is useful as a medicament for preventing or treating the following diseases and symptoms.

psychotic disorder (e.g., brief psychotic disorder, induced delusional disorder);
psychotic diseases induced by alcohol, amphetamine, cannabinoid, cocaine, hallucinogens, obesity, opioids, phencyclidine and the like;
delusional disorder;
anxiety disorder;
movement disorder;
mood disorder;
major depression;
depression overlapping with psychotic disorders including delusional disorder or schizophrenia;
major depression episode of mild, moderate or severe type;
manic or mixed episode;
hypomanic episode;
depression episode with atypical features;

depression episode with melancholic features;
depression episode with catatonic features;
mood episode with postpartum onset;
post-stroke depression;
dysthymic disorder;
minor depression;
autism;
drug addiction;
neurodegenerative disease;
neurodegeneration associated with brain trauma;
neurodegeneration associated with cerebral stroke;
neurodegeneration associated with cerebral infarction;
hypoglycemia-induced neurodegeneration;
neurodegeneration associated with epilepsy seizure;
neurodegeneration associated with neurotoxin;
multi-system atrophy;
Alzheimer's disease;
dementia;
multi-infarct dementia;
alcoholic dementia or other drug-related dementia;
dementia associated with intracranial tumor or cerebrum trauma;
dementia associated with Huntington's disease or Parkinson's disease;
AIDS-related dementia syndrome;
fronto temporal dementia;
delirium;
amnestic disorder;
post-traumatic stress disorder;
mental retardation (hypophrenia);
learning disorder (e.g., dyslexia, dyscalculia, agraphia);
attention-deficit hyperactivity disorder;
age-related cognitive decline;
premenstrual dysphoric disorder;
bipolar disorder including bipolar I disorder or bipolar II disorder;
cyclothymic disorder;
Parkinson's disease;
Huntington's disease;
delusion;
schizophrenia (e.g., paranoid schizophrenia, disorganized schizophrenia, catatonic schizophrenia, undifferentiated schizophrenia, residual schizophrenia);
schizoaffective disorder;
schizoaffective disorder of the delusional type or the depressive type;
personality disorder of the paranoid type;
personality disorder of the schizoid type;
obesity;
metabolic syndrome;
non-insulin dependent diabetes;
glucose intolerance.

In particular, the compound of the present invention is useful for preventing or treating schizophrenia.

Since the compound of the present invention demonstrates excellent metabolic stability, superior therapeutic effects on the aforementioned diseases are expected even at a low dosage.

Since the compound of the present invention has low toxicity (e.g., more superior as medicament in terms of acute toxicity, chronic toxicity, genetic toxicity, reproductive toxicity, cardiotoxicity, drug interaction, carcinogenicity and the like), it can be safely administered as it is as a medicament, or as a pharmaceutical composition obtained by mixing with a pharmaceutically acceptable carrier etc., orally or parenterally to a mammal (e.g., human, monkey, bovine, horse, swine, mouse, rat, hamster, rabbit, cat, dog, sheep, goat etc.).

The compound of the present invention can be used singly as a medicament according to a method known per se (e.g., the method described in the Japanese Pharmacopoeia etc.) as a production method of a pharmaceutical preparation. In addition, the compound of the present invention can be used as a pharmaceutical composition by mixing with a pharmacologically acceptable carrier.

A medicament containing the compound of the present invention can be safely administered as, for example, tablets (inclusive of sugar-coated tablet, film-coated tablet, sublingual tablet, orally disintegrable tablet, buccal, etc.), pills, powders, granules, capsules (inclusive of soft capsule, and microcapsule), troches, syrups, liquids, emulsions, suspensions, controlled-release preparations (e.g., quick-release preparation, sustained-release preparation, sustained-release microcapsule), aerosols, films (e.g., orally disintegrable film, adhesive film for application to the oral cavity mucosa), injections (e.g., subcutaneous injection, intravenous injection, intramuscular injection, intraperitoneal injection), drip infusion, percutaneous absorbent, ointment, lotion, patch, suppositories (e.g., rectal suppository, vaginal suppository), pellets, transnasal preparations, pulmonary preparations (inhalant), eye drops and the like, in an oral or parenteral route (e.g., intravenous, intramuscular, subcutaneous, intraorgan, intranasal, intradermal, ophthalmic instillation, intracerebral, intrarectal, intravaginal, intraperitoneal, directly to lesion).

As a pharmaceutical acceptable carrier, common organic or inorganic carrier substances are used as formulation raw materials. Carriers are added as vehicles, lubricants, binders and disintegrants in the solid formulations; and as solvents, solubilizing agents, suspending agents, isotonization agents, buffers and soothing agents in the liquid formulations. If desired, formulation additives such as antiseptics, antioxidants, colorants, sweeteners, etc. can be used.

Favorable examples of the vehicles are as follows: lactose, sucrose, D-mannitol, D-sorbitol, starch, α-starch, dextrin, crystalline cellulose, low-substituted hydroxypropyl cellulose, sodium carboxymethylcellulose, gum Arabic, pullulan, light anhydrous silicic acid, synthetic aluminum silicate and magnesium metasilicic aluminate.

Favorable examples of the lubricants include magnesium stearate, calcium stearate, talc and colloidal silica.

Favorable examples of the binders are as follows: α-starch, sucrose, gelatin, gum Arabic, methylcellulose, carboxymethylcellulose, sodium carboxymethylcellulose, crystalline cellulose, sucrose, D-mannitol, trehalose, dextrin, pullulan, hydroxypropylcellulose, hydroxypropyl methyl cellulose and polyvinylpyrrolidone.

Favorable examples of the disintegrants are as follows: lactose, sucrose, starch, carboxymethylcellulose, calcium carboxymethylcellulose, croscarmellose sodium, sodium carboxymethyl starch, light anhydrous silicic acid and low-substituted hydroxypropylcellulose.

Favorable examples of the solvents are as follows: water for injection, physiological saline, Linger solution, alcohol, propylene glycol, polyethylene glycol, sesame oil, corn oil, olive oil and cottonseed oil.

Favorable examples of the solubilizing agents are as follows: polyethylene glycol, propylene glycol, D-mannitol, trehalose, benzyl benzoate, ethanol, tris-aminomethane, cholesterol, triethanolamine, sodium carbonate, sodium citrate, sodium salicylate and sodium acetate.

Favorable examples of the suspending agents are as follows: surfactants such as stearyl triethanolamine, sodium lauryl sulfate, laurylamino propionic acid, lecithin, benzalkonium chloride, benzethonium chloride, and glycerin monostearate; hydrophilic polymers such as polyvinyl alcohol, polyvinyl pyrrolidone, sodium carboxymethylcellulose, methylcellulose, hydroxymethyl cellulose, hydroxyethyl cellulose and hydroxypropyl cellulose; polysorbates, and polyoxyethylene hydrogenated castor oil.

Favorable examples of the isotonization agents include sodium chloride, glycerin, D-mannitol, D-sorbitol and glucose.

Favorable examples of the buffers include buffer solutions of phosphates, acetates, carbonates and citrates.

Favorable examples of the soothing agents include benzyl alcohol.

Favorable examples of antiseptics include para-oxybenzoic acid esters, chlorobutanol, benzyl alcohol, phenethyl alcohol, dehydroacetic acid and sorbic acid.

Favorable examples of antioxidants include sulfites and ascorbates.

Favorable examples of the colorants include water soluble edible tar dyes (e.g., edible dyes such as Food Red No. 2 and No. 3, Food Yellow No. 4 and No. 5, Food Blue No. 1 and 2); water insoluble lake dyes (e.g., aluminum salts of the aforementioned water soluble edible tar dyes), natural dyes (e.g., β-carotene, chlorophyll, ferric oxide red).

Favorable examples of the sweeteners include sodium saccharin, dipotassium glycyrrhizate, aspartame and stevia.

The pharmaceutical compositions of the present invention can be manufactured by the common methods in the field of formulation technology, for example, methods listed in the Japanese pharmacopoeia. Specific manufacturing methods for formulations are described in detail below.

The content of the compound of the present invention in the pharmaceutical compositions of the present invention varies based on the dosage forms, dosages of the compound of the present invention, etc. For example, the content approximately ranges from 0.01 to 100 wt % and preferably from 0.1 to 95 wt % relative to the entire amount of the composition.

The dosage of the compound of the present invention depends upon injection targets, administration routes, target diseases, symptoms, etc. For example, in the case of oral administration in patients with schizophrenia (adults, bodyweight of about 60 kg), generally a single dose ranges from about 0.1 to about 20 mg/kg bodyweight, preferably from about 0.2 to about 10 mg/kg bodyweight, further preferably from about 0.5 to about 10 mg/kg bodyweight, and this dosage is preferably administered once daily or several times daily (e.g., 3 times).

The compound of the present invention may be used in combination with other active ingredients. Examples of the drug that can be used in combination or concomitant with the compound of the present invention (hereinafter sometimes to be abbreviated as concomitant drug) include the following.

(1) A therapeutic drug for psychotic diseases, particularly schizophrenia, or bipolar disorder, obsessive disorder, major depression, Parkinson's disease, Huntington's disease, Alzheimer's disease, cognitive dysfunction and memory disorders [for example, atypical antipsychotic agents (e.g., clozapine, olanzapine, risperidone, aripiprazole, blonanserin, iloperidone, asenapine, ziprasidone, quetiapine, zotepine etc.), typical antipsychotic agents (e.g., haloperidol, chlorpromazine etc.), selective serotonin reuptake inhibitor (e.g., paroxetine, sertraline, fluvoxamine, fluoxetine etc.), selective serotonin.noradrenaline reuptake inhibitor (e.g., milnacipran, venlafaxine etc.), selective noradrenaline dopamine reuptake inhibitor (e.g., bupropion etc.), tetracyclic antidepressant (e.g., amoxapine, clomipramine etc.), tricyclic antidepressant (e.g., imipramine, amitriptyline etc.), other antidepressant (e.g., NS-2359, Lu AA21004, DOV21947 etc.), $\alpha_7$ nicotine receptor agonist, $\alpha_7$ nicotine receptor activity regulator, $\alpha_7$ nicotine receptor partial regulator (e.g., SSR-180711, PNU-120596 etc.), PDE1 inhibitor, PDE2 inhibitor, PDE4 inhibitor, PDE5 inhibitor, PDE7 inhibitor, PDE9 inhibitor, other PDE inhibitor, calcium channel inhibitor, NK2 antagonist, NK3 antagonist, muscarine type M1 acetylcholine receptor activity regulator, muscarine type M2 acetylcholine receptor activity regulator, adenosine receptor regulator, muscarine type M4 acetylcholine receptor activity regulator, muscarine type M5 acetylcholine receptor activity regulator, adenosine receptor regulator, glycine transporter type 1 inhibitor (e.g., ALX5407, SSR504734 etc.), glutamate enhancer (e.g., ampakine), NMDA-type glutamate receptor regulator, metabolic glutamate receptor regulator (e.g., CDPPB, MPEP etc.), antianxiety drug (e.g., benzodiazepine antianxiety drug (e.g., diazepam, etizolam etc.), serotonin $5-HT_{1A}$ agonist (e.g., tandospirone etc.)), hypnotic pills (e.g., benzodiazepine hypnotic pills (e.g., estazolam, triazolam etc.), non-benzodiazepine hypnotic pills (e.g., zolpidem etc.), melatonin receptor agonist (e.g., ramelteon etc.)), β amyloid vaccine, β amyloid degrading enzyme etc., brain function activator (e.g., aniracetam, nicergoline etc.), cannabinoid regulator, cholinesterase inhibitor (e.g., donepezil, rivastigmine, galanthamine), therapeutic drug for Parkinson's disease (e.g., dopamine receptor agonist (e.g., L-DOPA, bromocriptine, pergolide, talipexole, pramipexole, cabergoline, amantadine etc.), monoamine oxidase inhibitor (e.g., deprenyl, selegiline, ramacemide, riluzole etc.), anticholinergic agent (e.g., trihexyphenidyl, biperiden etc.), COMT inhibitor (e.g., entacapone etc.), a therapeutic drug for amyotrophic lateral sclerosis (e.g., riluzole etc., neurotrophic factor etc.), apoptosis inhibitor (e.g., CPI-1189, IDN-6556, CEP-1347 etc.), neuronal differentiation-regeneration promoter (e.g., leteprinim, xaliproden (SR-57746-A), SB-216763 etc.)];

(2) a therapeutic drug for diseases easily developed with schizophrenia [for example, therapeutic drug for diabetes (e.g., PPAR acting drug (e.g., agonist, inhibitor, pioglitazone, rosiglitazone, troglitazone), insulin secretagogue (e.g., sulfonylurea drugs, non-sulfonylurea drugs), a glucosidase inhibitor (e.g., acarbose), insulin sensitizer (e.g., PPAR-γ acting drug, PTP-1B inhibitor, DPP-4 inhibitor, 11β-HSD inhibitor), liver gluconeogenesis inhibitor (e.g., glucagon antagonist, metformin), insulin, insulin derivative), antiobesity drug (e.g., β-3 agonist, CB1 agonist, neuropeptide Y5 inhibitor, anorexigenic agent (e.g., sibutramine), lipase inhibitor (e.g., orlistat)), a therapeutic drug for hyperlipidemia such as a cholesterol lowering agent and the like (e.g., statin therapeutic drug for hyperlipidemia (e.g., pravastatin sodium, atrovastatin, simvastatin, rosuvastatin etc.), fibrate (e.g., clofibrate etc.), squalene synthase inhibitor), antihypertensive agent, non-steroidal anti-inflammatory agent (e.g., meloxicam, teoxicam, indomethacin, ibuprofen, celecoxib, rofecoxib, aspirin, indomethacin etc.), disease-modified anti-rheumatic drug (DMARDs), anticytokine agent (e.g., TNF inhibitor, MAP kinase inhibitor and the like), steroid drug (e.g., dexamethasone, hexestrol, cortisone acetate etc.), sex hormone or a derivative thereof (e.g., progesterone, estradiol, estradiol benzoate etc.), parathyroid hormone (PTH), calcium receptor antagonist etc.]

The form of administration of concomitant drugs with the compound of the present invention is not particularly limited and is acceptable as long as the compound of the present invention is combined with concomitant drugs at the time of administration. Examples of such forms of administration are as follows:

(1) Administration of a single formula obtained simultaneous formulation of the compound of the present invention with a concomitant drug, (2) Simultaneous administration via the same administration route for two kinds of formulas obtained by independent formulations of the compound of the present invention and a concomitant drug, (3) Administrations at different times via the same administration route for two kinds of formulas obtained by independent formulations of the compound of the present invention and a concomitant drug, (4) Simultaneous administration via different administration routes for two kinds of formulas obtained by independent formulations of the compound of the present invention and a concomitant drug, (5) Administrations at different times via different administration routes for two kinds of formulas obtained by independent formulations of the compound of the present invention and a concomitant drug (e.g., administration in the order of the compound of the present invention and then a concomitant drug, or administration in the reversed order). These forms of administration are summarized below and abbreviated as a combination drug of the present invention.

When administering the combination drug of the present invention, a concomitant drug and the compound of the present invention can be administered at the same time, but the compound of the present invention can be administered after a concomitant drug is administered or after the compound of the present invention is administered, a concomitant drug can be administered. When administering at different times, the time difference depends upon the active ingredients to be administered, drug forms and methods of administration. For example, when a concomitant drug is administered first, the compound of the present invention can be administered within 1 min. to 3 days, preferably within 10 min. to 1 day and more preferably within 15 min. to 1 hour after the concomitant drug is administered. However, if the compound of the present invention is administered first, a concomitant drug can be administered within 1 min. to 1 day, preferably within 10 min. to 6 hours and more preferably within 15 min. to 1 hour after the compound of the present invention is administered.

If there are no problems with side effects of the concomitant drugs, any dosages can be set. A daily dosage as a concomitant drug depends upon dosages, administration subjects, administration routes, target diseases, symptoms, etc. For example, in the case of oral administration in patients with schizophrenia (adults, bodyweight of about 60 kg), a normal once dosage ranges from about 0.1 to about 20 mg/kg bodyweight, preferably from about 0.2 to about 10 mg/kg bodyweight and more preferably from about 0.5 to about 10 mg/kg bodyweight. It is preferable that this dosage is administered once daily to several times daily (e.g., 3 times).

If the compound of the present invention is used in combination with a concomitant drug, the respective dosages can be reduced within a safe range with consideration of the opposite effects of the respective drugs.

The combination drug of the present invention exhibits low toxicity. For example, the compound of the present invention or(and) the aforementioned concomitant drug can be combined with a pharmaceutically acceptable carrier according to the known method to prepare a pharmaceutical composition such as tablets (including sugar-coated tablet and film-coated tablet), powders, granules, capsules (including soft capsule), liquids, injections, suppositories, sustained-release agents, etc. These compositions can be administered safely orally or non-orally (e.g., topically, rectally, intravenously etc.).

The pharmaceutically acceptable carriers that may be used for manufacturing the combination drug of the present invention can be the same as those used in the pharmaceutical composition of the present invention as mentioned above.

A mixing ratio between the compound of the present invention and a concomitant drug in the combination drug of the present invention can be selected appropriately based on the administration subjects, administration routes and diseases.

The aforementioned concomitant drugs can be combined at an appropriate proportion if two or more drugs are combined. A dosage of the concomitant drug can be selected appropriately based on the dosages used clinically. In addition, a mixing ratio between the compound of the present invention and a concomitant drug can be selected appropriately based on the administration subjects, administration routes, target diseases, symptoms, combinations, etc. For example, if the administration subject is humans, a concomitant drug may be used in an amount ranging from 0.01 to 100 parts by weight relative to 1 part by weight of the compound of the present invention.

For example, the content of the compound of the present invention in the combination drug of the present invention varies with the drug form of formulations. Generally, it is present in a range from about 0.01 to 99.9 wt %, preferably from about 0.1 to about 50 wt % and more preferably from about 0.5 to about 20 wt % relative to the entire formula.

The content of a concomitant drug in the combination drug of the present invention varies with the drug form of formulations. Generally it is present in a range from about 0.01 to 99.9 wt %, preferably from about 0.1 to about 50 wt % and more preferably from about 0.5 to about 20 wt % relative to the entire formula.

The content of an additive such as carriers in the combination drug of the present invention varies with the drug form of formulations. Generally it is present in a range from about 1 to 99.99 wt % and preferably from about 10 to about 90 wt % relative to the entire formula.

When the compound of the present invention and a concomitant drug are formulated independently, the same contents can be applied.

Since the dosages may fluctuate under various conditions as mentioned above, a dosage less than the dosages may be sufficient or it may be necessary to administer at a dosage exceeding the range.

EXAMPLES

The present invention is explained in detail in the following by referring to Examples, Experimental Examples and Preparation Examples. However, the examples do not limit the present invention and can be modified within the scope of the present invention.

The "room temperature" in the following Examples is generally about 10° C. to about 35° C. The ratio for a mixed solvent is, unless otherwise specified, a volume mixing ratio and % means wt % unless otherwise specified.

In silica gel column chromatography, the indication of NH means use of aminopropylsilane-bonded silica gel. In HPLC (high performance liquid chromatography), octadecyl-bonded silica gel was used. The ratio of elution solvents is, unless otherwise specified, a volume mixing ratio.

In the following Examples, the following abbreviations are used.

THF: tetrahydrofuran
DMF: N,N-dimethylformamide
DMSO: dimethyl sulfoxide
ESI: electrospray ionization method
API: atmospheric chemical ionization method
[M+H]$^+$: molecular ion peak TFA: trifluoroacetic acid
M: molar concentration
N: normal concentration
WSC: N-(3-dimethylaminopropyl)-N'-ethylcarbodiimide
HOBt: 1-hydroxybenzotriazole monohydrate
HPLC: high performance liquid chromatography $^1$H NMR (proton nuclear magnetic resonance spectrum) was measured by Fourier-transform type NMR. For the analysis, ACD/SpecManager (trade name) and the like were used. Very broad peaks showing protons of hydroxyl group, amino group and the like are not described.

MS (mass spectrum) was measured by LC/MS (liquid chromatography mass spectrometer). As the ionization method, ESI (ElectroSpray Ionization) method, or APCI (Atmospheric Pressure Chemical Ionization) method was used. The data shows Found. Generally, molecular ion peaks are observed. However, when a compound having a tert-butoxycarbonyl group (-Boc) is used, a peak free of a tert-butoxycarbonyl group or tert-butyl group may be observed as a fragment ion. In addition, when a compound having a hydroxyl group (—OH) is used, a peak free of $H_2O$ may be observed as a fragment ion. In the case of a salt, generally, a molecular ion peak or a fragment ion peak of a free form is observed.

Example 1

1-methyl-5-[3-(1-methyl-1H-benzimidazol-2-yl)propoxy]-3-(1-phenyl-1H-pyrazol-5-yl)pyridazin-4(1H)-one A) (1-phenyl-1H-pyrazol-5-yl)boronic acid To a solution of 1-phenyl-1H-pyrazole (20.0 g) in tetrahydrofuran (700 mL) was added dropwise n-butyllithium (2.5M hexane solution, 58.3 mL) under a nitrogen atmosphere at −78° C., and the mixture was stirred at the same temperature for min. To the reaction mixture was added triisopropyl borate (52.2 g) at −78° C., and the mixture was stirred at the same temperature for 1 hr. The mixture was gradually warmed to room temperature, and stirred at room temperature for 20 hr. To the reaction mixture was added acetic acid (20 mL) to adjust to pH 5, and the mixture was concentrated to give the title compound (25.0 g).
MS (ESI+): [M+H]$^+$ 189.0.

B) 1-phenyl-5-(4,4,5,5-tetramethyl-1,3,2-dioxaborolan-2-yl)-1H-pyrazole (1-Phenyl-1H-pyrazol-5-yl)boronic acid (25.0 g) was dissolved in toluene (700 mL), pinacol (18.0 g) was added at room temperature, and the mixture was stirred at 40° C. for 2 days. The reaction mixture was diluted with dichloromethane, washed successively with water and saturated brine, dried over anhydrous sodium sulfate and filtered, and the filtrate was concentrated. The resulting solid was collected by filtration, and washed with hexane to give the title compound (19.8 g).
$^1$H NMR (400 MHz, CDCl$_3$) δ 1.27 (12H, s), 6.89 (1H, d, J=1.6 Hz), 7.33-7.43 (3H, m), 7.52-7.55 (2H, m), 7.72 (1H, d, J=1.6 Hz).

C) 3-chloro-5-methoxypyridazin-4-ol

3-Chloro-4,5-dimethoxypyridazine (17.0 g) and morpholine (59.0 mL) were stirred at 100° C. for 2 hr, and cooled to 0° C. To the reaction mixture was added phenyl isocyanate (73.8 mL) at 0° C., and the mixture was stirred at the same temperature for min. and diluted with ethyl acetate. The resulting byproduct N-phenylmorpholine-4-carboxamide was removed by filtration. The filtrate was concentrated, and purified by silica gel column chromatography (ethyl acetate/hexane→methanol/ethyl acetate) to give the title compound (9.61 g).
$^1$H NMR (400 MHz, CD$_3$OD) δ 3.88 (3H, s), 8.26 (1H, s).

D) 1-benzyl-3-chloro-5-methoxypyridazin-4(1H)-one

3-Chloro-5-methoxypyridazin-4-ol (10.0 g) was dissolved in N,N-dimethylformamide (300 mL), sodium hydride (3.26 g, 55 wt %) and tetrabutylammonium iodide (4.60 g) were added at 0° C., and the mixture was stirred at the same temperature for 10 min. To the reaction mixture was added benzyl bromide (12.3 g) at 0° C., and the mixture was stirred at room temperature for 20 hr. The reaction mixture was diluted with water, and extracted with dichloromethane. The extract was washed successively with water and saturated brine, dried over anhydrous sodium sulfate and filtered, and the filtrate was concentrated. Recrystallization of the residue from ethyl acetate/hexane gave the title compound (19.8 g).
$^1$H NMR (400 MHz, CDCl$_3$) δ 3.82 (3H, s), 5.31 (2H, s), 7.34-7.42 (5H, m), 7.89 (1H, s).

E) 1-benzyl-5-methoxy-3-(1-phenyl-1H-pyrazol-5-yl)pyridazin-4(1H)-one

1-Benzyl-3-chloro-5-methoxypyridazin-4(1H)-one (13.6 g), 1-phenyl-5-(4,4,5,5-tetramethyl-1,3,2-dioxaborolan-2-yl)-1H-pyrazole (22.0 g), potassium carbonate (51.0 g) and bis(di-tert-butyl(4-dimethylaminophenyl)phosphine)dichloropalladium(II) (1.92 g) were suspended in toluene (330 mL) and water (33.0 mL), and the mixture was heated under reflux under a nitrogen atmosphere for 24 hr. The reaction mixture was cooled to room temperature, diluted with water and saturated aqueous sodium hydrogen carbonate solution, and the mixture was extracted with ethyl acetate. The extract was dried over anhydrous sodium sulfate and filtered, and the filtrate was concentrated, and the residue was recrystallized from ethyl acetate/hexane to give the title compound (15.1 g).
$^1$H NMR (400 MHz, DMSO-d$_6$) δ 3.81 (3H, s), 5.10 (2H, s), 6.95 (1H, d, J=1.6 Hz), 7.05-7.07 (2H, m), 7.24-7.38 (8H, m), 7.74 (1H, d, J=1.6 Hz), 8.33 (1H, s).

F) 5-methoxy-3-(1-phenyl-1H-pyrazol-5-yl)pyridazin-4-ol

1-Benzyl-5-methoxy-3-(1-phenyl-1H-pyrazol-5-yl)pyridazin-4(1H)-one (15.0 g) and palladium hydroxide on carbon (5.88 g, palladium 20%, 50% water moistened product) were suspended in tetrahydrofuran (500 mL) and methanol (300 mL), and the mixture was stirred under a hydrogen atmosphere at room temperature for 2 days. The reaction mixture was filtered through celite, and the filtrate was concentrated and solidified with ethanol/hexane to give the title compound (9.10 g).
MS (ESI+): [M+H]$^+$ 269.2.

G) 5-methoxy-1-methyl-3-(1-phenyl-1H-pyrazol-5-yl)pyridazin-4(1H)-one

Under an argon atmosphere, to a solution of 5-methoxy-3-(1-phenyl-1H-pyrazol-5-yl)pyridazin-4-ol (2.0 g) in dimethylformamide (40 mL) was added 60% sodium hydride (596 mg), with stirring under ice-cooling, and the mixture was stirred at the same temperature for 1.5 hr. Then, dimethyl sulfate (1.058 mL) was added, and the mixture was stirred at the same temperature for 3.5 hr.

To the reaction mixture was added methanol, and the mixture was concentrated under reduced pressure to dryness. The residue was purified by silica gel column chromatography (ethyl acetate/methanol). A fraction containing the title compound was purified again by NH silica gel column chromatography (ethyl acetate/methanol), and crystallized from methanol/ethyl acetate to give the title compound (1.485 g) as white prisms.

MS (ESI+): [M+H]$^+$ 283.2.

H) 5-hydroxy-1-methyl-3-(1-phenyl-1H-pyrazol-5-yl)pyridazin-4(1H)-one

To a solution of sodium iodide (3.75 g) in acetonitrile (150 mL) was added chlorotrimethylsilane (3.17 mL) with stirring at room temperature, and the mixture was stirred for min. Then, 5-methoxy-1-methyl-3-(1-phenyl-1H-pyrazol-5-yl)pyridazin-4(1H)-one (1.41 g) was added, and the mixture was stirred for 30 min at the same temperature, and further refluxed for 3 hr. The reaction mixture was allowed to cool to room temperature, poured into water and the mixture was stirred for 30 min. The mixture was extracted with ethyl acetate, and the organic layer was washed successively with aqueous sodium thiosulfate solution and saturated brine, dried over anhydrous magnesium sulfate and concentrated under reduced pressure. The obtained residue was triturated with ethyl acetate-diisopropyl ether, collected by filtration, and dried to give the title compound (1.032 g) as white needles.

MS (ESI+): [M+H]$^+$ 269.1.

I) 1-methyl-5-[3-(1-methyl-1H-benzimidazol-2-yl)propoxy]-3-(1-phenyl-1H-pyrazol-5-yl)pyridazin-4(1H)-one Toluene (10 mL) was added to di-tert-butyl diazene-1,2-dicarboxylate (173 mg) and triphenylphosphine (229 mg) and the mixture was stirred at room temperature for 10 min. Then, 5-hydroxy-1-methyl-3-(1-phenyl-1H-pyrazol-5-yl)pyridazin-4(1H)-one (154 mg), 3-(1-methyl-1H-benzimidazol-2-yl)propan-1-ol (143 mg) were further added and the mixture was stirred at room temperature for 22 hr. The crystals precipitated from the reaction mixture were collected by filtration, washed successively with toluene, methanol and diisopropyl ether, and dried to give the title compound (134 mg).

MS (ESI+): [M+H]$^+$ 441.1.

Example 2

5-[2-(2,3-dihydro-1H-imidazo[1,2-a]benzimidazol-1-yl)ethoxy]-1-methyl-3-(1-phenyl-1H-pyrazol-5-yl)pyridazin-4(1H)-one A suspension of 5-hydroxy-1-methyl-3-(1-phenyl-1H-pyrazol-5-yl)pyridazin-4(1H)-one (201 mg), 1-(2-chloroethyl)-2,3-dihydro-1H-imidazo[1,2-a]benzimidazole (249 mg), cesium carbonate (428 mg) and sodium iodide (253 mg) in dimethylacetamide (10 mL) was stirred at 80° C. for 13 hr. The reaction mixture was filtered to separate an insoluble material, which was washed with ethyl acetate. The filtrate and washing were combined, and the mixture was concentrated under reduced pressure to dryness. The residue was purified by NH silica gel column chromatography (ethyl acetate/methanol) to give the title compound (227 mg) as a white solid.

MS (ESI+): [M+H]$^+$ 454.2.

Example 3

1-(cyclopropylmethyl)-5-[3-(1-methyl-1H-benzimidazol-2-yl)propoxy]-3-(1-phenyl-1H-pyrazol-5-yl)pyridazin-4(1H)-one

A) 1-(cyclopropylmethyl)-5-methoxy-3-(1-phenyl-1H-pyrazol-5-yl)pyridazin-4(1H)-one Under an argon atmosphere, to a solution of 5-methoxy-3-(1-phenyl-1H-pyrazol-5-yl)pyridazin-4-ol (2.0 g) in dimethylformamide (40 mL) was added 60% sodium hydride (596 mg) with stirring under ice-cooling, and the mixture was stirred at the same temperature for 1.5 hr. Then, (bromomethyl)cyclopropane (1.085 mL) was added, and the mixture was stirred at room temperature for 16 hr. To the reaction mixture was added methanol, and the mixture was concentrated under reduced pressure to dryness. The residue was purified by silica gel column chromatography (ethyl acetate/methanol) and crystallized from methanol/ethyl acetate to give the title compound (2.12 g) as white prisms.

MS (ESI+): [M+H]$^+$ 323.2.

B) 1-(cyclopropylmethyl)-5-hydroxy-3-(1-phenyl-1H-pyrazol-5-yl)pyridazin-4(1H)-one To a solution of sodium iodide (3.75 g) in acetonitrile (150 mL) was added chlorotrimethylsilane (3.17 mL) with stirring at room temperature for 30 min. Then, 1-(cyclopropylmethyl)-5-methoxy-3-(1-phenyl-1H-pyrazol-5-yl)pyridazin-4(1H)-one (1.613 g) was added, and the mixture was stirred for 30 min at the same temperature and further refluxed for 4 hr. The reaction mixture was allowed to cool to room temperature, poured into water and the mixture was stirred for 30 min. The mixture was extracted with ethyl acetate, and the organic layer was washed with saturated brine, dried over anhydrous magnesium sulfate and concentrated under reduced pressure. The obtained residue was triturated with diisopropyl ether, collected by filtration, washed successively with ethyl acetate and diisopropyl ether, and dried to give the title compound (1.23 g) as a pale-brown solid.

MS (ESI+): [M+H]$^+$ 309.2.

C) 1-(cyclopropylmethyl)-5-[3-(1-methyl-1H-benzimidazol-2-yl)propoxy]-3-(1-phenyl-1H-pyrazol-5-yl)pyridazin-4(1H)-one Toluene (10 mL) was added to di-tert-butyl diazene-1,2-dicarboxylate (173 mg) and triphenylphosphine (229 mg) and the mixture was stirred at room temperature for 10 min. Then, 1-(cyclopropylmethyl)-5-hydroxy-3-(1-phenyl-1H-pyrazol-5-yl)pyridazin-4(1H)-one (154 mg), and further, 3-(1-methyl-1H-benzimidazol-2-yl)propan-1-ol (143 mg) were added, and the mixture was stirred at room temperature for 22 hr. The reaction mixture was concentrated under reduced pressure, and the residue was purified by silica gel column chromatography (ethyl acetate/methanol). A fraction containing the title compound was again purified by NH silica gel column chromatography (hexane/ethyl acetate), and crystallized from hexane/ethyl acetate to give the title compound (110 mg) as white prisms.

MS (ESI+): [M+H]$^+$ 481.2.

Example 4

1-(cyclopropylmethyl)-5-[2-(2,3-dihydro-1H-imidazo[1,2-a]benzimidazol-1-yl)ethoxy]-3-(1-phenyl-1H-pyrazol-5-yl)pyridazin-4(1H)-one A suspension of 1-(cyclopropylmethyl)-5-hydroxy-3-(1-phenyl-1H-pyrazol-5-yl)pyridazin-4(1H)-one (231 mg), 1-(2-chloroethyl)-2,3-dihydro-1H-imidazo[1,2-a]benzimidazole (249 mg), cesium carbonate (428 mg) and sodium iodide (253 mg) in dimethylacetamide (10 mL) was stirred at 80° C. for 13 hr. The reaction mixture was filtered and an insoluble material was separated and washed with ethyl acetate. The filtrate and the washing were combined, and concentrated under reduced pressure to dryness. The residue was purified by NH silica gel column chromatography (ethyl acetate/methanol) to give the title compound (231 mg) as a white amorphous powder.

MS (ESI+): [M+H]$^+$ 494.2.

Example 5

5-[3-(1-methyl-1H-benzimidazol-2-yl)propoxy]-3-(1-methyl-1H-pyrazol-5-yl)-1-phenylpyridazin-4(1H)-one

A) methyl 4-methoxy-3-oxo-2-(phenylhydrazono)butanoate

To a solution of aniline (50 g) in 6N hydrochloric acid (536 mL) was added dropwise with stirring under ice-cooling an aqueous solution (142 mL) of sodium nitrite (55.6 g). The solution was added dropwise to a mixed solution of methyl 4-methoxy-3-oxobutanoate (78.5 g) and sodium acetate (264 g) in methanol/water (1.4 L/0.35 L) with stirring under ice-cooling. The total amount was added dropwise, and the mixture was stirred at the same temperature for 2 hr. Water was added to the reaction mixture, and the mixture was stirred for 30 min. The precipitated yellow crystals were collected by filtration, washed successively with water, ethanol/diisopropyl ether (1/9) and diisopropyl ether, and dry to give the title compound (111.2 g) as yellow crystals.

$^1$H NMR (300 MHz, CDCl$_3$): δ 3.51 (3H, s), 3.88 (3H, s), 4.69 (2H, s), 7.18-7.25 (1H, m), 7.37-7.48 (4H, m), 14.99 (1H, br. s.).

B) methyl 5-methoxy-4-oxo-1-phenyl-1,4-dihydropyridazine-3-carboxylate

A suspension of methyl 4-methoxy-3-oxo-2-(phenylhydrazono)butanoate (25.03 g) in dimethylformamide dimethylacetal (120 mL) was stirred at 90° C. for 1 hr. The mixture was allowed to cool to room temperature, and stirred for 1 hr. The precipitate was collected by filtration, washed successively with diethyl ether and hexane, and dried to give the title compound (24.7 g) as pale-yellow crystals.

MS (ESI+): [M+H]$^+$ 261.1.

C) 5-methoxy-4-oxo-1-phenyl-1,4-dihydropyridazine-3-carboxylic acid

To a suspension of methyl 5-methoxy-4-oxo-1-phenyl-1,4-dihydropyridazine-3-carboxylate (39.04 g) in methanol (663 mL) was added dropwise 1N sodium hydroxide (300 mL) with stirring under ice-cooling, and the mixture was allowed to warm to room temperature and stirred for 1 hr. 1N Hydrochloric acid (300 mL) was added dropwise with stirring under ice-cooling, and the mixture was stirred at the same temperature for 1 hr. The precipitated crystals were collected by filtration, washed successively with water, ethanol/diisopropyl ether (1/2), and diisopropyl ether, and dried to give the title compound (36.1 g) as pale-yellow crystals.

MS (ESI+): [M+H]$^+$ 247.1.

D) N,5-dimethoxy-N-methyl-4-oxo-1-phenyl-1,4-dihydropyridazine-3-carboxamide Under an argon atmosphere, 5-methoxy-4-oxo-1-phenyl-1,4-dihydropyridazine-3-carboxylic acid (40 g) was dissolved in dimethylacetamide (600 mL) by heating to 50° C., and ice-cooled. With stirring, N,O-dimethylhydroxylamine hydrochloride (23.7 g), 1-hydroxybenzotriazole (21.9 g) and 1-ethyl-3-(3-dimethylaminopropyl)carbodiimide hydrochloride (46.6 g) were added, and triethylamine (81.4 mL) was added, and the mixture was allowed to warm to room temperature and stirred for 96 hr. To the reaction mixture was added ethyl acetate, and an insoluble material was filtered off. The filtrate was concentrated under reduced pressure to dryness, and the residue was purified by NH silica gel column chromatography (ethyl acetate/methanol) to give the title compound (39.2 g) as white crystals.

MS (ESI+): [M+H]$^+$ 290.1.

E) 3-acetyl-5-methoxy-1-phenylpyridazin-4(1H)-one

Under an argon atmosphere, to a stirring solution of N,5-dimethoxy-N-methyl-4-oxo-1-phenyl-1,4-dihydropyridazine-3-carboxamide (20 g) in tetrahydrofuran (1 L) was added dropwise, under cooling at −69° C., methyl magnesium bromide solution (1 M in THF, 138 mL). After stirring at −69° C. for 1.5 hr, a saturated aqueous ammonium chloride solution was added. Thereafter, the mixture was warmed to room temperature in 1.5 hr, and the reaction mixture was partitioned. The organic layer was washed with saturated brine, and dried over anhydrous magnesium sulfate. The aqueous layer was extracted with ethyl acetate, and the obtained extract was dried over anhydrous magnesium sulfate. The organic layer and the extract were combined, and concentrated under reduced pressure to dryness. The residue was purified by silica gel column chromatography (ethyl acetate/methanol) to give the title compound (13.22 g) as a pale-yellow solid.

MS (ESI+): [M+H]$^+$ 245.1.

F) 5-methoxy-3-(1-methyl-1H-pyrazol-5-yl)-1-phenylpyridazin-4(1H)-one

To a suspension of 3-acetyl-5-methoxy-1-phenylpyridazin-4(1H)-one (6.0 g) in dimethylformamide dimethylacetal (49.33 mL) was added acetonitrile (18 mL) and the mixture was stirred at 90° C. for 4.5 hr. The reaction mixture was allowed to cool to room temperature, and concentrated under reduced pressure to dryness. The residue was dissolved in ethanol (42.3 mL). To the reaction mixture was added dropwise with stirring under ice-cooling a solution of methylhydrazine (2.26 g) in 10% trifluoroacetic acid-containing ethanol (84.58 mL). The mixture was stirred at the same temperature for 10 min, allowed to warm to room temperature, and stirred for 18 hr. The crystals precipitated in the reaction mixture was collected by filtration, washed successively with ethanol and diisopropyl ether, and dried to give the title compound (3.81 g) as pale-yellow crystals. Furthermore, the filtrate and the washing were combined, and concentrated under reduced pressure to dryness. The residue was purified by silica gel column chromatography (ethyl acetate/methanol) to give the title compound (0.84 g) as pale-yellow crystals.

MS (ESI+): [M+H]$^+$ 283.2.

G) 5-hydroxy-3-(1-methyl-1H-pyrazol-5-yl)-1-phenylpyridazin-4(1H)-one

To a solution of sodium iodide (7.49 g) in acetonitrile (300 mL) was added chlorotrimethylsilane (6.35 mL) at room temperature with stirring, and the mixture was stirred for 30 min. Then, 5-methoxy-3-(1-methyl-1H-pyrazol-5-yl)-1-phenylpyridazin-4(1H)-one (2.82 g) was added, and the mixture was stirred for 30 min at the same temperature and further refluxed for 7 hr. The reaction mixture was allowed to cool to room temperature, poured into water and the mixture was stirred for 30 min. The resulting precipitate was collected by filtration, washed successively with water, methanol, and diisopropyl ether, and dried to give the title compound (0.95 g) as pale-yellow needles. The filtrate was extracted with ethyl acetate, and the organic layer was washed with saturated brine, dried over anhydrous magnesium sulfate and concentrated under reduced pressure to give the title compound (1.70 g) as pale-yellow needles.

MS (ESI+): [M+H]$^+$ 269.1.

H) 5-[3-(1-methyl-1H-benzimidazol-2-yl)propoxy]-3-(1-methyl-1H-pyrazol-5-yl)-1-phenylpyridazin-4(1H)-one Toluene (20 mL) was added to di-tert-butyl diazene-1,2-dicarboxylate (345 mg), and triphenylphosphine (459 mg) and the mixture was stirred at room temperature for 10 min. Then, 5-hydroxy-3-(1-methyl-1H-pyrazol-5-yl)-1-phenylpyridazin-4(1H)-one (268 mg), and further, 3-(1-methyl-1H-benzimidazol-2-yl)propan-1-ol (285 mg) were added, and the mixture was stirred at room temperature for 64 hr. The crystals precipitated from the reaction mixture were collected by filtration, washed successively with toluene, methanol, and diisopropyl ether, and dried to give the title compound (217 mg).

MS (ESI+): [M+H]$^+$ 441.1.

Example 6

5-[2-(2,3-dihydro-1H-imidazo[1,2-a]benzimidazol-1-yl)ethoxy]-3-(1-methyl-1H-pyrazol-5-yl)-1-phenylpyridazin-4(1H)-one A suspension of 5-hydroxy-3-(1-methyl-1H-pyrazol-5-yl)-1-phenylpyridazin-4(1H)-one (54 mg), 1-(2-chloroethyl)-2,3-dihydro-1H-imidazo[1,2-a]benzimidazole (49 mg), cesium carbonate (98 mg), and sodium iodide (33 mg) in dimethylformamide (4 mL) was stirred at 70° C. for 15 hr. The reaction mixture was filtered, and the obtained insoluble material was washed with ethyl acetate. The filtrate and washing were combined, and concentrated under reduced pressure to dryness. The residue was purified by silica gel column chromatography (ethyl acetate/methanol). A fraction containing the title compound was again purified by NH silica gel column chromatography (ethyl acetate/methanol) to give the title compound (10 mg) as a white solid.

MS (ESI+): [M+H]$^+$ 454.2.

Example 7

3-(1-methyl-1H-pyrazol-5-yl)-1-phenyl-5-(2-quinolin-2-ylethoxy)pyridazin-4(1H)-one Toluene (20 mL) was added to di-tert-butyl diazene-1,2-dicarboxylate (345 mg), triphenylphosphine (459 mg) and the mixture was stirred at room temperature for 10 min. Then, 5-hydroxy-3-(1-methyl-1H-pyrazol-5-yl)-1-phenylpyridazin-4(1H)-one (268 mg), and further, 2-quinolin-2-ylethanol (260 mg) were added, and the mixture was stirred at room temperature for 64 hr. The reaction mixture was concentrated under reduced pressure, and the residue was purified by silica gel column chromatography (ethyl acetate/methanol). A fraction containing the title compound was again purified by NH silica gel column chromatography (hexane/ethyl acetate) and crystallized from hexane/ethyl acetate to give the title compound (297 mg) as white needles.

MS (ESI+): [M+H]$^+$ 424.21.

Example 8

3-(1-methyl-1H-pyrazol-5-yl)-1-phenyl-5-(quinolin-2-ylmethoxy)pyridazin-4(1H)-one To a solution of 5-hydroxy-3-(1-methyl-1H-pyrazol-5-yl)-1-phenylpyridazin-4(1H)-one (268 mg) in dimethylformamide (10 mL) was added cesium carbonate (782 mg), 2-(chloromethyl)quinoline hydrochloride (236 mg) was added with stirring under ice-cooling, and the mixture was allowed to warm to room temperature and stirred for 64 hr. Water was added to the reaction mixture and the mixture was stirred for 1 hr. The precipitated crystals were collected by filtration, washed successively with water, methanol and diisopropyl ether, and dried to give the title compound (226 mg) as a white solid.

MS (ESI+): [M+H]$^+$ 410.20.

Example 9

5-(quinolin-2-ylmethoxy)-1-[3-(trifluoromethyl)phenyl]pyridazin-4(1H)-one

A) 3-bromo-5-methoxy-1-[3-(trifluoromethyl)phenyl]pyridazin-4(1H)-one

Isoamyl nitrite (4.95 mL) and copper(II) bromide (3.83 g) were suspended in dimethylformamide (41 mL), and a solution of 3-amino-5-methoxy-1-[3-(trifluoromethyl)phenyl]pyridazin-4(1H)-one (4.09 g) in dimethylformamide (20 mL) was added at 0° C. The reaction mixture was stirred at 0° C. for 1 hr and further at 60° C. for 3 hr. The reaction mixture was diluted with brine, and extracted with ethyl acetate. The extract was dried over anhydrous magnesium sulfate and filtered, and the filtrate was concentrated. The residue was purified by silica gel column chromatography (ethyl acetate/hexane) and solidified in ethyl acetate/hexane to give the title compound (3.69 g).

MS (ESI+): [M+H]$^+$ 349.1 and 351.2.

B) 5-methoxy-1-[3-(trifluoromethyl)phenyl]pyridazin-4 (H)-one

3-Bromo-5-methoxy-1-[3-(trifluoromethyl)phenyl]pyridazin-4(1H)-one (0.800 g) and palladium on carbon (0.24 g, palladium 10%, 50% water moistened product) were suspended in tetrahydrofuran (14 mL), and the suspension was stirred under a hydrogen atmosphere at room temperature for 2 days and half. The reaction mixture was filtered through celite, and the filtrate was concentrated, and the residue was purified by silica gel column chromatography (ethyl acetate/hexane→ethyl acetate/methanol) to give the title compound (0.185 g).
MS (ESI+): [M+H]$^+$ 270.99.

C) 5-(quinolin-2-ylmethoxy)-1-[3-(trifluoromethyl)phenyl]pyridazin-4(1H)-one

Sodium iodide (0.2772 g) and chlorotrimethylsilane (0.235 mL) were stirred in acetonitrile (1.85 mL) at room temperature for 30 min. A solution of 5-methoxy-1-[3-(trifluoromethyl)phenyl]pyridazin-4(1H)-one (0.100 g) in acetonitrile (3.7 mL) was added at room temperature. The reaction mixture was heated under reflux for 3 hr. The reaction mixture was cooled to room temperature, diluted with water, and extracted with ethyl acetate. The extract was washed with saturated brine, dried over anhydrous sodium sulfate and filtered, and the filtrate was concentrated, purified by silica gel column chromatography (ethyl acetate/hexane-methanol/ethyl acetate), and concentrated under reduced pressure. The obtained residue, potassium carbonate (0.1125 g) and 2-(chloromethyl)quinoline hydrochloride (0.0871 g) were suspended in N,N-dimethylformamide (2 mL), and the mixture was stirred at room temperature for 14 hr, and at 60° C. for 5 hr. The reaction mixture was cooled to room temperature, diluted with water, and extracted with ethyl acetate. The extract was washed with brine, dried over anhydrous sodium sulfate and filtered, and the filtrate was concentrated. The residue was purified by NH silica gel column chromatography (ethyl acetate/hexane), silica gel column chromatography (ethyl acetate/hexane) and HPLC, and recrystallized from ethyl acetate/hexane to give the title compound (0.0527 g).
MS (ESI+): [M+H]$^+$ 398.3.

Example 10

1-methyl-5-{2-[(1-methyl-1H-benzimidazol-2-yl)oxy]ethoxy}-3-(1-phenyl-1H-pyrazol-5-yl)pyridazin-4(1H)-one A) 2-[(1-methyl-1H-benzimidazol-2-yl)oxy]ethanol Under an argon atmosphere, metal sodium (635 mg) was added to anhydrous ethanediol (12 mL), and the mixture was stirred at 60° C. for 3 hr. Then, 2-chloro-1-methyl-1H-benzimidazole (4.0 g) was added and the mixture was stirred with heating at 90° C. for 5 hr. The mixture was allowed to cool to room temperature, diluted with water and extracted with ethyl acetate. The organic layer was washed with saturated brine, dried over magnesium sulfate, and concentrated under reduced pressure. The residue was purified by silica gel column chromatography (ethyl acetate/hexane) to give the title compound (3.0 g).
MS (ESI+): [M+H]$^+$ 193.1.

B) 1-methyl-5-{2-[(1-methyl-1H-benzimidazol-2-yl)oxy]ethoxy}-3-(1-phenyl-1H-pyrazol-5-yl)pyridazin-4(1H)-one By a method similar to step C of Example 3, the title compound (86 mg) was obtained from di-tert-butyl diazene-1,2-dicarboxylate (104 mg), triphenylphosphine (138 mg), 5-hydroxy-1-methyl-3-(1-phenyl-1H-pyrazol-5-yl)pyridazin-4(1H)-one (80 mg), and 2-[(1-methyl-1H-benzimidazol-2-yl)oxy]ethanol (86 mg).
MS (ESI+): [M+H]$^-$ 443.0.

Example 11

5-(3-imidazo[1,2-a]pyridin-2-ylpropoxy)-1-methyl-3-(1-phenyl-1H-pyrazol-5-yl)pyridazin-4(1H)-one A) methyl 3-imidazo[1,2-a]pyridin-2-ylpropanoate To a solution of 3-imidazo[1,2-a]pyridin-2-ylpropanoic acid (472 mg) in methanol (24.8 mL) was added thionyl chloride (0.215 mL), and the mixture was stirred at 60° C. for 3.5 hr. To the reaction mixture was added, under ice-cooling, saturated aqueous sodium hydrogen carbonate solution, and the mixture was extracted with ethyl acetate. The organic layer was washed successively with water and saturated brine, dried over magnesium sulfate, and concentrated under reduced pressure. The residue was purified by silica gel column chromatography (ethyl acetate/hexane) to give the title compound (402 mg).
MS (ESI+): [M+H]$^+$ 205.2.

B) 3-imidazo[1,2-a]pyridin-2-ylpropan-1-ol

Under an argon atmosphere, to a solution of calcium chloride (268 mg) in ethanol (4 mL) were added THF (2.8 mL) and sodium tetrahydroborate (183 mg) and the mixture was stirred at 0° C. for 30 min. Then, a solution of methyl 3-imidazo[1,2-a]pyridin-2-ylpropanoate (395 mg) in THF (1.2 mL) was added dropwise, and the mixture was allowed to warm to room temperature and stirred for 18 hr. Under ice-cooling, to the reaction mixture was added 1N hydrochloric acid (4.84 mL), and the mixture was concentrated under reduced pressure. The residue was purified by silica gel column chromatography (ethyl acetate/methanol) to give the title compound (223 mg).
MS (ESI+): [M+H]$^+$ 177.2.

C) 5-(3-imidazo[1,2-a]pyridin-2-ylpropoxy)-1-methyl-3-(1-phenyl-1H-pyrazol-5-yl)pyridazin-4(1H)-one By a method similar to step C of Example 3, the title compound (26 mg) was obtained from di-tert-butyl diazene-1,2-dicarboxylate (104 mg), triphenylphosphine (138 mg), 5-hydroxy-1-methyl-3-(1-phenyl-1H-pyrazol-5-yl)pyridazin-4(1H)-one (80 mg), 3-imidazo[1,2-a]pyridin-2-ylpropan-1-ol (79 mg).
MS (ESI+): [M+H]$^+$ 427.0.

Example 12

1-methyl-5-[3-(3-methyl-3H-imidazo[4,5-b]pyridin-2-yl)propoxy]-3-(1-phenyl-1H-pyrazol-5-yl)pyridazin-4(1H)-one A) 2-[3-(benzyloxy)propyl]-3H-imidazo[4,5-b]pyridine 4-(Benzyloxy)butanoic acid (5.0 g) and 2,3-diaminopyridine (1.12 g) were stirred at 150° C. for 10 hr. Under ice-cooling, to the reaction mixture was added concentrated aqueous ammonia, and the mixture was extracted with ethyl acetate. The organic layer was washed with saturated brine, dried over anhydrous sodium sulfate, and concentrated under reduced pressure. The residue was purified by silica gel column chromatography (ethyl acetate/hexane) to give the title compound (2.36 g).
MS (ESI+): [M+H]$^+$ 268.1.

B) 2-[3-(benzyloxy)propyl]-3-methyl-3H-imidazo[4,5-b]pyridine

Under an argon atmosphere, to a solution of 2-[3-(benzyloxy)propyl]-3H-imidazo[4,5-b]pyridine (2 g) in DMF (40 mL) was added 60% sodium hydride (0.299 g), and the mixture was stirred under ice-cooling for 30 min. Then, dimethylsulfuric acid (0.75 mL) was added, and the mixture was stirred at room temperature for 17 hr. To the reaction mixture was added methanol (5 mL), and the mixture was concentrated under reduced pressure. The residue was purified by silica gel column chromatography (ethyl acetate/methanol) to give the title compound (1.2 g).
MS (ESI+): [M+H]$^+$ 282.1.

C) 3-(3-methyl-3H-imidazo[4,5-b]pyridin-2-yl)propan-1-ol

A mixture of 2-[3-(benzyloxy)propyl]-3-methyl-3H-imidazo[4,5-b]pyridine (1.8 g), 20% palladium hydroxide on carbon (2.35 g, containing water (50%)), and formic acid (8.45 mL) in methanol (84.5 mL) was refluxed for 6 hr. The mixture was allowed to cool to room temperature, and the catalyst was filtered off. The obtained filtrate was concentrated under reduced pressure. The residue was purified by NH silica gel column chromatography (ethyl acetate/hexane) to give the title compound (1.0 g).
MS (ESI+): [M+H]$^+$ 192.1.

D) 1-methyl-5-[3-(3-methyl-3H-imidazo[4,5-b]pyridin-2-yl)propoxy]-3-(1-phenyl-1H-pyrazol-5-yl)pyridazin-4(1H)-one By a method similar to step C of Example 3, the title compound (119 mg) was obtained from di-tert-butyl diazene-1,2-dicarboxylate (127 mg), triphenylphosphine (168 mg), 5-hydroxy-1-methyl-3-(1-phenyl-1H-pyrazol-5-yl)pyridazin-4(1H)-one (98 mg), and 3-(3-methyl-3H-imidazo[4,5-b]pyridin-2-yl)propan-1-ol (105 mg).
MS (ESI+): [M+H]$^+$ 442.04.

Example 13

1-(cyclopropylmethyl)-5-[3-(3-methyl-3H-imidazo[4,5-b]pyridin-2-yl)propoxy]-3-(1-phenyl-1H-pyrazol-5-yl)pyridazin-4(1H)-one By a method similar to step C of Example 3, the title compound (132 mg) was obtained from di-tert-butyl diazene-1,2-dicarboxylate (127 mg), triphenylphosphine (168 mg), 1-(cyclopropylmethyl)-5-hydroxy-3-(1-phenyl-1H-pyrazol-5-yl)pyridazin-4(1H)-one (113 mg), and 3-(3-methyl-3H-imidazo[4,4-b]pyridin-2-yl)propan-1-ol (105 mg).
MS (ESI+): [M+H]$^+$ 482.0.

Example 14

1-(cyclopropylmethyl)-5-{2-[(1-methyl-1H-benzimidazol-2-yl)oxy]ethoxy}-3-(1-phenyl-1H-pyrazol-5-yl)pyridazin-4 (H)-one By a method similar to step C of Example 3, the title compound (105 mg) was obtained from di-tert-butyl diazene-1,2-dicarboxylate (104 mg), triphenylphosphine (138 mg), 1-(cyclopropylmethyl)-5-hydroxy-3-(1-phenyl-1H-pyrazol-5-yl)pyridazin-4(1H)-one (93 mg), and 2-[(1-methyl-1H-benzimidazol-2-yl)oxy]ethanol (86 mg).
MS (ESI+): [M+H]$^+$ 483.1.

Example 15

1-(cyclopropylmethyl)-3-(1-phenyl-1H-pyrazol-5-yl)-5-[2-(quinolin-2-yloxy)ethoxy]pyridazin-4(1H)-one A) 2-(quinolin-2-yloxy)ethanol By a method similar to step A of Example 10, the title compound (4.18 g) was obtained from anhydrous ethanediol (12 mL), metal sodium (646 mg), and 2-chloroquinoline (4 g).
MS (ESI+): [M+H]$^+$ 190.21.

B) 1-(cyclopropylmethyl)-3-(1-phenyl-1H-pyrazol-5-yl)-5-[2-(quinolin-2-yloxy)ethoxy]pyridazin-4(1H)-one By a method similar to step C of Example 3, the title compound (27 mg) was obtained from di-tert-butyl diazene-1,2-dicarboxylate (104 mg), triphenylphosphine (138 mg), 1-(cyclopropylmethyl)-5-hydroxy-3-(1-phenyl-1H-pyrazol-5-yl)pyridazin-4(1H)-one (93 mg), and 2-(quinolin-2-yloxy)ethanol (85 mg).
MS (ESI+): [M+H]$^+$ 480.3.

Example 16

1-(cyclopropylmethyl)-5-(3-imidazo[1,2-a]pyridin-2-ylpropoxy)-3-(1-phenyl-1H-pyrazol-5-yl)pyridazin-4(1H)-one By a method similar to step C of Example 3, the title compound (60 mg) was obtained from di-tert-butyl diazene-1,2-dicarboxylate (104 mg), triphenylphosphine (138 mg), 1-(cyclopropylmethyl)-5-hydroxy-3-(1-phenyl-1H-pyrazol-5-yl)pyridazin-4(1H)-one (93 mg), and 3-imidazo[1,2-a]pyridin-2-ylpropan-1-ol (71.6 mg).
MS (ESI+): [M+H]$^+$ 467.4.

Example 17

1-(cyclopropylmethyl)-3-(1-phenyl-1H-pyrazol-5-yl)-5-(quinolin-2-ylmethoxy)pyridazin-4(1H)-one By a method similar to Example 2, the title compound (98 mg) was obtained from 1-(cyclopropylmethyl)-5-hydroxy-3-(1-phenyl-1H-pyrazol-5-yl)pyridazin-4(1H)-one (93 mg), 2-(chloromethyl)quinoline.hydrochloride (70.7 mg), and cesium carbonate (235 mg).
MS (ESI+): [M+H]$^+$ 450.4.

Example 18

1-(cyclopropylmethyl)-3-(1-phenyl-1H-pyrazol-5-yl)-5-(quinolin-7-ylmethoxy)pyridazin-4(1H)-one A) quinolin-7-ylmethanol To a solution of 7-methylquinoline (2.86 g) in ethyl acetate (100 mL) were added N-bromosuccinimide (3.56 g) and 2,2'- azobis(isobutyronitrile) (197 mg) at room temperature, and the mixture was refluxed for 1.5 hr. The reaction mixture was allowed to cool to room temperature, and washed with water. The obtained organic layer was concentrated under reduced pressure, to the residue were added DME (200 mL), water (100 mL), and silver carbonate (27.6 g), and the mixture was stirred at room temperature for 20 hr. The insoluble material was filtered off, and the filtrate was concentrated under reduced pressure. The residue was purified by silica gel column chromatography (ethyl acetate/methanol), and then purified by NH silica gel column chromatography (ethyl acetate/hexane) to give the title compound (94 mg).

MS (ESI+): [M+H]$^+$ 160.2.

B) 1-(cyclopropylmethyl)-3-(1-phenyl-1H-pyrazol-5-yl)-5-(quinolin-7-ylmethoxy)pyridazin-4(1H)-one By a method similar to step C of Example 3, the title compound (41 mg) was obtained from di-tert-butyl diazene-1,2-dicarboxylate (104 mg), triphenylphosphine (138 mg), 1-(cyclopropylmethyl)-5-hydroxy-3-(1-phenyl-1H-pyrazol-5-yl)pyridazin-4(1H)-one (93 mg), and quinolin-7-ylmethanol (71.6 mg).

MS (ESI+): [M+H]$^+$ 450.4.

Example 19

1-(cyclopropylmethyl)-5-[2-(1H-imidazo[1,2-a]imidazol-1-yl)ethoxy]-3-(1-phenyl-1H-pyrazol-5-yl)pyridazin-4(1H)-one A) 1H-imidazo[1,2-a]imidazole.hydrochloride To a solution of 2-aminoimidazole-sulfate (2 g), 2-bromo-1,1-diethoxyethane (7.49 g) in DMF (40 mL) was added sodium amide (2.36 g) in 4 portions within 1 hr. The reaction mixture was stirred for 2.5 hr, sodium amide (0.59 g) was further added, and the mixture was stirred at room temperature for 12 hr. To the reaction mixture were added ice and 1M aqueous sodium carbonate solution, and the mixture was extracted with ethyl acetate. The organic layer was washed with water, and concentrated under reduced pressure. To the residue was added 2N hydrochloric acid, and ethyl acetate was added. Under an argon atmosphere, the aqueous layer was stirred under refluxing conditions for 30 min, and concentrated under reduced pressure. The residue was adsorbed onto ion exchange resin (IR-120; type H), and the fraction eluted with 0.6N-1N hydrochloric acid was concentrated to give the title compound (0.24 g).

MS (ESI+): [M+H]$^+$ 108.0.

B) 1-(2-chloroethyl)-1H-imidazo[1,2-a]imidazole

Under an argon atmosphere, to a solution of 1H-imidazo[1,2-a]imidazole.hydrochloride (85 mg) in DMF (3 mL) was added 60% sodium hydride (52.1 mg), and the mixture was stirred under ice-cooling for 1 hr. Then, a solution of 1-bromo-2-chloroethane (170 mg) in DMF (0.5 mL) was added, and the mixture was stirred at room temperature for 18 hr. The reaction mixture was concentrated under reduced pressure, and the residue was purified by silica gel column chromatography (ethyl acetate/methanol) to give the title compound (38 mg).

MS (ESI+): [M+H]$^+$ 170.1.

C) 1-(cyclopropylmethyl)-5-[2-(1H-imidazo[1,2-a]imidazol-1-yl)ethoxy]-3-(1-phenyl-1H-pyrazol-5-yl)pyridazin-4(1H)-one By a method similar to Example 2, the title compound (46 mg) was obtained from 1-(cyclopropylmethyl)-5-hydroxy-3-(1-phenyl-1H-pyrazol-5-yl)pyridazin-4(1H)-one (56.4 mg), 1-(2-chloroethyl)-1H-imidazo[1,2-a]imidazole (37.2 mg), cesium carbonate (104 mg), and sodium iodide (61.7 mg).

MS (ESI+): [M+H]$^+$ 442.0.

Example 20

1-cyclobutyl-5-[3-(1-methyl-1H-benzimidazol-2-yl)propoxy]-3-(1-phenyl-1H-pyrazol-5-yl)pyridazin-4(1H)-one A) 1-cyclobutyl-5-methoxy-3-(1-phenyl-1H-pyrazol-5-yl)pyridazin-4(1H)-one Under an argon atmosphere, to a solution of 5-methoxy-3-(1-phenyl-1H-pyrazol-5-yl)pyridazin-4-ol (2.0 g) in DMF (40 mL) was added under ice-cooling 60% sodium hydride (596 mg), and the mixture was stirred for 1.5 hr. Then, bromocyclobutane (1.05 mL) was added, and the mixture was stirred at room temperature for 16 hr. To the reaction mixture was added methanol, and the mixture was concentrated under reduced pressure. The residue was purified by NH silica gel column chromatography (ethyl acetate/methanol) and further purified by HPLC to give the title compound (0.92 g).

MS (ESI+): [M+H]$^+$ 323.3.

B) 1-cyclobutyl-5-hydroxy-3-(1-phenyl-1H-pyrazol-5-yl)pyridazin-4(1H)-one

To a solution of sodium iodide (2.11 g) in acetonitrile (84.3 mL) was added at room temperature chlorotrimethylsilane (1.78 mL) and the mixture was stirred for 30 min. Then, 1-cyclobutyl-5-methoxy-3-(1-phenyl-1H-pyrazol-5-yl)pyridazin-4(1H)-one (0.91 g) was added, and the mixture was stirred at room temperature for 30 min, and further refluxed for 3 hr. The reaction mixture was allowed to cool to room temperature, water was added, and the mixture was stirred for 30 min, and extracted with ethyl acetate. The organic layer was washed with aqueous sodium thiosulfate solution and saturated brine, dried over anhydrous magnesium sulfate, and concentrated under reduced pressure. The residue was triturated with diisopropyl ether, and collected by filtration to give the title compound (800 mg).

MS (ESI+): [M+H]$^+$ 309.3.

C) 1-cyclobutyl-5-[3-(1-methyl-1H-benzimidazol-2-yl)propoxy]-3-(1-phenyl-1H-pyrazol-5-yl)pyridazin-4(1H)-one By a method similar to step C of Example 3, the title compound (53 mg) was obtained from di-tert-butyl diazene-1,2-dicarboxylate (104 mg), triphenylphosphine (138 mg), 1-cyclobutyl-5-hydroxy-3-(1-phenyl-1H-pyrazol-5-yl)pyridazin-4(1H)-one (93 mg), and 3-(1-methyl-1H-benzimidazol-2-yl)propan-1-ol (86 mg).

MS (ESI+): [M+H]$^+$ 481.4.

Example 21

1-cyclobutyl-5-[3-(3-methyl-3H-imidazo[4,5-b]pyridin-2-yl)propoxy]-3-(1-phenyl-1H-pyrazol-5-yl)pyridazin-4 (H)-one By a method similar to step C of Example 3, the title compound (139 mg) was obtained from di-tert-butyl diazene-1,2-dicarboxylate (127 mg), triphenylphosphine (168 mg), 1-cyclobutyl-5-hydroxy-3-(1-phenyl-1H-pyrazol-5-yl)pyridazin-4(1H)-one (113 mg), and 3-(3-methyl-3H-imidazo[4,5-b]pyridin-2-yl)propan-1-ol (105 mg).
MS (ESI+): [M+H]$^+$ 482.1.

Example 22

1-cyclobutyl-5-[2-(2,3-dihydro-1H-imidazo[1,2-a]benzimidazol-1-yl)ethoxy]-3-(1-phenyl-1H-pyrazol-5-yl)pyridazin-4 (H)-one By a method similar to Example 2, the title compound (129 mg) was obtained from 1-cyclobutyl-5-hydroxy-3-(1-phenyl-1H-pyrazol-5-yl)pyridazin-4(1H)-one (93 mg), 1-(2-chloroethyl)-2,3-dihydro-1H-imidazo[1,2-a]benzimidazole (100 mg), cesium carbonate (171 mg), and sodium iodide (101 mg).
MS (ESI+): [M+H]$^+$ 494.4.

Example 23

1-cyclobutyl-5-{2-[(1-methyl-1H-benzimidazol-2-yl)oxy]ethoxy}-3-(1-phenyl-1H-pyrazol-5-yl)pyridazin-4(1H)-one By a method similar to step C of Example 3 the title compound (91 mg) was obtained from di-tert-butyl diazene-1,2-dicarboxylate (104 mg), triphenylphosphine (138 mg), 1-cyclobutyl-5-hydroxy-3-(1-phenyl-1H-pyrazol-5-yl)pyridazin-4(1H)-one (93 mg), and 2-[(1-methyl-1H-benzimidazol-2-yl)oxy]ethanol (86 mg).
MS (ESI+): [M+H]$^+$ 483.0.

Example 24

1-cyclobutyl-5-(3-imidazo[1,2-a]pyridin-2-ylpropoxy)-3-(1-phenyl-1H-pyrazol-5-yl)pyridazin-4(1H)-one By a method similar to step C of Example 3, the title compound (55 mg) was obtained from di-tert-butyl diazene-1,2-dicarboxylate (104 mg), triphenylphosphine (138 mg), 1-cyclobutyl-5-hydroxy-3-(1-phenyl-1H-pyrazol-5-yl)pyridazin-4(1H)-one (93 mg), and 3-imidazo[1,2-a]pyridin-2-ylpropan-1-ol (79 mg).
MS (ESI+): [M+H]$^-$ 467.4.

Example 25

5-[3-(1-methyl-1H-benzimidazol-2-yl)propoxy]-3-(1-phenyl-1H-pyrazol-5-yl)-1-(2,2,2-trifluoroethyl)pyridazin-4(1H)-one A) 5-methoxy-3-(1-phenyl-1H-pyrazol-5-yl)-1-(2,2,2-trifluoroethyl)pyridazin-4(1H)-one By a method similar to step A of Example 20, the title compound (1.71 g) was obtained from 5-methoxy-3-(1-phenyl-1H-pyrazol-5-yl)pyridazin-4-ol (2.0 g), 60% sodium hydride (596 mg), and 2,2,2-trifluoroethyl trifluoromethanesulfonate (2.6 g).
MS (ESI+): [M+H]$^+$ 351.0.

B) 5-hydroxy-3-(1-phenyl-1H-pyrazol-5-yl)-1-(2,2,2-trifluoroethyl)pyridazin-4(1H)-one By a method similar to step B of Example 20, the title compound (1.2 g) was obtained from sodium iodide (3.75 g), chlorotrimethylsilane (3.17 mL), and 5-methoxy-3-(1-phenyl-1H-pyrazol-5-yl)-1-(2,2,2-trifluoroethyl)pyridazin-4(1H)-one (1.57 g).
MS (ESI+): [M+H]$^+$ 337.0.

C) 5-[3-(1-methyl-1H-benzimidazol-2-yl)propoxy]-3-(1-phenyl-1H-pyrazol-5-yl)-1-(2,2,2-trifluoroethyl)pyridazin-4(1H)-one By a method similar to step C of Example 3, the title compound (40 mg) was obtained from di-tert-butyl diazene-1,2-dicarboxylate (138 mg), triphenylphosphine (184 mg), 5-hydroxy-3-(1-phenyl-1H-pyrazol-5-yl)-1-(2,2,2-trifluoroethyl)pyridazin-4(1H)-one (135 mg), and 3-(1-methyl-1H-benzimidazol-2-yl)propan-1-ol (114 mg).
MS (ESI+): [M+H]$^+$ 509.0.

Example 26

5-[3-(3-methyl-3H-imidazo[4,5-b]pyridin-2-yl)propoxy]-3-(1-phenyl-1H-pyrazol-5-yl)-1-(2,2,2-trifluoroethyl)pyridazin-4(1H)-one By a method similar to step C of Example 3, the title compound (104 mg) was obtained from di-tert-butyl diazene-1,2-dicarboxylate (127 mg), triphenylphosphine (168 mg), 5-hydroxy-3-(1-phenyl-1H-pyrazol-5-yl)-1-(2,2,2-trifluoroethyl)pyridazin-4(1H)-one (123 mg), and 3-(3-methyl-3H-imidazo[4,5-b]pyridin-2-yl)propan-1-ol (105 mg).
MS (ESI+): [M+H]$^+$ 510.05.

Example 27

5-[2-(2,3-dihydro-1H-imidazo[1,2-a]benzimidazol-1-yl)ethoxy]-3-(1-phenyl-1H-pyrazol-5-yl)-1-(2,2,2-trifluoroethyl)pyridazin-4(1H)-one By a method similar to Example 2, the title compound (70 mg) was obtained from 5-hydroxy-3-(1-phenyl-1H-pyrazol-5-yl)-1-(2,2,2-trifluoroethyl)pyridazin-4(1H)-one (135 mg), 1-(2-chloroethyl)-2,3-dihydro-1H-imidazo[1,2-a]benzimidazole (133 mg), cesium carbonate (228 mg), and sodium iodide (90 mg).
MS (ESI+): [M+H]$^+$ 522.01.

The structural formulas and the like of the compounds of Examples 1-27 are shown in Table 1.

TABLE 1

| Example No. | IUPAC Name | Structure | Aditive | MS |
|---|---|---|---|---|
| 1 | 1-methyl-5-[3-(1-methyl-1H-benzimidazol-2-yl)propoxy]-3-(1-phenyl-1H-pyrazol-5-yl)pyridazin-4(1H)-one | 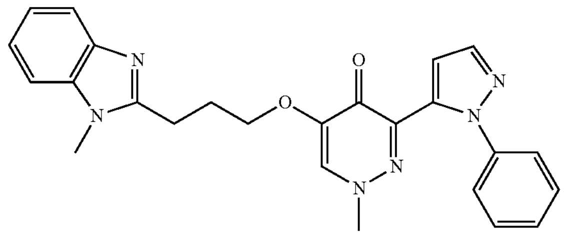 [SMILES: Cn1cc(OCCCc2nc3ccccc3n2C)c(=O)c(-c2ccnn2-c2ccccc2)n1] | — | 441.2 |
| 2 | 5-[2-(2,3-dihydro-1H-imidazo[1,2-a]benzimidazol-1-yl)ethoxy]-1-methyl-3-(1-phenyl-1H-pyrazol-5-yl)pyridazin-4(1H)-one | 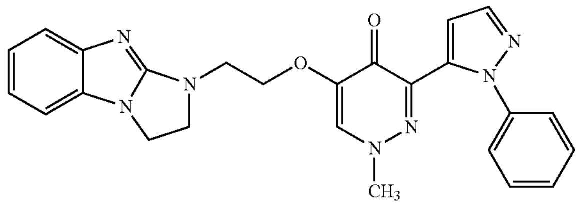 [SMILES: Cn1cc(OCCN2CCn3c2nc2ccccc23)c(=O)c(-c2ccnn2-c2ccccc2)n1] | — | 454.2 |
| 3 | 1-(cyclopropylmethyl)-5-[3-(1-methyl-1H-benzimidazol-2-yl)propoxy]-3-(1-phenyl-1H-pyrazol-5-yl)pyridazin-4(1H)-one | 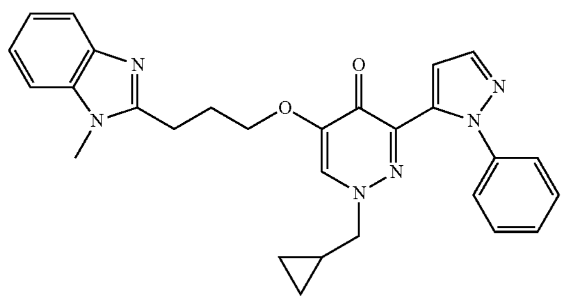 [SMILES: Cn1c(CCCOc2cn(CC3CC3)nc(-c3ccnn3-c3ccccc3)c2=O)nc2ccccc21] | — | 481.3 |
| 4 | 1-(cyclopropylmethyl)-5-[2-(2,3-dihydro-1H-imidazo[1,2-a]benzimidazol-1-yl)ethoxy]-3-(1-phenyl-1H-pyrazol-5-yl)pyridazin-4(1H)-one | 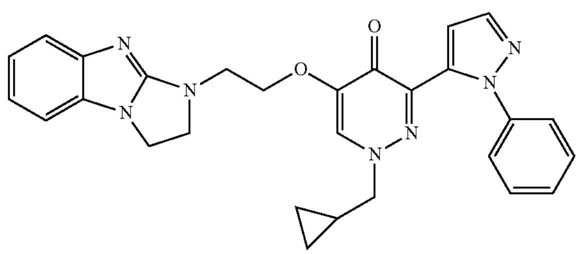 [SMILES: O=c1c(OCCN2CCn3c2nc2ccccc23)cn(CC2CC2)nc1-c1ccnn1-c1ccccc1] | — | 494.2 |
| 5 | 5-[3-(1-methyl-1H-benzimidazol-2-yl)propoxy]-3-(1-methyl-1H-pyrazol-5-yl)-1-phenylpyridazin-4(1H)-one | 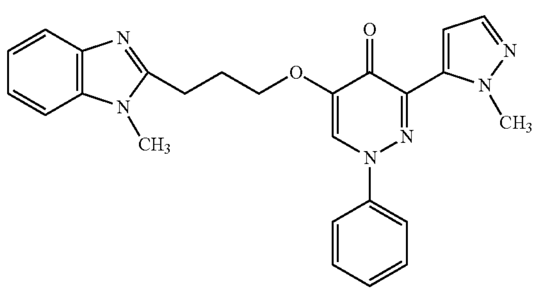 [SMILES: Cn1nccc1-c1nn(-c2ccccc2)cc(OCCCc2nc3ccccc3n2C)c1=O] | — | 441.2 |

TABLE 1-continued

| Example No. | IUPAC Name | Structure | Aditive | MS |
|---|---|---|---|---|
| 6 | 5-[2-(2,3-dihydro-1H-imidazo[1,2-a]benzimidazol-1-yl)ethoxy]-3-(1-methyl-1H pyrazol-5-yl)-1-phenylpyridazin-4(1H)-one | 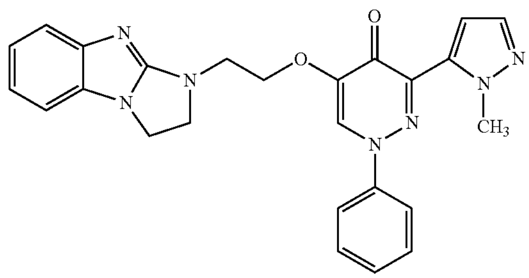 [SMILES: Cn1nccc1-c1nn(-c2ccccc2)cc(OCCN2CCn3c2nc2ccccc23)c1=O] | — | 454.2 |
| 7 | 3-(1-methyl-1H-pyrazol-5-yl)-1-phenyl-5-(2-quinolin-2-ylethoxy)pyridazin-4(1H)-one | 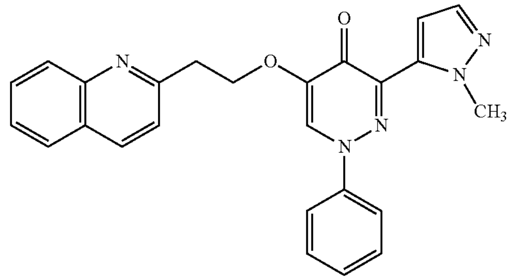 [SMILES: Cn1nccc1-c1nn(-c2ccccc2)cc(OCCc2ccc3ccccc3n2)c1=O] | — | 424.2 |
| 8 | 3-(1-methyl-1H-pyrazol-5-yl)-1-phenyl-5-(quinolin-2-ylmethoxy)pyridazin-4(1H)-one | 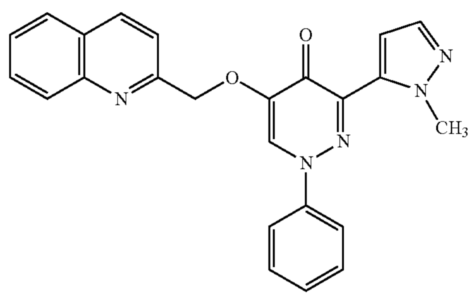 [SMILES: Cn1nccc1-c1nn(-c2ccccc2)cc(OCc2ccc3ccccc3n2)c1=O] | — | 410.2 |
| 9 | 5-(quinolin-2-ylmethoxy)-1-[3-(trifluoromethyl)phenyl]pyridazin-4(1H)-one | 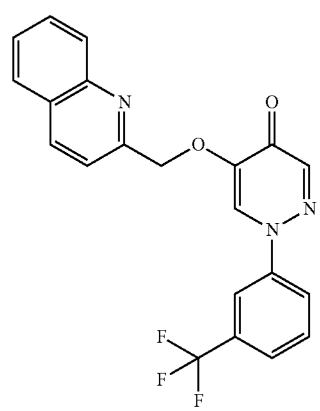 [SMILES: O=c1cnn(-c2cccc(C(F)(F)F)c2)cc1OCc1ccc2ccccc2n1] | — | 398.3 |
| 10 | 1-methyl-5-{2-[(1-methyl-1H-benzimilazol-2-yl)oxy]ethoxy}-3-(1-phenyl-1H-pyrazol-5-yl)pyridazin-4(1H)-one | 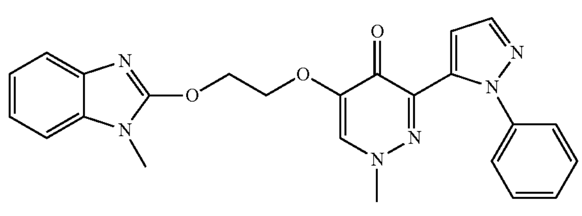 [SMILES: Cn1cc(OCCOc2nc3ccccc3n2C)c(=O)c(-c2ccnn2-c2ccccc2)n1] | — | 442.47 |

TABLE 1-continued

| Example No. | IUPAC Name | Structure | Aditive | MS |
|---|---|---|---|---|
| 11 | 5-(3-imidazo[1,2-a]pyridin-2-ylpropoxy)-1-methyl-3-(1-phenyl-1H-pyrazol-5-yl)pyridazin-4(1H)-one | 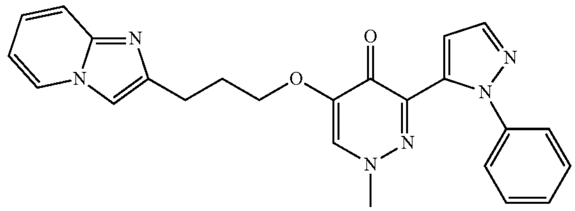 [SMILES: Cn1cc(OCCCc2cn3ccccc3n2)c(=O)c(-c2ccnn2-c2ccccc2)n1] | — | 426.47 |
| 12 | 1-methyl-5-[3-(3-methyl-3H-imidazo[4,5-b]pyridin-2-yl)propoxy]-3-(1-phenyl-1H-pyrazol-5-yl)pyridazin-4(1H)-one | 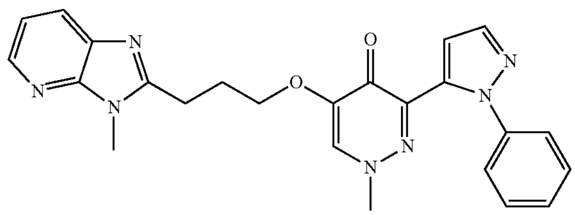 [SMILES: Cn1cc(OCCCc2nc3cccnc3n2C)c(=O)c(-c2ccnn2-c2ccccc2)n1] | — | 441.49 |
| 13 | 1-(cyclopropylmethyl)-5-[3-(3-methyl-3H-imidazo[4,5-b]pyridin-2-yl)propoxy]-3-(1-phenyl-1H-pyrazol-5-yl)pyridazin-4(1H)-one | 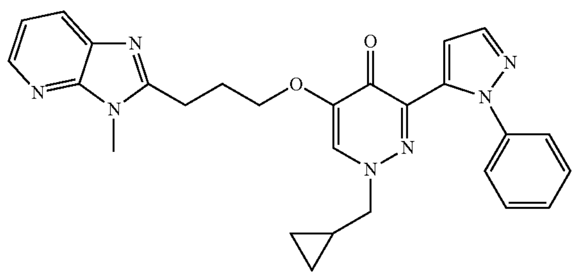 [SMILES: Cn1c(CCCOc2cn(CC3CC3)nc(-c3ccnn3-c3ccccc3)c2=O)nc2cccnc21] | — | 481.55 |
| 14 | 1-(cyclopropylmethyl)-5-{2-[(1-methyl-1H-benzimidazol-2-yl)oxy]ethoxy}-3-(1-phenyl-1H-pyrazol-5-yl)pyridazin-4(1H)-one | 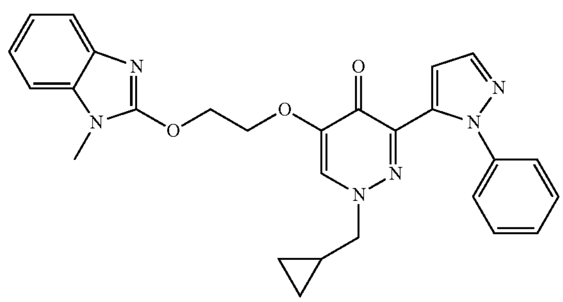 [SMILES: Cn1c(OCCOc2cn(CC3CC3)nc(-c3ccnn3-c3ccccc3)c2=O)nc2ccccc21] | — | 482.53 |
| 15 | 1-(cyclopropylmethyl)-3-(1-phenyl-1H-pyrazol-5-yl)-5-[2-(quinolin-2-yloxy)ethoxy]pyridazin-4(1H)-one | 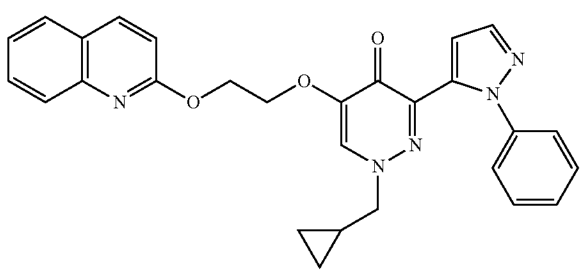 [SMILES: O=c1c(OCCOc2ccc3ccccc3n2)cn(CC2CC2)nc1-c1ccnn1-c1ccccc1] | — | 479.53 |

TABLE 1-continued

| Example No. | IUPAC Name | Structure | Aditive | MS |
|---|---|---|---|---|
| 16 | 1-(cyclopropylmethyl)-5-(3-imidazo[1,2-a]pyridin-2-ylpropoxy)-3-(1-phenyl-1H-pyrazol-5-yl)pyridazin-4(1H)-one | 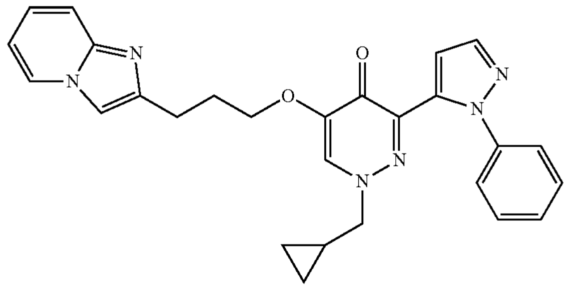 [SMILES: O=c1c(OCCCc2cn3ccccc3n2)cn(CC2CC2)nc1-c1ccnn1-c1ccccc1] | — | 466.53 |
| 17 | 1-(cyclopropylmethyl)-3-(1-phenyl-1H-pyrazol-5-yl)-5-(quinolin-2-ylmethoxy)pyridazin-4(1H)-one | 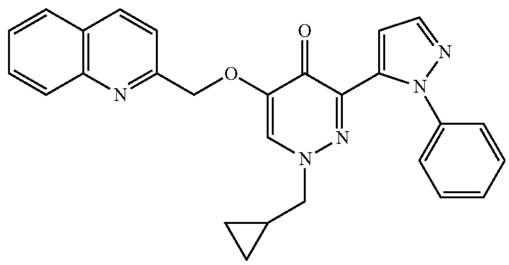 [SMILES: O=c1c(OCc2ccc3ccccc3n2)cn(CC2CC2)nc1-c1ccnn1-c1ccccc1] | — | 449.50 |
| 18 | 1-(cyclopropylmethyl)-3-(1-phenyl-1H-pyrazol-5-yl)-5-(quinolin-7-ylmethoxy)pyridazin-4(1H)-one | 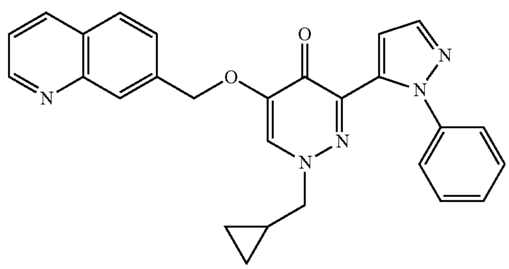 [SMILES: O=c1c(OCc2ccc3cccnc3c2)cn(CC2CC2)nc1-c1ccnn1-c1ccccc1] | — | 449.50 |
| 19 | 1-(cyclopropylmethyl)-5-[2-(1H-imidazo[1,2-a]imidazol-1-yl)ethoxy]-3-(1-phenyl-1H-pyrazol-5-yl)pyridazin-4(1H)-one | 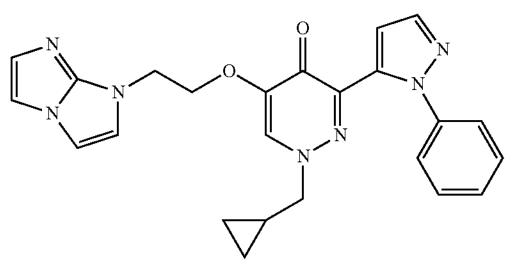 [SMILES: O=c1c(OCCn2ccn3ccnc23)cn(CC2CC2)nc1-c1ccnn1-c1ccccc1] | — | 441.49 |
| 20 | 1-cyclobutyl-5-[3-(1-methyl-1H-benzimidazol-2-yl)propoxy]-3-(1-phenyl-1H-pyrazol-5-yl)pyridazin-4(1H)-one | 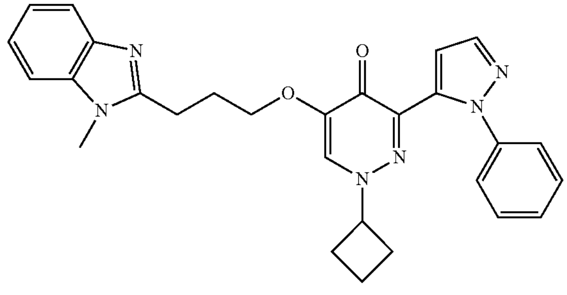 [SMILES: Cn1c(CCCOc2cn(C3CCC3)nc(-c3ccnn3-c3ccccc3)c2=O)nc2ccccc21] | — | 480.56 |

TABLE 1-continued

| Example No. | IUPAC Name | Structure | Aditive | MS |
|---|---|---|---|---|
| 21 | 1-cyclobutyl-5-[3-(3-methyl-3H-imidazo[4,5-b]pyridin-2-yl)propoxy]-3-(1-phenyl-1H-pyrazol-5-yl)pyridazin-4(1H)-one | 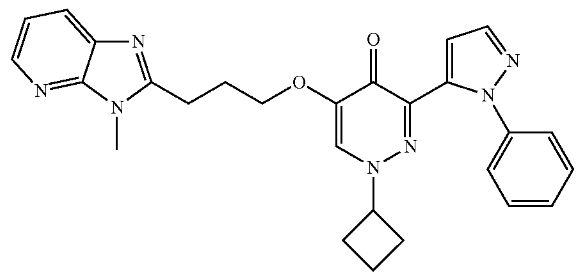 [SMILES: Cn1c(CCCOc2cn(C3CCC3)nc(-c3ccnn3-c3ccccc3)c2=O)nc2cccnc21] | — | 481.55 |
| 22 | 1-cyclobutyl-5-[2-(2,3-dihydro-1H-imidazo[1,2-a]benzimidazol-1-yl)ethoxy]-3-(1-phenyl-1H-pyrazol-5-yl)pyridazin-4(1H)-one | 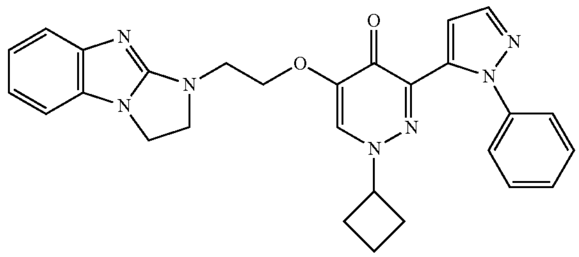 [SMILES: O=c1c(OCCN2CCn3c2nc2ccccc23)cn(C2CCC2)nc1-c1ccnn1-c1ccccc1] | — | 493.56 |
| 23 | 1-cyclobutyl-5-{2-[(1-methyl-1H-benzimidazol-2-yl)oxy]ethoxy}-3-(1-phenyl-1H-pyrazol-5-yl)pyridazin-4(1H)-one | 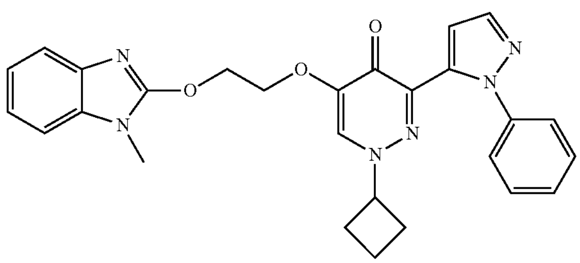 [SMILES: Cn1c(OCCOc2cn(C3CCC3)nc(-c3ccnn3-c3ccccc3)c2=O)nc2ccccc21] | — | 482.53 |
| 24 | 1-cyclobutyl-5-(3-imidazo[1,2-a]pyridin-2-ylpropoxy)-3-(1-phenyl-1H-pyrazol-5-yl)pyridazin-4(1H)-one | 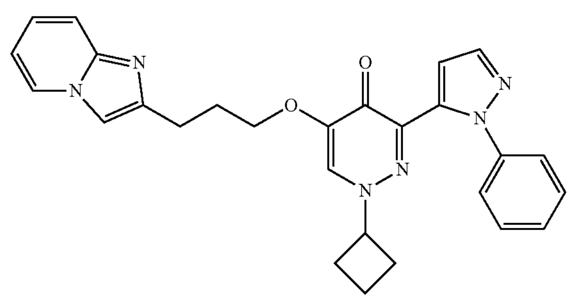 [SMILES: O=c1c(OCCCc2cn3ccccc3n2)cn(C2CCC2)nc1-c1ccnn1-c1ccccc1] | — | 466.53 |
| 25 | 5-[3-(1-methyl-1H-benzimidazol-2-yl)propoxy]-3-(1-phenyl-1H-pyrazol-5-yl)-1-(2,2,2-trifluoroethyl)pyridazin-4(1H)-one | 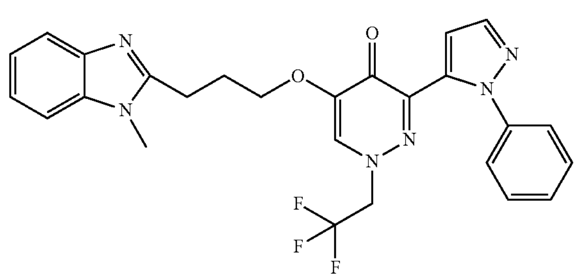 [SMILES: Cn1c(CCCOc2cn(CC(F)(F)F)nc(-c3ccnn3-c3ccccc3)c2=O)nc2ccccc21] | — | 508.5 |

TABLE 1-continued

| Example No. | IUPAC Name | Structure | Aditive | MS |
|---|---|---|---|---|
| 26 | 5-[3-(3-methyl-3H-imidazo[4,5-b]pyridin-2-yl)propoxy]-3-(1-phenyl-1H-pyrazol-5-yl)-1-(2,2,2-trifluoroethyl)pyridazin-4(1H)-one | 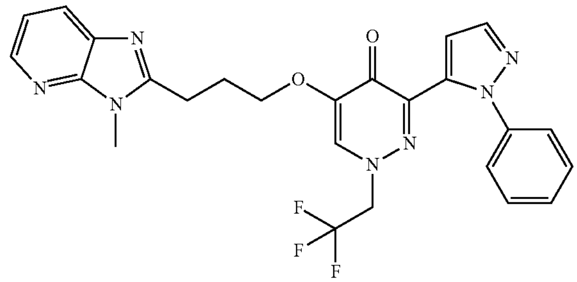 [SMILES: Cn1c(CCCOc2cn(CC(F)(F)F)nc(-c3ccnn3-c3ccccc3)c2=O)nc2cccnc21] | — | 509.48 |
| 27 | 5-[2-(2,3-dihydro-1H-imidazo[1,2-a]benzimidazol-1-yl)ethoxy]-3-(1-phenyl-1H-pyrazol-5-yl)-1-(2,2,2-trifluoroethyl)pyridazin-4(1H)-one | 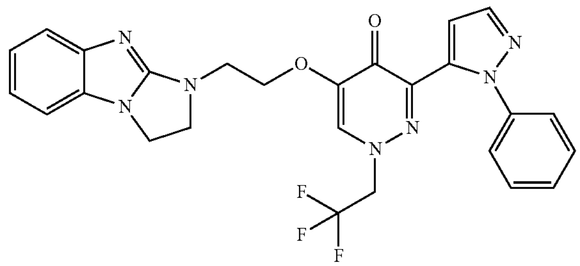 [SMILES: O=c1c(OCCN2CCn3c2nc2ccccc23)cn(CC(F)(F)F)nc1-c1ccnn1-c1ccccc1] | — | 521.49 |

Experimental Example 1

PDE10A Enzyme Activity Inhibition Test

Human PDE10A full-length gene was transfected into Sf9 or COS-7 cells. The cells were disrupted and centrifuged, and human PDE10A enzyme was obtained from the residue. The enzyme extracted from Sf9 cells was partially purified using His-tag affinity column. The enzyme was stored at −70° C. until use. The PDE activity was measured using an SPA (Scintillation Proximity Assay) (GE Healthcare). To measure the inhibitory activity of the compound, 10 μL of serially diluted compound was reacted with 20 μL of PDE enzyme in an assay buffer (50 mM HEPES-NaOH, 8.3 mM $MgCl_2$, 1.7 mM EGTA, 0.1% BSA (pH 7.4)) for min at room temperature. The final concentration of DMSO in the reaction mixture was 1 percent. The compounds were evaluated in duplicate in 96-well half-area plates (Corning). To start the reaction, 10 μL of substrate [$^3$H] cGMP (25 and 50 nM; GE Healthcare and PerkinElmer, respectively) was added to 40 μL. After 60 min of reaction at room temperature, yttrium SPA beads containing zinc sulphate were added (6 mg/mL, 20 μL) to terminate the reaction. After standing still for 1 hr, the measurement was performed using a scintillation counter (PerkinElmer) and the inhibition rate was calculated. The inhibition rate was calculated based on the control containing enzyme and DMSO as 0% and the control without enzyme as 100%. The results are shown in Table 2.

TABLE 2

| Example No. | inhibition rate (%) (1 μM) |
|---|---|
| 1 | 96 |
| 2 | 101 |
| 3 | 98 |
| 4 | 100 |
| 5 | 95.4 |
| 6 | 97.2 |
| 7 | 96.8 |
| 8 | 68.4 |
| 9 | 6.5 |
| 10 | 95 |
| 11 | 100 |
| 12 | 102 |
| 13 | 100 |
| 14 | 98 |
| 15 | 13 |
| 16 | 98 |
| 17 | 60 |
| 18 | 20 |
| 19 | 94 |
| 20 | 99 |
| 21 | 107 |
| 22 | 98 |
| 23 | 100 |
| 24 | 100 |
| 25 | 96 |
| 26 | 101 |
| 27 | 98 |

Formulation Example 1

| | |
|---|---|
| (1) compound of the Example 1 | 10.0 mg |
| (2) Lactose | 70.0 mg |
| (3) Cornstarch | 50.0 mg |
| (4) Soluble starch | 7.0 mg |
| (5) Magnesium stearate | 3.0 mg |

After 10.0 mg of the compound of Example 1 and 3.0 mg of magnesium stearate are granulated in 0.07 ml aqueous solution of soluble starch (7.0 mg as soluble starch) and then dried, the resulting mixture is mixed with 70.0 mg of lactose and 50.0 mg of cornstarch. The mixture is compressed to obtain a tablet.

INDUSTRIAL APPLICABILITY

The compound of the present invention has a PDE10A inhibitory action, and is useful as a medicament for the prophylaxis or treatment of mental diseases such as schizophrenia and the like, and the like.

This application is based on patent application No. 2010-175395 filed in Japan, the contents of which are encompassed in full herein.

The invention claimed is:

1. A compound represented by the formula (I):

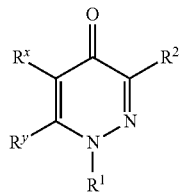

wherein a partial structural formula:

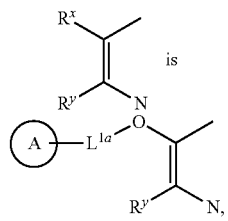

ring A is a nitrogen-containing fused heterocyclic group optionally substituted with 1 to 5 $C_{1-6}$ alkyl groups, wherein nitrogen(s) is/are the only heteroatom(s) in the heterocyclic group, $L^{1a}$ is —$X^2$—$Y^2$— ($X^2$ is a bond or —O—; $Y^2$ is an optionally substituted $C_{1-6}$ alkylene group), $R^1$ is (1) a $C_{1-6}$ alkyl group optionally substituted with 1 to 3 halogen atoms or one $C_{3-7}$ cycloalkyl group, (2) a $C_{3-7}$ cycloalkyl group, or (3) a $C_{6-14}$ aryl group optionally substituted with a $C_{1-6}$ alkyl group substituted with 1 to 3 halogen atoms, $R^2$ is a hydrogen atom, or a pyrazolyl group optionally substituted with a substituent selected from the group consisting of a $C_{1-6}$ alkyl group and a $C_{6-14}$ aryl group, and —$R^y$ is a hydrogen atom, or a salt thereof.

2. 5-[2-(2,3-Dihydro-1H-imidazo[1,2-a]benzimidazol-1-yl)ethoxy]-1-methyl-3-(1-phenyl-1H-pyrazol-5-yl)pyridazin-4(1H)-one or a salt thereof.

3. 1-(Cyclopropylmethyl)-5-[3-(1-methyl-1H-benzimidazol-2-yl)propoxy]-3-(1-phenyl-1H-pyrazol-5-yl)pyridazin-4(1H)-one or a salt thereof.

4. 1-(Cyclopropylmethyl)-5-[2-(2,3-dihydro-1H-imidazo[1,2-a]benzimidazol-1-yl)ethoxy]-3-(1-phenyl-1H-pyrazol-5-yl)pyridazin-4(1H)-one or a salt thereof.

5. 5-(3-Imidazo[1,2-a]pyridin-2-ylpropoxy)-1-methyl-3-(1-phenyl-1H-pyrazol-5-yl)pyridazin-4(1H)-one or a salt thereof.

6. 1-Cyclobutyl-5-[2-(2,3-dihydro-1H-imidazo[1,2-a]benzimidazol-1-yl)ethoxy]-3-(1-phenyl-1H-pyrazol-5-yl)pyridazin-4(1H)-one or a salt thereof.

7. A pharmaceutical composition comprising the compound according to claim 1 or a salt thereof, and a pharmacologically acceptable carrier.

8. The pharmaceutical composition according to claim 7, which is a phosphodiesterase 10A inhibitor.

* * * * *